US012575940B2

(12) United States Patent
Trudeau et al.

(10) Patent No.: US 12,575,940 B2
(45) Date of Patent: *Mar. 17, 2026

(54) INTERVERTEBRAL IMPLANTS, INSTRUMENTS, AND METHODS

(71) Applicant: Xtant Medical Holdings, Inc., Belgrade, MT (US)

(72) Inventors: Jeffrey L. Trudeau, Marquette, MI (US); Michael D. Kakuk, Skandia, MI (US); Stephen John Horvath, Leander, TX (US); Katie S. Barron, Negaunee, MI (US); Michael Sibley Carter, Austin, TX (US); Brent E. Skaw, Marquette, MI (US)

(73) Assignee: XTANT MEDICAL HOLDINGS, INC., Belgrade, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/745,132

(22) Filed: Jun. 17, 2024

(65) Prior Publication Data
US 2024/0415668 A1     Dec. 19, 2024

Related U.S. Application Data

(60) Division of application No. 17/504,239, filed on Oct. 18, 2021, which is a continuation of application No.
(Continued)

(51) Int. Cl.
A61F 2/44          (2006.01)
A61F 2/28          (2006.01)
(Continued)

(52) U.S. Cl.
CPC ............. *A61F 2/4455* (2013.01); *A61F 2/28* (2013.01); *A61F 2/30965* (2013.01);
(Continued)

(58) Field of Classification Search
CPC ...... A61F 2/4455; A61F 2/446; A61F 2/4465; A61F 2/447
See application file for complete search history.

(56) References Cited

U.S. PATENT DOCUMENTS

| | | | |
|---|---|---|---|
| 1,168,770 A | 1/1916 | Wagner | |
| 1,816,446 A | 7/1931 | Stapf | |
| (Continued) | | | |

FOREIGN PATENT DOCUMENTS

| | | | |
|---|---|---|---|
| AU | 2006200017 | 2/2006 | |
| CA | 1146301 | 5/1983 | |
| (Continued) | | | |

OTHER PUBLICATIONS

US 6,117,172 A, 09/2000, Ripamonti (withdrawn)
(Continued)

*Primary Examiner* — Ellen C Hammond
(74) *Attorney, Agent, or Firm* — Sheridan Ross P.C.

(57)          ABSTRACT

In accordance with one aspect, a spinal implant for fusing vertebral bones is provided that includes a monolithic body for being inserted between bones. The body has a through opening of the body for receiving bone growth material and a wall of the body extending about the through opening. The wall includes nubs extending into the through opening that increase the surface area of the wall available for bone on-growth.

16 Claims, 38 Drawing Sheets

Related U.S. Application Data

16/124,935, filed on Sep. 7, 2018, now Pat. No. 11,147,682.

(60) Provisional application No. 62/555,966, filed on Sep. 8, 2017.

(51) Int. Cl.
  *A61F 2/30* (2006.01)
  *A61F 2/46* (2006.01)

(52) U.S. Cl.
  CPC .............. *A61F 2/442* (2013.01); *A61F 2/447* (2013.01); *A61F 2/4611* (2013.01); *A61F 2002/2835* (2013.01); *A61F 2002/30011* (2013.01); *A61F 2002/3008* (2013.01); *A61F 2002/30148* (2013.01); *A61F 2002/30593* (2013.01); *A61F 2002/30807* (2013.01); *A61F 2002/30838* (2013.01); *A61F 2002/30843* (2013.01); *A61F 2002/30891* (2013.01); *A61F 2002/30904* (2013.01); *A61F 2002/3092* (2013.01); *A61F 2002/30985* (2013.01); *A61F 2/4603* (2013.01); *A61F 2002/4622* (2013.01); *A61F 2002/4627* (2013.01); *A61F 2220/0025* (2013.01); *A61F 2310/00023* (2013.01)

(56) References Cited

U.S. PATENT DOCUMENTS

| | | |
|---|---|---|
| 3,196,463 A | 7/1965 | Farneth |
| 3,413,741 A | 12/1968 | Fagan et al. |
| 3,648,691 A | 3/1972 | Lumb et al. |
| 3,707,107 A | 12/1972 | Bier |
| 3,739,684 A | 6/1973 | Vitkevich |
| 3,867,728 A | 2/1975 | Stubstad et al. |
| 3,875,595 A | 4/1975 | Froning et al. |
| 3,969,773 A | 7/1976 | Menschik |
| 3,975,778 A | 8/1976 | Newton, III |
| 4,021,382 A | 5/1977 | Stoy et al. |
| 4,081,402 A | 3/1978 | Levy et al. |
| 4,147,764 A | 4/1979 | Levy et al. |
| 4,309,777 A | 1/1982 | Patil |
| 4,349,921 A | 9/1982 | Kuntz |
| 4,374,523 A | 2/1983 | Yoon |
| 4,401,112 A | 8/1983 | Rezaian |
| 4,454,612 A | 6/1984 | McDaniel et al. |
| 4,566,466 A | 1/1986 | Ripple et al. |
| 4,569,338 A | 2/1986 | Edwards |
| 4,629,464 A | 12/1986 | Takata et al. |
| 4,636,217 A | 1/1987 | Ogilvie et al. |
| 4,650,490 A | 3/1987 | Figgie, III |
| 4,657,550 A | 4/1987 | Daher |
| 4,696,290 A | 9/1987 | Steffee |
| 4,714,469 A | 12/1987 | Kenna |
| 4,717,556 A | 1/1988 | Kawamura et al. |
| 4,728,561 A | 3/1988 | Crocker |
| 4,759,766 A | 7/1988 | Buettner-Janz et al. |
| 4,759,769 A | 7/1988 | Hedman |
| 4,798,585 A | 1/1989 | Inoue |
| 4,799,372 A | 1/1989 | Marcon |
| 4,800,874 A | 1/1989 | David |
| 4,834,757 A | 5/1989 | Brantigan |
| 4,863,476 A | 9/1989 | Shepperd |
| 4,863,477 A | 9/1989 | Monson |
| 4,865,603 A | 9/1989 | Noiles |
| 4,878,914 A | 11/1989 | Miwa |
| 4,878,915 A | 11/1989 | Brantigan |
| 4,899,761 A | 2/1990 | Brown et al. |
| 4,917,704 A | 4/1990 | Frey et al. |
| 4,932,969 A | 6/1990 | Frey et al. |
| 4,932,975 A | 6/1990 | Main |
| 4,936,848 A | 6/1990 | Bagby |
| 4,946,378 A | 8/1990 | Hirayama |
| 4,997,432 A | 3/1991 | Keller |

| | | |
|---|---|---|
| 5,002,576 A | 3/1991 | Fuhrmann et al. |
| 5,011,495 A | 4/1991 | Hollinger |
| 5,034,011 A | 7/1991 | Howland |
| 5,035,716 A | 7/1991 | Downey |
| 5,047,055 A | 9/1991 | Bao et al. |
| 5,059,193 A | 10/1991 | Kuslich |
| 5,071,437 A | 12/1991 | Steffee |
| 5,084,057 A | 1/1992 | Green |
| 5,108,399 A | 4/1992 | Eitenmuller et al. |
| 5,108,438 A | 4/1992 | Stone |
| 5,123,926 A | 6/1992 | Pisharodi |
| 5,127,920 A | 7/1992 | MacArthur |
| 5,133,759 A | 7/1992 | Turner |
| 5,133,772 A | 7/1992 | Hack et al. |
| 5,137,534 A | 8/1992 | Sumita |
| 5,147,404 A | 9/1992 | Downey |
| 5,152,791 A | 10/1992 | Hakamatsuka et al. |
| 5,171,278 A | 12/1992 | Pisharodi |
| 5,171,281 A | 12/1992 | Parsons et al. |
| 5,171,327 A | 12/1992 | Koch et al. |
| 5,176,710 A | 1/1993 | Hahn et al. |
| 5,185,177 A | 2/1993 | Kijima et al. |
| 5,192,326 A | 3/1993 | Bao et al. |
| 5,213,112 A | 5/1993 | Niwa et al. |
| 5,258,031 A | 11/1993 | Salib et al. |
| 5,258,043 A | 11/1993 | Stone |
| 5,269,809 A | 12/1993 | Hayhurst et al. |
| 5,271,385 A | 12/1993 | Bailey |
| 5,273,742 A | 12/1993 | Gould et al. |
| 5,275,600 A | 1/1994 | Allard |
| 5,300,073 A | 4/1994 | Ray et al. |
| 5,306,307 A | 4/1994 | Senter et al. |
| 5,306,308 A | 4/1994 | Gross et al. |
| 5,306,309 A | 4/1994 | Wagner et al. |
| 5,314,477 A | 5/1994 | Marnay |
| 5,320,625 A | 6/1994 | Bertin |
| 5,320,644 A | 6/1994 | Baumgartner |
| 5,322,675 A | 6/1994 | Hakamatsuka et al. |
| 5,334,205 A | 8/1994 | Cain |
| 5,370,697 A | 12/1994 | Baumgartner |
| 5,401,269 A | 3/1995 | Buttner-Janz et al. |
| 5,425,772 A | 6/1995 | Brantigan |
| 5,425,773 A | 6/1995 | Boyd et al. |
| 5,443,512 A | 8/1995 | Parr et al. |
| 5,443,514 A | 8/1995 | Steffee |
| 5,458,642 A | 10/1995 | Beer et al. |
| 5,458,643 A | 10/1995 | Oka et al. |
| 5,462,362 A | 10/1995 | Yuhta et al. |
| 5,474,558 A | 12/1995 | Neubardt |
| 5,480,449 A | 1/1996 | Hamilton et al. |
| 5,496,318 A | 3/1996 | Howland |
| 5,507,816 A | 4/1996 | Bullivant |
| 5,514,180 A | 5/1996 | Heggeness et al. |
| 5,519,982 A | 5/1996 | Herber et al. |
| 5,522,894 A | 6/1996 | Draenert |
| 5,522,899 A | 6/1996 | Michelson |
| 5,525,363 A | 6/1996 | Herber et al. |
| 5,531,794 A | 7/1996 | Takagi |
| 5,534,028 A | 7/1996 | Bao et al. |
| 5,534,031 A | 7/1996 | Matsuzaki et al. |
| 5,542,949 A | 8/1996 | Yoon |
| 5,549,679 A | 8/1996 | Kuslich |
| 5,556,431 A | 9/1996 | Buttner-Janz et al. |
| 5,556,433 A | 9/1996 | Gabriel et al. |
| 5,562,736 A | 10/1996 | Ray |
| 5,562,738 A | 10/1996 | Boyd et al. |
| 5,569,442 A | 10/1996 | Fulmer et al. |
| 5,571,189 A | 11/1996 | Kuslich |
| 5,571,493 A | 11/1996 | Fulmer et al. |
| 5,593,409 A | 1/1997 | Michelson |
| 5,595,563 A | 1/1997 | Moisdon |
| 5,595,703 A | 1/1997 | Swaelens et al. |
| 5,597,379 A | 1/1997 | Haines et al. |
| 5,609,635 A | 3/1997 | Michelson |
| 5,609,636 A | 3/1997 | Kohrs et al. |
| 5,609,643 A | 3/1997 | Colleran et al. |
| 5,614,205 A | 3/1997 | Usala |
| 5,634,926 A | 6/1997 | Jobe et al. |
| 5,643,264 A | 7/1997 | Sherman et al. |

(56)                References Cited

U.S. PATENT DOCUMENTS

| | | | |
|---|---|---|---|
| 5,645,596 A | 7/1997 | Kim et al. |
| 5,645,597 A | 7/1997 | Krapiva |
| 5,645,598 A | 7/1997 | Brosnahan, III et al. |
| 5,645,599 A | 7/1997 | Samant |
| 5,653,762 A | 8/1997 | Pisharodi |
| 5,658,332 A | 8/1997 | Ducheyne et al. |
| 5,658,336 A | 8/1997 | Pisharodi |
| 5,658,337 A | 8/1997 | Kohrs et al. |
| 5,665,122 A | 9/1997 | Kambin |
| 5,669,909 A | 9/1997 | Zdeblick et al. |
| 5,674,295 A | 10/1997 | Ray |
| 5,674,296 A | 10/1997 | Bryan et al. |
| 5,676,701 A | 10/1997 | Yuan |
| 5,676,702 A | 10/1997 | Ratron |
| 5,676,976 A | 10/1997 | Lee et al. |
| 5,681,316 A | 10/1997 | DeOrio et al. |
| 5,681,872 A | 10/1997 | Erbe |
| 5,683,465 A | 11/1997 | Shinn |
| 5,683,667 A | 11/1997 | Fulmer et al. |
| 5,693,100 A | 12/1997 | Pisharodi |
| 5,702,449 A | 12/1997 | McKay |
| 5,702,450 A | 12/1997 | Bisserie |
| 5,702,451 A | 12/1997 | Biedermann et al. |
| 5,713,899 A | 2/1998 | Marnay et al. |
| 5,713,904 A | 2/1998 | Errico et al. |
| 5,716,415 A | 2/1998 | Steffee |
| 5,716,416 A | 2/1998 | Lin |
| 5,728,762 A | 3/1998 | Reich |
| 5,733,286 A | 3/1998 | Errico et al. |
| 5,755,797 A | 5/1998 | Baumgartner |
| 5,755,798 A | 5/1998 | Papavero |
| 5,766,252 A | 6/1998 | Henry et al. |
| 5,772,661 A | 6/1998 | Michelson |
| 5,776,198 A | 7/1998 | Rabbe |
| 5,776,199 A | 7/1998 | Michelson |
| 5,782,832 A | 7/1998 | Arsen et al. |
| 5,782,971 A | 7/1998 | Constantz et al. |
| 5,783,217 A | 7/1998 | Lee et al. |
| 5,786,134 A | 7/1998 | Nair et al. |
| 5,797,909 A | 8/1998 | Michelson |
| 5,797,963 A | 8/1998 | McDevitt |
| 5,800,547 A | 9/1998 | Schaeffer |
| 5,820,632 A | 10/1998 | Constantz et al. |
| 5,824,093 A | 10/1998 | Ray |
| 5,824,094 A | 10/1998 | Serhan |
| 5,824,331 A | 10/1998 | Usala |
| 5,836,948 A | 11/1998 | Zucherman et al. |
| 5,860,973 A | 1/1999 | Michelson |
| 5,860,977 A | 1/1999 | Zucherman et al. |
| 5,860,980 A | 1/1999 | Axelson, Jr. et al. |
| 5,865,845 A | 2/1999 | Thalgott |
| 5,865,846 A | 2/1999 | Bryan et al. |
| 5,876,404 A | 3/1999 | Zucherman et al. |
| 5,885,299 A | 3/1999 | Winslow et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,893,889 A | 4/1999 | Harrington |
| 5,893,890 A | 4/1999 | Pisharodi |
| 5,895,428 A | 4/1999 | Berry |
| 5,899,941 A | 5/1999 | Nishijima et al. |
| 5,914,356 A | 6/1999 | Erbe |
| 5,919,235 A | 7/1999 | Husson et al. |
| 5,922,339 A | 7/1999 | Usala |
| 5,931,777 A | 8/1999 | Sava |
| 5,939,039 A | 8/1999 | Sapieszko |
| 5,943,235 A | 8/1999 | Earl et al. |
| 5,964,807 A | 10/1999 | Gan et al. |
| 5,968,098 A | 10/1999 | Winslow |
| 5,969,020 A | 10/1999 | Shalaby |
| 5,972,031 A | 10/1999 | Biedermann et al. |
| 5,976,186 A | 11/1999 | Bao et al. |
| 5,980,572 A | 11/1999 | Kim et al. |
| 5,984,967 A | 11/1999 | Zdeblick et al. |
| 5,989,289 A | 11/1999 | Coates et al. |
| 6,001,130 A | 12/1999 | Bryan et al. |
| 6,004,326 A | 12/1999 | Castro et al. |
| 6,010,502 A | 1/2000 | Bagby |
| 6,013,591 A | 1/2000 | Ying |
| 6,019,793 A | 2/2000 | Perren |
| 6,022,376 A | 2/2000 | Assell et al. |
| 6,022,377 A | 2/2000 | Nuelle et al. |
| 6,025,538 A | 2/2000 | Yaccarino, III |
| 6,027,742 A | 2/2000 | Lee et al. |
| 6,037,519 A | 3/2000 | McKay |
| 6,039,761 A | 3/2000 | Li et al. |
| 6,039,762 A | 3/2000 | McKay |
| 6,039,763 A | 3/2000 | Shelokov |
| 6,042,582 A | 3/2000 | Ray |
| 6,048,342 A | 4/2000 | Zucherman et al. |
| 6,053,916 A | 4/2000 | Moore |
| 6,059,829 A | 5/2000 | Schlapfer et al. |
| 6,063,088 A | 5/2000 | Winslow |
| 6,066,175 A | 5/2000 | Henderson et al. |
| 6,068,630 A | 5/2000 | Zucherman et al. |
| 6,068,974 A | 5/2000 | Klann |
| RE36,758 E | 6/2000 | Fitz |
| 6,074,390 A | 6/2000 | Zucherman et al. |
| 6,080,155 A | 6/2000 | Michelson |
| 6,080,158 A | 6/2000 | Lin |
| 6,090,112 A | 7/2000 | Zucherman et al. |
| 6,093,205 A | 7/2000 | McLeod |
| 6,093,207 A | 7/2000 | Pisharodi |
| 6,096,038 A | 8/2000 | Michelson |
| 6,096,039 A | 8/2000 | Stoltenberg et al. |
| 6,110,210 A | 8/2000 | Norton et al. |
| 6,113,639 A | 9/2000 | Ray |
| 6,117,456 A | 9/2000 | Lee et al. |
| 6,127,597 A | 10/2000 | Beyar et al. |
| 6,129,730 A | 10/2000 | Bono et al. |
| 6,132,465 A | 10/2000 | Ray |
| 6,136,031 A | 10/2000 | Middleton |
| 6,139,548 A | 10/2000 | Errico |
| 6,139,579 A | 10/2000 | Steffee |
| 6,143,031 A | 11/2000 | Knothe et al. |
| 6,143,033 A | 11/2000 | Paul |
| 6,146,421 A | 11/2000 | Gordon et al. |
| 6,146,422 A | 11/2000 | Lawson |
| 6,149,652 A | 11/2000 | Zucherman et al. |
| 6,149,688 A | 11/2000 | Brosnahan et al. |
| 6,152,926 A | 11/2000 | Zucherman et al. |
| RE37,005 E | 12/2000 | Michelson |
| 6,156,038 A | 12/2000 | Zucherman et al. |
| 6,156,067 A | 12/2000 | Bryan et al. |
| 6,162,252 A | 12/2000 | Kuras |
| 6,179,874 B1 | 1/2001 | Cauthen |
| 6,183,471 B1 | 2/2001 | Zucherman et al. |
| 6,183,518 B1 | 2/2001 | Ross |
| 6,187,046 B1 | 2/2001 | Yamamoto |
| 6,187,048 B1 | 2/2001 | Milner |
| 6,190,387 B1 | 2/2001 | Zucherman et al. |
| 6,190,414 B1 | 2/2001 | Young |
| 6,193,756 B1 | 2/2001 | Studer et al. |
| 6,193,757 B1 | 2/2001 | Foley et al. |
| 6,206,924 B1 | 3/2001 | Timm |
| 6,207,216 B1 | 3/2001 | Layrolle et al. |
| 6,210,422 B1 | 4/2001 | Douglas |
| 6,210,442 B1 | 4/2001 | Wing |
| 6,214,368 B1 | 4/2001 | Lee et al. |
| 6,224,607 B1 | 5/2001 | Michelson |
| 6,224,630 B1 | 5/2001 | Bao et al. |
| 6,231,881 B1 | 5/2001 | Usala |
| 6,235,030 B1 | 5/2001 | Zucherman et al. |
| 6,238,397 B1 | 5/2001 | Zucherman et al. |
| 6,240,926 B1 | 6/2001 | Chin Gan et al. |
| 6,245,108 B1 | 6/2001 | Biscup |
| 6,251,140 B1 | 6/2001 | Marino et al. |
| 6,261,587 B1 | 7/2001 | Usala |
| 6,264,695 B1 | 7/2001 | Stoy |
| 6,270,498 B1 | 8/2001 | Michelson |
| 6,270,977 B1 | 8/2001 | Klann |
| 6,277,149 B1 | 8/2001 | Boyle et al. |
| 6,280,444 B1 | 8/2001 | Zucherman et al. |

(56)                References Cited

U.S. PATENT DOCUMENTS

| | | | |
|---|---|---|---|
| 6,280,475 | B1 | 8/2001 | Bao et al. |
| 6,280,478 | B1 | 8/2001 | Richter |
| 6,283,968 | B1 | 9/2001 | Mehdizadeh |
| 6,283,998 | B1 | 9/2001 | Eaton |
| 6,287,341 | B1 | 9/2001 | Lee et al. |
| 6,290,724 | B1 | 9/2001 | Marino |
| 6,296,665 | B1 | 10/2001 | Strad et al. |
| 6,302,913 | B1 | 10/2001 | Ripamonti |
| 6,309,400 | B2 | 10/2001 | Beaupre |
| 6,312,472 | B1 | 11/2001 | Hall et al. |
| 6,315,795 | B1 | 11/2001 | Scarborough |
| 6,315,797 | B1 | 11/2001 | Middleton |
| 6,315,994 | B2 | 11/2001 | Usala |
| 6,332,882 | B1 | 12/2001 | Zucherman et al. |
| 6,332,883 | B1 | 12/2001 | Zucherman et al. |
| 6,342,055 | B1 | 1/2002 | Eisermann et al. |
| 6,344,061 | B1 | 2/2002 | Leitao et al. |
| 6,346,123 | B1 | 2/2002 | McKay |
| 6,348,071 | B1 | 2/2002 | Steffee |
| 6,350,462 | B1 | 2/2002 | Hakamatsuka et al. |
| 6,352,557 | B1 | 3/2002 | Ferree |
| 6,352,707 | B1 | 3/2002 | Usala |
| 6,364,883 | B1 | 4/2002 | Santilli |
| 6,368,350 | B1 | 4/2002 | Erickson et al. |
| 6,371,987 | B1 | 4/2002 | Weiland et al. |
| 6,371,990 | B1 | 4/2002 | Ferree |
| 6,375,682 | B1 | 4/2002 | Fleischmann et al. |
| 6,379,355 | B1 | 4/2002 | Zucherman et al. |
| 6,391,058 | B1 | 5/2002 | Kuslich et al. |
| 6,395,031 | B1 | 5/2002 | Foley et al. |
| 6,395,032 | B1 | 5/2002 | Gauchet |
| 6,402,784 | B1 | 6/2002 | Wardlaw |
| 6,402,785 | B1 | 6/2002 | Zdeblick et al. |
| 6,419,676 | B1 | 7/2002 | Zucherman et al. |
| 6,419,677 | B2 | 7/2002 | Zucherman et al. |
| 6,419,704 | B1 | 7/2002 | Ferree |
| 6,428,544 | B1 | 8/2002 | Ralph |
| 6,428,575 | B2 | 8/2002 | Koo et al. |
| 6,428,579 | B1 | 8/2002 | Valentini |
| 6,432,106 | B1 | 8/2002 | Fraser |
| 6,432,107 | B1 | 8/2002 | Ferree |
| 6,432,140 | B1 | 8/2002 | Lin |
| 6,436,098 | B1 | 8/2002 | Michelson |
| 6,436,101 | B1 | 8/2002 | Hamada |
| 6,436,102 | B1 | 8/2002 | Ralph |
| 6,436,140 | B1 | 8/2002 | Liu et al. |
| 6,436,141 | B2 | 8/2002 | Castro et al. |
| 6,436,142 | B1 | 8/2002 | Paes et al. |
| 6,436,146 | B1 | 8/2002 | Hassler et al. |
| 6,440,168 | B1 | 8/2002 | Cauthen |
| 6,440,170 | B1 | 8/2002 | Jackson |
| 6,441,073 | B1 | 8/2002 | Tanaka |
| 6,451,019 | B1 | 9/2002 | Zucherman et al. |
| 6,451,020 | B1 | 9/2002 | Zucherman et al. |
| 6,454,806 | B1 | 9/2002 | Cohen et al. |
| 6,458,159 | B1 | 10/2002 | Thalgott |
| 6,458,162 | B1 | 10/2002 | Koblish et al. |
| 6,478,796 | B2 | 11/2002 | Zucherman et al. |
| 6,478,801 | B1 | 11/2002 | Ralph |
| 6,478,822 | B1 | 11/2002 | Leroux et al. |
| 6,478,823 | B1 | 11/2002 | Michelson |
| 6,482,233 | B1 | 11/2002 | Aebi |
| 6,488,716 | B1 | 12/2002 | Huang et al. |
| 6,500,132 | B1 | 12/2002 | Li |
| 6,500,178 | B2 | 12/2002 | Zucherman et al. |
| 6,500,549 | B1 | 12/2002 | Deppisch et al. |
| 6,503,279 | B1 | 1/2003 | Webb |
| 6,508,839 | B1 | 1/2003 | Lambrecht et al. |
| 6,514,256 | B2 | 2/2003 | Zucherman et al. |
| 6,517,580 | B1 | 2/2003 | Ramadan |
| 6,520,993 | B2 | 2/2003 | James et al. |
| 6,520,996 | B1 | 2/2003 | Manasas et al. |
| 6,524,341 | B2 | 2/2003 | Lang et al. |
| 6,527,803 | B1 | 3/2003 | Crozet et al. |
| 6,527,804 | B1 | 3/2003 | Gauchet et al. |
| 6,527,810 | B2 | 3/2003 | Johnson et al. |
| 6,530,955 | B2 | 3/2003 | Boyle et al. |
| 6,530,956 | B1 | 3/2003 | Mansmann |
| 6,533,786 | B1 | 3/2003 | Needham |
| 6,533,799 | B1 | 3/2003 | Bouchier |
| 6,537,320 | B1 | 3/2003 | Michelson |
| 6,540,785 | B1 | 4/2003 | Gill et al. |
| 6,547,823 | B2 | 4/2003 | Scarborough |
| 6,558,424 | B2 | 5/2003 | Thalgott |
| 6,562,047 | B2 | 5/2003 | Ralph |
| 6,565,566 | B1 | 5/2003 | Wagner et al. |
| 6,569,396 | B1 | 5/2003 | Yanagi |
| 6,575,975 | B2 | 6/2003 | Brace et al. |
| 6,579,318 | B2 | 6/2003 | Varga |
| 6,579,320 | B1 | 6/2003 | Gauchet et al. |
| 6,579,321 | B1 | 6/2003 | Gordon et al. |
| 6,582,453 | B1 | 6/2003 | Tran |
| 6,582,466 | B1 | 6/2003 | Gauchet |
| 6,592,624 | B1 | 7/2003 | Fraser et al. |
| 6,602,291 | B1 | 8/2003 | Ray et al. |
| 6,607,559 | B2 | 8/2003 | Ralph |
| 6,610,089 | B1 | 8/2003 | Liu et al. |
| 6,610,091 | B1 | 8/2003 | Reiley |
| 6,610,093 | B1 | 8/2003 | Pisharod |
| 6,620,091 | B1 | 9/2003 | Zavell et al. |
| 6,626,944 | B1 | 9/2003 | Taylor |
| 6,635,059 | B2 | 10/2003 | Randall et al. |
| 6,641,614 | B1 | 11/2003 | Wagner et al. |
| 6,648,903 | B1 | 11/2003 | Pierson |
| 6,652,533 | B2 | 11/2003 | O'Neil |
| 6,669,697 | B1 | 12/2003 | Pisharodi |
| 6,669,730 | B2 | 12/2003 | Ralph |
| 6,673,075 | B2 | 1/2004 | Santilli |
| 6,673,113 | B2 | 1/2004 | Ralph |
| 6,676,703 | B2 | 1/2004 | Biscup |
| 6,679,915 | B1 | 1/2004 | Cauthen |
| 6,682,562 | B2 | 1/2004 | Viart |
| 6,689,165 | B2 | 2/2004 | Jacob et al. |
| 6,699,246 | B2 | 3/2004 | Zucherman et al. |
| 6,699,247 | B2 | 3/2004 | Zucherman et al. |
| 6,713,079 | B2 | 3/2004 | Usala |
| 6,716,247 | B2 | 4/2004 | Michelson |
| 6,719,794 | B2 | 4/2004 | Gerber et al. |
| 6,730,127 | B2 | 5/2004 | Michelson |
| 6,730,315 | B2 | 5/2004 | Usala |
| 6,733,531 | B1 | 5/2004 | Trieu |
| 6,733,535 | B2 | 5/2004 | Michelson |
| 6,736,817 | B2 | 5/2004 | Troxell |
| 6,743,257 | B2 | 6/2004 | Castro et al. |
| 6,746,484 | B1 | 6/2004 | Liu et al. |
| 6,758,849 | B1 | 7/2004 | Michelson |
| 6,758,862 | B2 | 7/2004 | Berry |
| 6,767,367 | B1 | 7/2004 | Michelson |
| 6,770,074 | B2 | 8/2004 | Michelson |
| 6,770,095 | B2 | 8/2004 | Grinberg et al. |
| 6,770,096 | B2 | 8/2004 | Bolger et al. |
| 6,776,860 | B2 | 8/2004 | Aral et al. |
| 6,783,550 | B2 | 8/2004 | MacArthur |
| 6,790,455 | B2 | 9/2004 | Chu et al. |
| 6,793,678 | B2 | 9/2004 | Hawkins |
| 6,796,983 | B1 | 9/2004 | Zucherman et al. |
| 6,824,565 | B2 | 11/2004 | Muhanna |
| 6,827,740 | B1 | 12/2004 | Michelson |
| 6,830,570 | B1 | 12/2004 | Frey et al. |
| 6,833,006 | B2 | 12/2004 | Foley et al. |
| 6,835,206 | B2 | 12/2004 | Jackson |
| 6,840,961 | B2 | 1/2005 | Tofighi |
| 6,841,255 | B2 | 1/2005 | Deppisch et al. |
| 6,843,805 | B2 | 1/2005 | Webb |
| 6,846,327 | B2 | 1/2005 | Khandkar |
| 6,855,167 | B2 | 2/2005 | Shimp et al. |
| 6,858,041 | B2 | 2/2005 | Richter |
| 6,863,689 | B2 | 3/2005 | Ralph |
| 6,872,208 | B1 | 3/2005 | McBride et al. |
| 6,887,272 | B2 | 5/2005 | Shinomiya |
| 6,890,355 | B2 | 5/2005 | Michelson |
| 6,893,464 | B2 | 5/2005 | Kiester |
| 6,899,716 | B2 | 5/2005 | Cragg |
| 6,905,512 | B2 | 6/2005 | Paes et al. |

(56)　　　　　References Cited

U.S. PATENT DOCUMENTS

| | | |
|---|---|---|
| 6,923,810 B1 | 8/2005 | Michelson |
| 6,923,830 B2 | 8/2005 | Michelson |
| 6,926,737 B2 | 8/2005 | Jackson |
| 6,936,071 B1 | 8/2005 | Marnay et al. |
| 6,942,670 B2 | 9/2005 | Heldreth et al. |
| 6,942,698 B1 | 9/2005 | Jackson |
| 6,949,251 B2 | 9/2005 | Dalal et al. |
| 6,951,561 B2 | 10/2005 | Warren et al. |
| 6,964,687 B1 | 11/2005 | Bernard et al. |
| 6,966,931 B2 | 11/2005 | Huang |
| 6,974,479 B2 | 12/2005 | Trieu |
| 6,974,480 B2 | 12/2005 | Messerli |
| 6,979,353 B2 | 12/2005 | Bresina |
| 6,981,975 B2 | 1/2006 | Michelson |
| 6,984,246 B2 | 1/2006 | Huang |
| 6,986,789 B2 | 1/2006 | Schultz |
| 6,987,136 B2 | 1/2006 | Erbe |
| 6,991,653 B2 | 1/2006 | White |
| 6,991,654 B2 | 1/2006 | Foley |
| 7,001,433 B2 | 2/2006 | Songer |
| 7,018,416 B2 | 3/2006 | Hanson et al. |
| 7,033,393 B2 | 4/2006 | Gainor et al. |
| 7,033,394 B2 | 4/2006 | Michelson |
| 7,041,137 B2 | 5/2006 | Fulton et al. |
| 7,041,138 B2 | 5/2006 | Lange et al. |
| 7,044,972 B2 | 5/2006 | Mathys, Jr. et al. |
| 7,056,341 B2 | 6/2006 | Crozet et al. |
| 7,060,073 B2 | 6/2006 | Frey et al. |
| 7,063,725 B2 | 6/2006 | Foley |
| RE39,196 E | 7/2006 | Ying |
| 7,074,240 B2 | 7/2006 | Pisharod |
| 7,083,749 B2 | 8/2006 | Lin et al. |
| 7,087,540 B2 | 8/2006 | Heide et al. |
| 7,101,375 B2 | 9/2006 | Zucherman et al. |
| 7,118,598 B2 | 10/2006 | Michelson |
| 7,122,057 B2 | 10/2006 | Beam et al. |
| 7,125,425 B2 | 10/2006 | Foley et al. |
| 7,135,042 B2 | 11/2006 | Stoll |
| 7,137,997 B2 | 11/2006 | Paul |
| 7,141,068 B2 | 11/2006 | Ross |
| 7,156,874 B2 | 1/2007 | Paponneau et al. |
| 7,156,876 B2 | 1/2007 | Moumene |
| 7,169,183 B2 | 1/2007 | Liu et al. |
| 7,172,627 B2 | 2/2007 | Fiere et al. |
| 7,201,751 B2 | 4/2007 | Zucherman et al. |
| 7,217,293 B2 | 5/2007 | Branch, Jr. |
| 7,223,289 B2 | 5/2007 | Trieu |
| 7,226,480 B2 | 6/2007 | Thalgott |
| 7,230,039 B2 | 6/2007 | Trieu |
| 7,235,079 B2 | 6/2007 | Jensen et al. |
| 7,238,203 B2 | 7/2007 | Bagga et al. |
| 7,238,206 B2 | 7/2007 | Lange et al. |
| 7,261,505 B2 | 8/2007 | Ernst et al. |
| 7,264,621 B2 | 9/2007 | Coates et al. |
| D553,742 S | 10/2007 | Park |
| D553,743 S | 10/2007 | Park |
| D553,744 S | 10/2007 | Park |
| D553,745 S | 10/2007 | Park |
| 7,303,583 B1 | 12/2007 | Schar |
| 7,318,841 B2 | 1/2008 | Tofight |
| 7,326,251 B2 | 2/2008 | McCombe et al. |
| 7,338,525 B2 | 3/2008 | Ferree |
| D566,276 S | 4/2008 | Blain |
| 7,445,634 B2 | 11/2008 | Trieu |
| 7,445,637 B2 | 11/2008 | Taylor |
| 7,455,692 B2 | 11/2008 | Michelson |
| 7,479,160 B2 | 1/2009 | Branch et al. |
| 7,500,978 B2 | 3/2009 | Gorensek et al. |
| 7,509,183 B2 | 3/2009 | Lin et al. |
| 7,527,803 B2 | 5/2009 | Park |
| 7,537,616 B1 | 5/2009 | Branch et al. |
| 7,618,458 B2 | 11/2009 | Biedermann et al. |
| 7,622,129 B1 | 11/2009 | Haberstroh et al. |
| 7,641,690 B2 | 1/2010 | Abdou |
| 7,648,509 B2 | 1/2010 | Stark |
| 7,662,182 B2 | 2/2010 | Zubok et al. |
| 7,662,186 B2 | 2/2010 | Bagga et al. |
| 7,665,979 B2 | 2/2010 | Heugel |
| 7,682,397 B2 | 3/2010 | Berry et al. |
| 7,717,958 B2 | 5/2010 | Cragg et al. |
| 7,763,078 B2 | 7/2010 | Peterman |
| RE41,584 E | 8/2010 | Ying |
| 7,776,095 B2 | 8/2010 | Peterman |
| 7,794,465 B2 | 9/2010 | Marik et al. |
| 7,806,911 B2 | 10/2010 | Peckham |
| 7,819,920 B2 | 10/2010 | Assaker |
| 7,824,427 B2 | 11/2010 | Perez-Cruet |
| 7,833,246 B2 | 11/2010 | Mitchell |
| 7,833,283 B2 | 11/2010 | Webster |
| 7,837,732 B2 | 11/2010 | Zucherman et al. |
| 7,842,071 B2 | 11/2010 | Hawkes |
| 7,846,210 B2 | 12/2010 | Perez-Cruet |
| 7,850,732 B2 | 12/2010 | Heinz |
| 7,850,736 B2 | 12/2010 | Heinz |
| 7,857,840 B2 | 12/2010 | Krebs et al. |
| 7,875,080 B2 | 1/2011 | Puno |
| 7,879,104 B2 | 2/2011 | Dewey et al. |
| 7,883,542 B2 | 2/2011 | Zipnick |
| 7,892,239 B2 | 2/2011 | Warnick |
| 7,901,458 B2 | 3/2011 | DeRidder et al. |
| 7,909,859 B2 | 3/2011 | Mosca |
| 7,909,871 B2 | 3/2011 | Abdou |
| 7,909,872 B2 | 3/2011 | Zipnick et al. |
| 7,914,554 B2 | 3/2011 | Michelson |
| 7,918,876 B2 | 4/2011 | Mueller |
| 7,918,891 B1 | 4/2011 | Curran et al. |
| 7,922,765 B2 | 4/2011 | Reiley |
| 7,938,834 B2 | 5/2011 | Roush |
| 7,951,203 B2 | 5/2011 | McCombe et al. |
| 7,976,550 B2 | 7/2011 | Trudeau |
| 7,988,708 B2 | 8/2011 | Yeh |
| 7,988,734 B2 | 8/2011 | Peterman |
| 8,002,831 B2 | 8/2011 | Burd et al. |
| 8,002,837 B2 | 8/2011 | Stream |
| 8,012,156 B2 | 9/2011 | Alvarez |
| 8,012,208 B2 | 9/2011 | Lechmann et al. |
| 8,025,678 B2 | 9/2011 | Reynolds |
| 8,029,755 B2 | 10/2011 | Ahn |
| 8,038,678 B2 | 10/2011 | Schmieding et al. |
| 8,043,293 B2 | 10/2011 | Warnick |
| 8,062,375 B2 | 11/2011 | Glerum et al. |
| 8,083,799 B2 | 12/2011 | Baynham et al. |
| 8,105,382 B2 | 1/2012 | Olmos et al. |
| 8,118,872 B2 | 2/2012 | Trudeau |
| 8,128,856 B2 | 3/2012 | Chou |
| 8,133,232 B2 | 3/2012 | Levy et al. |
| 8,137,402 B2 | 3/2012 | Eckman |
| 8,142,508 B1 | 3/2012 | Bruffey et al. |
| 8,157,845 B2 | 4/2012 | Warnick |
| 8,163,026 B2 | 4/2012 | Gray |
| 8,172,877 B2 | 5/2012 | Winslow et al. |
| 8,172,905 B2 | 5/2012 | Baynham et al. |
| 8,187,334 B2 | 5/2012 | Curran et al. |
| 8,192,356 B2 | 6/2012 | Miles |
| 8,192,357 B2 | 6/2012 | Miles |
| D664,252 S | 7/2012 | Weiland et al. |
| 8,216,316 B2 | 7/2012 | Kirschman |
| 8,221,479 B2 | 7/2012 | Glazer et al. |
| 8,241,359 B2 | 8/2012 | Davis et al. |
| 8,241,360 B2 | 8/2012 | Bao et al. |
| 8,246,655 B2 | 8/2012 | Jackson et al. |
| 8,246,686 B1 | 8/2012 | Curran et al. |
| 8,262,701 B2 | 9/2012 | Rathbun |
| 8,262,731 B2 | 9/2012 | Songer |
| 8,262,737 B2 | 9/2012 | Bagga et al. |
| 8,275,594 B2 | 9/2012 | Lin et al. |
| 8,287,541 B2 | 10/2012 | Nelson et al. |
| 8,303,660 B1 | 11/2012 | Abdou |
| 8,308,767 B2 | 11/2012 | Hochschuler et al. |
| 8,308,805 B2 | 11/2012 | Lynn et al. |
| 8,343,224 B2 | 1/2013 | Lynn et al. |
| 8,361,156 B2 | 1/2013 | Curran et al. |
| 8,372,084 B2 | 2/2013 | Pernsteiner |
| 8,388,684 B2 | 3/2013 | Bao et al. |

(56) References Cited

U.S. PATENT DOCUMENTS

| | | |
|---|---|---|
| 8,403,986 B2 | 3/2013 | Michelson |
| 8,409,213 B2 | 4/2013 | Trudeau |
| 8,409,290 B2 | 4/2013 | Zamani et al. |
| 8,425,529 B2 | 4/2013 | Milz et al. |
| 8,425,559 B2 | 4/2013 | Tebbe |
| 8,425,610 B2 | 4/2013 | Guyer et al. |
| 8,439,977 B2 | 5/2013 | Ksotuik et al. |
| 8,444,650 B2 | 5/2013 | Warnick |
| 8,449,583 B2 | 5/2013 | Krebs et al. |
| 8,449,585 B2 | 5/2013 | Wallenstein et al. |
| 8,480,749 B2 | 7/2013 | Ullrich, Jr. et al. |
| 8,486,147 B2 | 7/2013 | De Villiers et al. |
| 8,486,149 B2 | 7/2013 | Saidha |
| 8,496,710 B2 | 7/2013 | Bagga et al. |
| 8,498,710 B2 | 7/2013 | Walker et al. |
| 8,540,769 B2 | 9/2013 | Janowski et al. |
| 8,562,684 B2 | 10/2013 | Ullrich, Jr. et al. |
| 8,585,761 B2 | 11/2013 | Theofilos |
| 8,585,766 B2 | 11/2013 | Ullrich, Jr. et al. |
| 8,585,767 B2 | 11/2013 | Ullrich, Jr. et al. |
| 8,590,157 B2 | 11/2013 | Kruth et al. |
| 8,597,050 B2 | 12/2013 | Flaherty et al. |
| 8,597,357 B2 | 12/2013 | Trudeau |
| 8,597,604 B2 | 12/2013 | Ahn |
| 8,603,141 B2 | 12/2013 | Hochschuler et al. |
| 8,603,172 B2 | 12/2013 | Fuji et al. |
| 8,609,122 B2 | 12/2013 | Lamberti et al. |
| 8,617,247 B2 | 12/2013 | Lechmann et al. |
| 8,641,764 B2 | 2/2014 | Gately |
| 8,663,331 B2 | 3/2014 | McClellan, III et al. |
| 8,664,202 B2 | 3/2014 | Lamberti et al. |
| 8,669,043 B2 | 3/2014 | Mills et al. |
| 8,672,976 B2 | 3/2014 | Kilpela et al. |
| 8,673,011 B2 | 3/2014 | Theofilos et al. |
| 8,685,031 B2 | 4/2014 | Kleiner et al. |
| 8,690,917 B2 | 4/2014 | Suh et al. |
| 8,697,231 B2 | 4/2014 | Longepied et al. |
| 8,700,198 B2 | 4/2014 | Conway |
| 8,709,088 B2 | 4/2014 | Kleiner et al. |
| 8,715,350 B2 | 5/2014 | Janowski et al. |
| 8,734,521 B2 | 5/2014 | Freeman et al. |
| 8,758,409 B2 | 6/2014 | Hochschuler et al. |
| 8,758,442 B2 | 6/2014 | Ullrich, Jr. et al. |
| 8,758,443 B2 | 6/2014 | Ullrich, Jr. et al. |
| 8,784,721 B2 | 7/2014 | Philippi et al. |
| 8,801,791 B2 | 8/2014 | Soo et al. |
| 8,814,919 B2 | 8/2014 | Barrus et al. |
| 8,814,939 B2 | 8/2014 | Ullrich, Jr. et al. |
| 8,834,571 B2 | 9/2014 | Bagga et al. |
| 8,843,229 B2 | 9/2014 | Vanasse |
| 8,858,637 B2 | 10/2014 | Milz et al. |
| 8,870,957 B2 | 10/2014 | Vraney |
| 8,888,854 B2 | 11/2014 | Glerum et al. |
| 8,903,533 B2 | 12/2014 | Eggers et al. |
| 8,906,028 B2 | 12/2014 | Kleiner et al. |
| 8,932,356 B2 | 1/2015 | Kraus |
| 8,940,317 B2 | 1/2015 | Lamberti et al. |
| D723,682 S | 3/2015 | Kleiner et al. |
| 8,967,990 B2 | 3/2015 | Weidinger et al. |
| 8,992,622 B2 | 3/2015 | Ullrich, Jr. et al. |
| 8,999,711 B2 | 4/2015 | Harlow et al. |
| 9,011,546 B2 | 4/2015 | Ullrich, Jr. et al. |
| 9,011,982 B2 | 4/2015 | Muller et al. |
| 9,034,043 B2 | 5/2015 | Danacioglu et al. |
| 9,072,609 B2 | 7/2015 | Kovarik et al. |
| 9,125,756 B2 | 9/2015 | Ullrich, Jr. et al. |
| 9,132,021 B2 | 9/2015 | Mermuys |
| 9,233,011 B2 | 1/2016 | Trudeau |
| D750,249 S | 2/2016 | Grimberg, Jr. et al. |
| 9,283,078 B2 | 3/2016 | Roels et al. |
| 9,327,051 B2 | 5/2016 | Ullrich, Jr. et al. |
| 9,358,122 B2 | 6/2016 | Soo |
| 9,387,092 B2 | 7/2016 | Mermuys |
| 9,408,717 B2 | 8/2016 | Perrow |
| 9,433,511 B2 | 9/2016 | Bagga et al. |
| 9,445,914 B2 | 9/2016 | Milz et al. |
| 9,545,269 B2 | 1/2017 | Kilpela et al. |
| 9,549,822 B2 | 1/2017 | Wimberley |
| 9,561,961 B2 | 2/2017 | Capistron et al. |
| D786,434 S | 5/2017 | Trautwein |
| 9,687,359 B2 | 6/2017 | Perrow |
| 9,693,872 B2 | 7/2017 | Trudeau |
| 9,700,430 B2 | 7/2017 | Perrow |
| 9,700,431 B2 | 7/2017 | Nebosky et al. |
| 9,883,949 B2 | 2/2018 | Mermuys |
| 9,931,148 B2 | 4/2018 | Grady, Jr. et al. |
| 10,105,240 B2 | 10/2018 | DeFelice et al. |
| D833,012 S | 11/2018 | Jones |
| D833,611 S | 11/2018 | Jones |
| D833,612 S | 11/2018 | Jones |
| D835,279 S | 12/2018 | Jones |
| D835,788 S | 12/2018 | Jones |
| D840,036 S | 2/2019 | Jones |
| D907,771 S | 1/2021 | Trudeau et al. |
| 11,147,682 B2 | 10/2021 | Trudeau et al. |
| D968,613 S | 11/2022 | Trudeau et al. |
| 2001/0010021 A1 | 7/2001 | Boyd et al. |
| 2001/0012938 A1 | 8/2001 | Zucherman et al. |
| 2001/0014826 A1 | 8/2001 | Biedermann et al. |
| 2001/0016733 A1 | 8/2001 | Frey et al. |
| 2001/0016772 A1 | 8/2001 | Lee et al. |
| 2001/0016773 A1 | 8/2001 | Serhan |
| 2001/0016776 A1 | 8/2001 | Zucherman et al. |
| 2001/0020476 A1 | 9/2001 | Gan et al. |
| 2001/0027343 A1 | 10/2001 | Keller |
| 2001/0031965 A1 | 10/2001 | Zucherman et al. |
| 2001/0032019 A1 | 10/2001 | Van Dyke et al. |
| 2001/0032020 A1 | 10/2001 | Besselink |
| 2001/0047207 A1 | 11/2001 | Michelson |
| 2001/0047208 A1 | 11/2001 | Michelson |
| 2001/0049560 A1 | 12/2001 | Paul |
| 2001/0051829 A1 | 12/2001 | Middleton |
| 2002/0013600 A1 | 1/2002 | Scribiner |
| 2002/0013624 A1 | 1/2002 | Michelson |
| 2002/0022883 A1 | 2/2002 | Burg |
| 2002/0022888 A1 | 2/2002 | Serhan |
| 2002/0026244 A1 | 2/2002 | Trieu |
| 2002/0029082 A1 | 3/2002 | Muhanna |
| 2002/0029083 A1 | 3/2002 | Zucherman et al. |
| 2002/0035400 A1 | 3/2002 | Bryan et al. |
| 2002/0045942 A1 | 4/2002 | Ham |
| 2002/0045944 A1 | 4/2002 | Muhanna |
| 2002/0049447 A1 | 4/2002 | Li |
| 2002/0049498 A1 | 4/2002 | Yuksel |
| 2002/0065560 A1 | 5/2002 | Varga |
| 2002/0082608 A1 | 6/2002 | Reiley |
| 2002/0082700 A1 | 6/2002 | Biachi et al. |
| 2002/0082701 A1 | 6/2002 | Zamani et al. |
| 2002/0087212 A1 | 7/2002 | James et al. |
| 2002/0087480 A1 | 7/2002 | Sauriol |
| 2002/0091390 A1 | 7/2002 | Michelson |
| 2002/0099444 A1 | 7/2002 | Boyd et al. |
| 2002/0106393 A1 | 8/2002 | Biachi et al. |
| 2002/0107571 A1 | 8/2002 | Foley |
| 2002/0107572 A1 | 8/2002 | Foley et al. |
| 2002/0107573 A1 | 8/2002 | Steinberg |
| 2002/0111683 A1 | 8/2002 | Ralph |
| 2002/0111687 A1 | 8/2002 | Ralph |
| 2002/0115742 A1 | 8/2002 | Trieu |
| 2002/0120269 A1 | 8/2002 | Lange |
| 2002/0120270 A1 | 8/2002 | Trieu |
| 2002/0120334 A1 | 8/2002 | Crozet et al. |
| 2002/0120336 A1 | 8/2002 | Santilli |
| 2002/0127720 A1 | 9/2002 | Erbe |
| 2002/0128714 A1 | 9/2002 | Manasas et al. |
| 2002/0143319 A1 | 10/2002 | Brock |
| 2002/0143400 A1 | 10/2002 | Biscup |
| 2002/0151894 A1 | 10/2002 | Melkent |
| 2002/0151979 A1 | 10/2002 | Lambrecht et al. |
| 2002/0156528 A1 | 10/2002 | Gau |
| 2002/0161443 A1 | 10/2002 | Michelson |
| 2002/0165550 A1 | 11/2002 | Frey et al. |
| 2002/0165612 A1 | 11/2002 | Gerber et al. |
| 2002/0165613 A1 | 11/2002 | Lin et al. |

(56)                References Cited

U.S. PATENT DOCUMENTS

| | | |
|---|---|---|
| 2002/0165616 A1 | 11/2002 | Heide et al. |
| 2002/0177897 A1 | 11/2002 | Michelson |
| 2003/0003127 A1 | 1/2003 | Brown et al. |
| 2003/0009226 A1 | 1/2003 | Graf |
| 2003/0009227 A1 | 1/2003 | Lambrecht et al. |
| 2003/0014113 A1 | 1/2003 | Ralph |
| 2003/0014115 A1 | 1/2003 | Ralph |
| 2003/0023306 A1 | 1/2003 | Liu et al. |
| 2003/0023311 A1 | 1/2003 | Trieu |
| 2003/0028197 A1 | 2/2003 | Hanson et al. |
| 2003/0028249 A1 | 2/2003 | Baccelli et al. |
| 2003/0028251 A1 | 2/2003 | Mathews |
| 2003/0034329 A1 | 2/2003 | Chou |
| 2003/0040796 A1 | 2/2003 | Ferree |
| 2003/0040798 A1 | 2/2003 | Michelson |
| 2003/0040799 A1 | 2/2003 | Boyd et al. |
| 2003/0040802 A1 | 2/2003 | Errico et al. |
| 2003/0045939 A1 | 3/2003 | Casutt |
| 2003/0055427 A1 | 3/2003 | Graf |
| 2003/0060891 A1 | 3/2003 | Shah |
| 2003/0069586 A1 | 4/2003 | Errico et al. |
| 2003/0069642 A1 | 4/2003 | Ralph |
| 2003/0069643 A1 | 4/2003 | Ralph |
| 2003/0073998 A1 | 4/2003 | Pagliuca |
| 2003/0074075 A1 | 4/2003 | Thomas |
| 2003/0074076 A1 | 4/2003 | Ferree |
| 2003/0078579 A1 | 4/2003 | Ferree |
| 2003/0078590 A1 | 4/2003 | Errico et al. |
| 2003/0078662 A1 | 4/2003 | Ralph |
| 2003/0083748 A1 | 5/2003 | Lee et al. |
| 2003/0093155 A1 | 5/2003 | Lambrecht et al. |
| 2003/0100950 A1 | 5/2003 | Moret |
| 2003/0100951 A1 | 5/2003 | Serhan |
| 2003/0120351 A1 | 6/2003 | Tofighi |
| 2003/0130667 A1 | 7/2003 | Lin |
| 2003/0130737 A1 | 7/2003 | McGahan |
| 2003/0135275 A1 | 7/2003 | Garcia et al. |
| 2003/0135276 A1 | 7/2003 | Eckman |
| 2003/0135277 A1 | 7/2003 | Bryan et al. |
| 2003/0135278 A1 | 7/2003 | Eckman |
| 2003/0135279 A1 | 7/2003 | Michelson |
| 2003/0139812 A1 | 7/2003 | Garcia et al. |
| 2003/0139813 A1 | 7/2003 | Messerli |
| 2003/0139816 A1 | 7/2003 | Michelson |
| 2003/0149438 A1 | 8/2003 | Nichols |
| 2003/0149483 A1 | 8/2003 | Michelson |
| 2003/0149484 A1 | 8/2003 | Michelson |
| 2003/0176921 A1 | 9/2003 | Lawson |
| 2003/0181981 A1 | 9/2003 | Lemaire |
| 2003/0195514 A1 | 10/2003 | Trieu |
| 2003/0195629 A1 | 10/2003 | Pafford et al. |
| 2003/0204260 A1 | 10/2003 | Ferree |
| 2003/0204261 A1 | 10/2003 | Elsermann et al. |
| 2003/0204362 A1 | 10/2003 | Beresford et al. |
| 2003/0208203 A1 | 11/2003 | Lim et al. |
| 2003/0216810 A1 | 11/2003 | Ralph |
| 2003/0220691 A1 | 11/2003 | Songer |
| 2003/0229358 A1 | 12/2003 | Errico et al. |
| 2003/0233146 A1 | 12/2003 | Grinberg et al. |
| 2003/0236520 A1 | 12/2003 | Lim et al. |
| 2004/0002763 A1 | 1/2004 | Phillips |
| 2004/0002764 A1 | 1/2004 | Gainor et al. |
| 2004/0006394 A1 | 1/2004 | Lipman et al. |
| 2004/0010316 A1 | 1/2004 | William et al. |
| 2004/0024400 A1 | 2/2004 | Michelson |
| 2004/0024462 A1 | 2/2004 | Ferree |
| 2004/0024463 A1 | 2/2004 | Thomas |
| 2004/0030390 A1 | 2/2004 | Ferree |
| 2004/0030391 A1 | 2/2004 | Ferree |
| 2004/0030392 A1 | 2/2004 | Lambrecht et al. |
| 2004/0034352 A1 | 2/2004 | Needham et al. |
| 2004/0034426 A1 | 2/2004 | Errico et al. |
| 2004/0038445 A1 | 2/2004 | Lowrey et al. |
| 2004/0044410 A1 | 3/2004 | Ferree |
| 2004/0049280 A1 | 3/2004 | Cauthen |
| 2004/0052829 A1 | 3/2004 | Shimp |
| 2004/0068321 A1 | 4/2004 | Ferree |
| 2004/0073315 A1 | 4/2004 | Justin et al. |
| 2004/0082999 A1 | 4/2004 | Mathys, Jr. et al. |
| 2004/0093082 A1 | 5/2004 | Ferree |
| 2004/0093083 A1 | 5/2004 | Branch et al. |
| 2004/0093088 A1 | 5/2004 | Ralph |
| 2004/0098129 A1 | 5/2004 | Lin |
| 2004/0102846 A1 | 5/2004 | Keller et al. |
| 2004/0115172 A1 | 6/2004 | Biachi et al. |
| 2004/0117018 A1 | 6/2004 | Michelson |
| 2004/0117019 A1 | 6/2004 | Trieu |
| 2004/0117022 A1 | 6/2004 | Marnay et al. |
| 2004/0127990 A1 | 7/2004 | Bartish, Jr. et al. |
| 2004/0127993 A1 | 7/2004 | Kast et al. |
| 2004/0127994 A1 | 7/2004 | Kast et al. |
| 2004/0133132 A1 | 7/2004 | Chappuis |
| 2004/0133207 A1 | 7/2004 | Abdou |
| 2004/0133278 A1 | 7/2004 | Marino et al. |
| 2004/0133280 A1 | 7/2004 | Trieu |
| 2004/0143331 A1 | 7/2004 | Errico et al. |
| 2004/0143332 A1 | 7/2004 | Krueger et al. |
| 2004/0148027 A1 | 7/2004 | Errico et al. |
| 2004/0148028 A1 | 7/2004 | Ferree |
| 2004/0153065 A1 | 8/2004 | Lim |
| 2004/0153157 A1 | 8/2004 | Keller |
| 2004/0153158 A1 | 8/2004 | Errico et al. |
| 2004/0153159 A1 | 8/2004 | Cauthen |
| 2004/0158328 A1 | 8/2004 | Eisermann |
| 2004/0162616 A1 | 8/2004 | Simonton |
| 2004/0162618 A1 | 8/2004 | Mujwid |
| 2004/0167520 A1 | 8/2004 | Zucherman et al. |
| 2004/0167534 A1 | 8/2004 | Errico et al. |
| 2004/0167536 A1 | 8/2004 | Errico et al. |
| 2004/0167538 A1 | 8/2004 | Gerber et al. |
| 2004/0167626 A1 | 8/2004 | Geremakis et al. |
| 2004/0167628 A1 | 8/2004 | Foley |
| 2004/0167637 A1 | 8/2004 | Biscup |
| 2004/0176843 A1 | 9/2004 | Zubok et al. |
| 2004/0176845 A1 | 9/2004 | Zubok et al. |
| 2004/0176848 A1 | 9/2004 | Zubok et al. |
| 2004/0176853 A1 | 9/2004 | Sennett |
| 2004/0181282 A1 | 9/2004 | Zucherman et al. |
| 2004/0186573 A1 | 9/2004 | Ferree |
| 2004/0186577 A1 | 9/2004 | Ferree |
| 2004/0186579 A1 | 9/2004 | Callaway et al. |
| 2004/0193272 A1 | 9/2004 | Zubok et al. |
| 2004/0199251 A1 | 10/2004 | McCombe et al. |
| 2004/0199252 A1 | 10/2004 | Sears |
| 2004/0199255 A1 | 10/2004 | Mathieu et al. |
| 2004/0204760 A1 | 10/2004 | Fitz |
| 2004/0210226 A1 | 10/2004 | Trieu |
| 2004/0210312 A1 | 10/2004 | Neumann |
| 2004/0214326 A1 | 10/2004 | Cousins |
| 2004/0220568 A1 | 11/2004 | Zucherman et al. |
| 2004/0220670 A1 | 11/2004 | Elsermann et al. |
| 2004/0225295 A1 | 11/2004 | Zubok et al. |
| 2004/0243237 A1 | 12/2004 | Unwin et al. |
| 2004/0243239 A1 | 12/2004 | Taylor |
| 2004/0243240 A1 | 12/2004 | Beaurain et al. |
| 2004/0249471 A1 | 12/2004 | Bindseil et al. |
| 2005/0004672 A1 | 1/2005 | Pafford et al. |
| 2005/0010226 A1 | 1/2005 | Grady et al. |
| 2005/0010292 A1 | 1/2005 | Carrasco |
| 2005/0015150 A1 | 1/2005 | Lee |
| 2005/0015154 A1 | 1/2005 | Lindsey et al. |
| 2005/0021030 A1 | 1/2005 | Pagliuca |
| 2005/0021042 A1 | 1/2005 | Marnay et al. |
| 2005/0021143 A1 | 1/2005 | Keller |
| 2005/0021144 A1 | 1/2005 | Malberg et al. |
| 2005/0021149 A1 | 1/2005 | Borruto et al. |
| 2005/0021151 A1 | 1/2005 | Landis |
| 2005/0027360 A1 | 2/2005 | Webb |
| 2005/0031704 A1 | 2/2005 | Ahn |
| 2005/0033305 A1 | 2/2005 | Schultz |
| 2005/0033437 A1 | 2/2005 | Bao et al. |
| 2005/0033438 A1 | 2/2005 | Schultz |
| 2005/0038445 A1 | 2/2005 | Errico et al. |
| 2005/0038515 A1 | 2/2005 | Kunzler |

(56)          References Cited

U.S. PATENT DOCUMENTS

| | | |
|---|---|---|
| 2005/0038516 A1 | 2/2005 | Spoonamore |
| 2005/0043796 A1 | 2/2005 | Grant et al. |
| 2005/0043798 A1 | 2/2005 | Eckman |
| 2005/0049589 A1 | 3/2005 | Jackson |
| 2005/0049590 A1 | 3/2005 | Alleyne |
| 2005/0049707 A1 | 3/2005 | Ferree |
| 2005/0055029 A1 | 3/2005 | Marik et al. |
| 2005/0055097 A1 | 3/2005 | Grunberg et al. |
| 2005/0060034 A1 | 3/2005 | Berry |
| 2005/0060035 A1 | 3/2005 | Errico et al. |
| 2005/0065604 A1 | 3/2005 | Stoll |
| 2005/0070918 A1 | 3/2005 | Zwirnmann et al. |
| 2005/0071005 A1 | 3/2005 | Carli et al. |
| 2005/0071010 A1 | 3/2005 | Crozet et al. |
| 2005/0071011 A1 | 3/2005 | Ralph |
| 2005/0071012 A1 | 3/2005 | Serhan |
| 2005/0080488 A1 | 4/2005 | Schultz |
| 2005/0085911 A1 | 4/2005 | Link |
| 2005/0085917 A1 | 4/2005 | Marnay et al. |
| 2005/0096745 A1 | 5/2005 | Andre |
| 2005/0101955 A1 | 5/2005 | Zucherman et al. |
| 2005/0107789 A1 | 5/2005 | Sweeney |
| 2005/0107881 A1 | 5/2005 | Alleyne |
| 2005/0112397 A1 | 5/2005 | Rolfe et al. |
| 2005/0113842 A1 | 5/2005 | Bertagnoli et al. |
| 2005/0118230 A1 | 6/2005 | Hill et al. |
| 2005/0119752 A1 | 6/2005 | Williams et al. |
| 2005/0125062 A1 | 6/2005 | Biedermann et al. |
| 2005/0125066 A1 | 6/2005 | McAfee |
| 2005/0131541 A1 | 6/2005 | Trieu |
| 2005/0137597 A1 | 6/2005 | Butler et al. |
| 2005/0143735 A1 | 6/2005 | Kyle |
| 2005/0143738 A1 | 6/2005 | Zucherman et al. |
| 2005/0143820 A1 | 6/2005 | Zucherman et al. |
| 2005/0143822 A1 | 6/2005 | Paul |
| 2005/0143824 A1 | 6/2005 | Richelsoph |
| 2005/0143826 A1 | 6/2005 | Zucherman et al. |
| 2005/0149048 A1 | 7/2005 | Leport et al. |
| 2005/0149192 A1 | 7/2005 | Zucherman et al. |
| 2005/0154463 A1 | 7/2005 | Trieu |
| 2005/0154464 A1 | 7/2005 | Humphreys et al. |
| 2005/0154466 A1 | 7/2005 | Humprheys et al. |
| 2005/0154468 A1 | 7/2005 | Rivin |
| 2005/0165398 A1 | 7/2005 | Reiley |
| 2005/0165400 A1 | 7/2005 | Fernandez |
| 2005/0165485 A1 | 7/2005 | Trieu |
| 2005/0177237 A1 | 8/2005 | Shappley |
| 2005/0177238 A1 | 8/2005 | Khandkar et al. |
| 2005/0177245 A1 | 8/2005 | Leatherbury et al. |
| 2005/0182416 A1 | 8/2005 | Lim et al. |
| 2005/0192670 A1 | 9/2005 | Zubok et al. |
| 2005/0192671 A1 | 9/2005 | Bao et al. |
| 2005/0196420 A1 | 9/2005 | Zucherman et al. |
| 2005/0203512 A1 | 9/2005 | Hawkins et al. |
| 2005/0203538 A1 | 9/2005 | Lo et al. |
| 2005/0209603 A1 | 9/2005 | Zucherman et al. |
| 2005/0209698 A1 | 9/2005 | Gordon et al. |
| 2005/0216084 A1 | 9/2005 | Fleischmann et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228498 A1 | 10/2005 | Andres |
| 2005/0228501 A1 | 10/2005 | Miller |
| 2005/0240182 A1 | 10/2005 | Zucherman et al. |
| 2005/0245937 A1 | 11/2005 | Winslow |
| 2005/0246021 A1 | 11/2005 | Ringeisen et al. |
| 2005/0251267 A1 | 11/2005 | Winterbottom |
| 2005/0256581 A1 | 11/2005 | Songer |
| 2005/0261768 A1 | 11/2005 | Trieu |
| 2005/0266581 A1 | 12/2005 | Droit et al. |
| 2005/0267587 A1 | 12/2005 | Lin et al. |
| 2005/0267588 A1 | 12/2005 | Lin et al. |
| 2005/0267589 A1 | 12/2005 | Lin et al. |
| 2005/0273166 A1 | 12/2005 | Sweeney |
| 2005/0278026 A1 | 12/2005 | Gordon et al. |
| 2005/0281856 A1 | 12/2005 | McGlohorn |
| 2005/0283245 A1 | 12/2005 | Gordon et al. |
| 2006/0004447 A1 | 1/2006 | Mastrorio et al. |
| 2006/0004453 A1 | 1/2006 | Bartish, Jr. et al. |
| 2006/0004454 A1 | 1/2006 | Ferree |
| 2006/0020341 A1 | 1/2006 | Schneid |
| 2006/0020342 A1 | 1/2006 | Ferree |
| 2006/0030860 A1 | 2/2006 | Peterman |
| 2006/0030943 A1 | 2/2006 | Peterman |
| 2006/0041314 A1 | 2/2006 | Millard |
| 2006/0041614 A1 | 2/2006 | Oe |
| 2006/0069436 A1 | 3/2006 | Sutton |
| 2006/0085076 A1 | 4/2006 | Krishna et al. |
| 2006/0089646 A1 | 4/2006 | Bonutti |
| 2006/0089654 A1 | 4/2006 | Lins et al. |
| 2006/0095043 A1 | 5/2006 | Martz et al. |
| 2006/0095136 A1 | 5/2006 | McLuen |
| 2006/0116767 A1 | 6/2006 | Magerl et al. |
| 2006/0129238 A1 | 6/2006 | Paltzer |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0149258 A1 | 7/2006 | Sousa |
| 2006/0149388 A1 | 7/2006 | Smith |
| 2006/0155295 A1 | 7/2006 | Supper |
| 2006/0167549 A1 | 7/2006 | Mathys et al. |
| 2006/0178744 A1 | 8/2006 | De Villiers et al. |
| 2006/0178745 A1 | 8/2006 | Bartish et al. |
| 2006/0195103 A1 | 8/2006 | Padget et al. |
| 2006/0195190 A1 | 8/2006 | Lechmann et al. |
| 2006/0195191 A1 | 8/2006 | Sweeney |
| 2006/0212122 A1 | 9/2006 | Perera |
| 2006/0217807 A1 | 9/2006 | Peterman |
| 2006/0217812 A1 | 9/2006 | Lambrecht et al. |
| 2006/0224159 A1 | 10/2006 | Anderson |
| 2006/0229623 A1 | 10/2006 | Bonutti |
| 2006/0229627 A1 | 10/2006 | Hunt et al. |
| 2006/0235403 A1 | 10/2006 | Blain |
| 2006/0235414 A1 | 10/2006 | Lim et al. |
| 2006/0235426 A1 | 10/2006 | Lim et al. |
| 2006/0235521 A1 | 10/2006 | Zucherman et al. |
| 2006/0235527 A1 | 10/2006 | Buettner-Janz et al. |
| 2006/0235528 A1 | 10/2006 | Buettner-Janz et al. |
| 2006/0235531 A1 | 10/2006 | Buettner-Janz et al. |
| 2006/0241597 A1 | 10/2006 | Mitchell |
| 2006/0241614 A1 | 10/2006 | Bruneau et al. |
| 2006/0241761 A1 | 10/2006 | Gately |
| 2006/0241770 A1 | 10/2006 | Rhoda |
| 2006/0247657 A1 | 11/2006 | Trieu |
| 2006/0247665 A1 | 11/2006 | Ferree |
| 2006/0247770 A1 | 11/2006 | Peterman |
| 2006/0247772 A1 | 11/2006 | McKay |
| 2006/0247776 A1 | 11/2006 | Kim |
| 2006/0247784 A1 | 11/2006 | Kim |
| 2006/0253121 A1 | 11/2006 | Gorensek et al. |
| 2006/0253132 A1 | 11/2006 | Evans et al. |
| 2006/0259037 A1 | 11/2006 | Hartmann et al. |
| 2006/0264946 A1 | 11/2006 | Young |
| 2006/0271194 A1 | 11/2006 | Zucherman et al. |
| 2006/0293662 A1 | 12/2006 | Boyer, II et al. |
| 2006/0293663 A1 | 12/2006 | Walkenhorst |
| 2006/0293748 A1 | 12/2006 | Alexander et al. |
| 2006/0293752 A1 | 12/2006 | Moumene |
| 2007/0027544 A1 | 2/2007 | McCord |
| 2007/0027547 A1 | 2/2007 | Rydell |
| 2007/0032568 A1 | 2/2007 | Lin et al. |
| 2007/0055246 A1 | 3/2007 | Zucherman et al. |
| 2007/0055275 A1 | 3/2007 | Schaller |
| 2007/0055376 A1 | 3/2007 | Michelson |
| 2007/0073398 A1 | 3/2007 | Fabian et al. |
| 2007/0093838 A1 | 4/2007 | Khodadadyan-Klostermann et al. |
| 2007/0093850 A1 | 4/2007 | Harris et al. |
| 2007/0100212 A1 | 5/2007 | Pimenta |
| 2007/0100348 A1 | 5/2007 | Cauthen, III et al. |
| 2007/0100454 A1 | 5/2007 | Burgess et al. |
| 2007/0100455 A1 | 5/2007 | Parsons |
| 2007/0118226 A1 | 5/2007 | Lambrecht et al. |
| 2007/0142843 A1 | 6/2007 | Dye |
| 2007/0161992 A1 | 7/2007 | Kwak et al. |

(56) References Cited

U.S. PATENT DOCUMENTS

| | | |
|---|---|---|
| 2007/0162001 A1 | 7/2007 | Chin et al. |
| 2007/0162128 A1 | 7/2007 | DeRidder et al. |
| 2007/0162131 A1 | 7/2007 | Freidman et al. |
| 2007/0162138 A1 | 7/2007 | Heinz |
| 2007/0191837 A1 | 8/2007 | Trieu |
| 2007/0191954 A1 | 8/2007 | Hansell et al. |
| 2007/0191959 A1 | 8/2007 | Hartmann et al. |
| 2007/0213461 A1 | 9/2007 | Hu et al. |
| 2007/0213641 A1 | 9/2007 | Francis |
| 2007/0213732 A1 | 9/2007 | Khanna et al. |
| 2007/0213826 A1 | 9/2007 | Smith |
| 2007/0225726 A1 | 9/2007 | Dye |
| 2007/0233076 A1 | 10/2007 | Trieu |
| 2007/0233143 A1 | 10/2007 | Josse et al. |
| 2007/0233153 A1 | 10/2007 | Shipp |
| 2007/0233272 A1 | 10/2007 | Boyce et al. |
| 2007/0260320 A1 | 11/2007 | Peterman et al. |
| 2007/0260324 A1 | 11/2007 | Joshi et al. |
| 2007/0270812 A1 | 11/2007 | Peckham |
| 2007/0270961 A1 | 11/2007 | Ferguson |
| 2007/0270965 A1 | 11/2007 | Ferguson |
| 2007/0288005 A1 | 12/2007 | Amin et al. |
| 2007/0293948 A1 | 12/2007 | Bagga et al. |
| 2007/0293949 A1 | 12/2007 | Salerni |
| 2008/0009880 A1 | 1/2008 | Warnick |
| 2008/0009945 A1 | 1/2008 | Pacheco |
| 2008/0015588 A1 | 1/2008 | Hawkes |
| 2008/0015597 A1 | 1/2008 | Whipple |
| 2008/0021454 A1 | 1/2008 | Chao et al. |
| 2008/0021456 A1 | 1/2008 | Gupta et al. |
| 2008/0065219 A1 | 3/2008 | Dye |
| 2008/0071372 A1 | 3/2008 | Butler et al. |
| 2008/0077153 A1 | 3/2008 | Pernsteiner |
| 2008/0077241 A1 | 3/2008 | Nguyen |
| 2008/0091211 A1 | 4/2008 | Gately |
| 2008/0097444 A1 | 4/2008 | Erickson et al. |
| 2008/0103598 A1 | 5/2008 | Trudeau |
| 2008/0109081 A1 | 5/2008 | Bao et al. |
| 2008/0114367 A1 | 5/2008 | Meyer |
| 2008/0114456 A1 | 5/2008 | Dewey et al. |
| 2008/0140082 A1 | 6/2008 | Erdem et al. |
| 2008/0154377 A1 | 6/2008 | Voellmicke |
| 2008/0177271 A1 | 7/2008 | Yeh |
| 2008/0183211 A1 | 7/2008 | Lamborne et al. |
| 2008/0188897 A1 | 8/2008 | Krebs et al. |
| 2008/0188940 A1 | 8/2008 | Cohen et al. |
| 2008/0195209 A1 | 8/2008 | Garcia et al. |
| 2008/0200985 A1 | 8/2008 | Robie |
| 2008/0208342 A1 | 8/2008 | Hanson et al. |
| 2008/0221695 A1 | 9/2008 | Jacofsky et al. |
| 2008/0234828 A1 | 9/2008 | Wagner |
| 2008/0243252 A1 | 10/2008 | Hanson et al. |
| 2008/0288073 A1 | 11/2008 | Renganath |
| 2008/0288076 A1 | 11/2008 | Soo |
| 2008/0288081 A1 | 11/2008 | Scrafton |
| 2008/0306488 A1 | 12/2008 | Altarac |
| 2008/0306489 A1 | 12/2008 | Altarac |
| 2008/0306538 A1 | 12/2008 | Moore |
| 2008/0306596 A1 | 12/2008 | Jones |
| 2008/0306598 A1 | 12/2008 | Hanson et al. |
| 2009/0018584 A1 | 1/2009 | Hendrson, Sr. et al. |
| 2009/0024174 A1 | 1/2009 | Stark |
| 2009/0030519 A1 | 1/2009 | Falahee |
| 2009/0036927 A1 | 2/2009 | Vestgaarden |
| 2009/0043390 A1 | 2/2009 | Meisel |
| 2009/0048675 A1 | 2/2009 | Bhatnagar et al. |
| 2009/0054901 A1 | 2/2009 | Oh |
| 2009/0054930 A1 | 2/2009 | Aflatoon |
| 2009/0062917 A1 | 3/2009 | Foley et al. |
| 2009/0093881 A1 | 4/2009 | Bandyopadhyay et al. |
| 2009/0099610 A1 | 4/2009 | Johnson et al. |
| 2009/0099661 A1 | 4/2009 | Bhattacharya |
| 2009/0105824 A1 | 4/2009 | Jones |
| 2009/0105825 A1 | 4/2009 | Foreman et al. |
| 2009/0131986 A1 | 5/2009 | Lee et al. |
| 2009/0138053 A1 | 5/2009 | Assell et al. |
| 2009/0164020 A1 | 6/2009 | Janowski et al. |
| 2009/0164023 A1 | 6/2009 | Devine |
| 2009/0185904 A1 | 7/2009 | Landberg |
| 2009/0216238 A1 | 8/2009 | Stark |
| 2009/0228054 A1 | 9/2009 | Hoffman et al. |
| 2009/0234395 A1 | 9/2009 | Hoffman et al. |
| 2009/0240333 A1 | 9/2009 | Trudeau |
| 2009/0240336 A1 | 9/2009 | Vander Meulen et al. |
| 2009/0248163 A1 | 10/2009 | King et al. |
| 2009/0259261 A1 | 10/2009 | Reiley |
| 2009/0270986 A1 | 10/2009 | Christensen |
| 2009/0276049 A1 | 11/2009 | Weiland |
| 2009/0281580 A1 | 11/2009 | Emannuel |
| 2009/0287254 A1 | 11/2009 | Nayet et al. |
| 2009/0291308 A1 | 11/2009 | Pfister et al. |
| 2009/0295042 A1 | 12/2009 | Pfister et al. |
| 2009/0299479 A1 | 12/2009 | Jones |
| 2010/0003102 A1 | 1/2010 | Nagaiwa et al. |
| 2010/0004747 A1 | 1/2010 | Lin |
| 2010/0010496 A1 | 1/2010 | Isaza et al. |
| 2010/0016974 A1 | 1/2010 | Janowski et al. |
| 2010/0070039 A1 | 3/2010 | Guyer et al. |
| 2010/0076559 A1 | 3/2010 | Bagga et al. |
| 2010/0100131 A1 | 4/2010 | Wallenstein |
| 2010/0106190 A1 | 4/2010 | Linares |
| 2010/0106200 A1 | 4/2010 | Stark |
| 2010/0131011 A1 | 5/2010 | Stark |
| 2010/0137990 A1 | 6/2010 | Apatsidis et al. |
| 2010/0171306 A1 | 7/2010 | Gillot et al. |
| 2010/0191337 A1 | 7/2010 | Zamani et al. |
| 2010/0198267 A1 | 8/2010 | Vaidya |
| 2010/0204798 A1 | 8/2010 | Gerbec et al. |
| 2010/0228296 A1 | 9/2010 | Vraney et al. |
| 2010/0228369 A1 | 9/2010 | Eggers et al. |
| 2010/0234966 A1 | 9/2010 | Lo |
| 2010/0249797 A1 | 9/2010 | Trudeau |
| 2010/0268228 A1 | 10/2010 | Petersen |
| 2010/0268339 A1 | 10/2010 | Malinin et al. |
| 2010/0280619 A1 | 11/2010 | Yuan |
| 2011/0040362 A1 | 2/2011 | Godara et al. |
| 2011/0045087 A1 | 2/2011 | Kerr et al. |
| 2011/0054373 A1 | 3/2011 | Reiley |
| 2011/0054621 A1 | 3/2011 | Lim |
| 2011/0087294 A1 | 4/2011 | Reiley |
| 2011/0087296 A1 | 4/2011 | Reiley et al. |
| 2011/0093078 A1 | 4/2011 | Puno |
| 2011/0098816 A1 | 4/2011 | Jacob et al. |
| 2011/0098817 A1 | 4/2011 | Eckhardt et al. |
| 2011/0106163 A1 | 5/2011 | Hochschuler et al. |
| 2011/0106259 A1 | 5/2011 | Lindenmann et al. |
| 2011/0112642 A1 | 5/2011 | Tohmeh |
| 2011/0118785 A1 | 5/2011 | Reiley |
| 2011/0118790 A1 | 5/2011 | Reiley |
| 2011/0118841 A1 | 5/2011 | Reiley |
| 2011/0144752 A1 | 6/2011 | DeFelice et al. |
| 2011/0144766 A1 | 6/2011 | Kale et al. |
| 2011/0160772 A1 | 6/2011 | Arcenio et al. |
| 2011/0165340 A1 | 7/2011 | Baumann et al. |
| 2011/0166602 A1 | 7/2011 | Malek |
| 2011/0168091 A1 | 7/2011 | Baumann et al. |
| 2011/0172774 A1 | 7/2011 | Varela |
| 2011/0184472 A1 | 7/2011 | Niederberger et al. |
| 2011/0190888 A1 | 8/2011 | Bertele et al. |
| 2011/0190904 A1 | 8/2011 | Lechmann et al. |
| 2011/0208309 A1 | 8/2011 | Peterson |
| 2011/0224796 A1 | 9/2011 | Weiland et al. |
| 2011/0230970 A1 | 9/2011 | Lynn et al. |
| 2011/0245923 A1 | 10/2011 | Cobb et al. |
| 2011/0251689 A1 | 10/2011 | Seifert |
| 2011/0264218 A1 | 10/2011 | Asaad |
| 2011/0270402 A1 | 11/2011 | Frey et al. |
| 2011/0282453 A1 | 11/2011 | Greenhalgh et al. |
| 2011/0282454 A1 | 11/2011 | Ullrich, Jr. et al. |
| 2011/0295372 A1 | 12/2011 | Peterman |
| 2011/0301709 A1 | 12/2011 | Kraus et al. |
| 2011/0301710 A1 | 12/2011 | Mather et al. |
| 2011/0307042 A1 | 12/2011 | DeCarmine |
| 2011/0313531 A1 | 12/2011 | Lechmann et al. |

(56) References Cited

U.S. PATENT DOCUMENTS

| | | |
|---|---|---|
| 2011/0319946 A1 | 12/2011 | Levy et al. |
| 2011/0319998 A1 | 12/2011 | O'Neil et al. |
| 2011/0320000 A1 | 12/2011 | O'Neil et al. |
| 2012/0010715 A1 | 1/2012 | Spann |
| 2012/0010717 A1 | 1/2012 | Spann |
| 2012/0029641 A1 | 2/2012 | Curran et al. |
| 2012/0035730 A1 | 2/2012 | Spann |
| 2012/0046750 A1 | 2/2012 | Obrigkeit et al. |
| 2012/0071984 A1 | 3/2012 | Michelson |
| 2012/0083885 A1 | 4/2012 | Thibodeau |
| 2012/0130494 A1 | 5/2012 | DeLurio et al. |
| 2012/0143334 A1 | 6/2012 | Boyce et al. |
| 2012/0158062 A1 | 6/2012 | Nunley et al. |
| 2012/0158144 A1 | 6/2012 | Ullrich, Jr. et al. |
| 2012/0172934 A1 | 7/2012 | Fisher et al. |
| 2012/0179261 A1 | 7/2012 | Soo |
| 2012/0185045 A1 | 7/2012 | Morris |
| 2012/0191188 A1 | 7/2012 | Huang |
| 2012/0191189 A1 | 7/2012 | Huang |
| 2012/0191191 A1 | 7/2012 | Trieu |
| 2012/0203229 A1 | 8/2012 | Appenzeller et al. |
| 2012/0203344 A1 | 8/2012 | Trudeau |
| 2012/0232349 A1 | 9/2012 | Perrow |
| 2012/0232664 A1 | 9/2012 | Ulrich, Jr. et al. |
| 2012/0239150 A1 | 9/2012 | Ulrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0265306 A1 | 10/2012 | Trieu |
| 2012/0265307 A1 | 10/2012 | Guyer et al. |
| 2012/0265311 A1 | 10/2012 | Mather et al. |
| 2012/0277869 A1 | 11/2012 | Siccardi |
| 2012/0277870 A1 | 11/2012 | Wolters |
| 2012/0277876 A1 | 11/2012 | Ullrich, Jr. et al. |
| 2012/0283834 A1 | 11/2012 | Gottlieb et al. |
| 2012/0283838 A1 | 11/2012 | Rhoda |
| 2012/0290091 A1 | 11/2012 | Kirschman |
| 2012/0303123 A1 | 11/2012 | Robie |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310287 A1 | 12/2012 | Bao et al. |
| 2012/0310354 A1 | 12/2012 | Ullrich, Jr. et al. |
| 2012/0310364 A1 | 12/2012 | Li et al. |
| 2012/0312779 A1 | 12/2012 | Patterson et al. |
| 2012/0316650 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |
| 2013/0018466 A1 | 1/2013 | Yu |
| 2013/0030534 A1 | 1/2013 | DeLurio et al. |
| 2013/0046345 A1 | 2/2013 | Jones et al. |
| 2013/0110243 A1 | 5/2013 | Patterson et al. |
| 2013/0116793 A1 | 5/2013 | Kloss |
| 2013/0171019 A1 | 7/2013 | Gessler et al. |
| 2013/0184765 A1 | 7/2013 | Beyar et al. |
| 2013/0204372 A1 | 8/2013 | Mohar |
| 2013/0217838 A1 | 8/2013 | DeFelice et al. |
| 2013/0273131 A1 | 10/2013 | Frangov et al. |
| 2013/0282120 A1 | 10/2013 | Refai et al. |
| 2013/0282122 A1 | 10/2013 | Ullrich, Jr. et al. |
| 2014/0031942 A1 | 1/2014 | Ullrich, Jr. et al. |
| 2014/0088716 A1 | 3/2014 | Zubok et al. |
| 2014/0100657 A1 | 4/2014 | McCormack et al. |
| 2014/0107785 A1 | 4/2014 | Geisler et al. |
| 2014/0107786 A1 | 4/2014 | Geisler et al. |
| 2014/0172103 A1 | 6/2014 | O'Neil |
| 2014/0172111 A1 | 6/2014 | Lang et al. |
| 2014/0249631 A1 | 9/2014 | Weiman |
| 2014/0277434 A1 | 9/2014 | Weeber |
| 2014/0277487 A1 | 9/2014 | Davenport et al. |
| 2014/0277511 A1 | 9/2014 | Ullrich, Jr. et al. |
| 2014/0288650 A1 | 9/2014 | Hunt |
| 2015/0018956 A1 | 1/2015 | Steinmann et al. |
| 2015/0045924 A1 | 2/2015 | Cluckers et al. |
| 2015/0061195 A1 | 3/2015 | DeFelice et al. |
| 2015/0134063 A1 | 5/2015 | Steinmann et al. |
| 2015/0142158 A1 | 5/2015 | Szwedka |
| 2015/0265414 A1 | 9/2015 | Mermuys |
| 2015/0274588 A1 | 10/2015 | DeFelice et al. |
| 2015/0328665 A1 | 11/2015 | DeFelice et al. |
| 2015/0351915 A1 | 12/2015 | DeFelice et al. |
| 2015/0351929 A1 | 12/2015 | Ullrich, Jr. et al. |
| 2015/0367575 A1 | 12/2015 | Roels et al. |
| 2016/0022431 A1 | 1/2016 | Wickham |
| 2016/0038301 A1 | 2/2016 | Wickham |
| 2016/0051371 A1 | 2/2016 | DeFelice et al. |
| 2016/0058574 A1 | 3/2016 | Patterson et al. |
| 2016/0058575 A1 | 3/2016 | Sutterlin, III et al. |
| 2016/0106551 A1 | 4/2016 | Grimberg, Jr. et al. |
| 2016/0166284 A1 | 6/2016 | Hacking et al. |
| 2016/0199193 A1 | 7/2016 | Willis |
| 2016/0213485 A1 | 7/2016 | Schaufler et al. |
| 2016/0213486 A1 | 7/2016 | Nunley |
| 2016/0213487 A1 | 7/2016 | Wilson et al. |
| 2016/0213488 A1 | 7/2016 | Moore et al. |
| 2016/0213821 A1 | 7/2016 | Melkent |
| 2016/0278934 A1 | 9/2016 | Mermuys |
| 2016/0338851 A1 | 11/2016 | Ashleigh et al. |
| 2017/0000619 A1 | 1/2017 | Milz |
| 2017/0057015 A1 | 3/2017 | DeFelice et al. |
| 2017/0112549 A1 | 4/2017 | Kilpela et al. |
| 2017/0156878 A1 | 6/2017 | Tsai et al. |
| 2017/0156880 A1 | 6/2017 | Halverson et al. |
| 2017/0239061 A1 | 8/2017 | Parry |
| 2017/0239066 A1 | 8/2017 | Walsh |
| 2017/0296354 A1 | 10/2017 | Trudeau |
| 2017/0304070 A1 | 10/2017 | Perrow |
| 2017/0312089 A1 | 11/2017 | Duarte et al. |
| 2017/0319355 A1 | 11/2017 | Perrow |
| 2018/0071113 A1 | 3/2018 | Melkent |
| 2018/0104063 A1 | 4/2018 | Asaad |
| 2019/0298542 A1 | 10/2019 | Kloss |
| 2019/0328546 A1 | 10/2019 | Palagi et al. |
| 2019/0358058 A1 | 11/2019 | Trieu |
| 2019/0388232 A1 | 12/2019 | Purcell |
| 2020/0237526 A1 | 7/2020 | Wilson |
| 2022/0104950 A1 | 4/2022 | Trudeau et al. |

FOREIGN PATENT DOCUMENTS

| | | |
|---|---|---|
| CA | 2395609 | 8/2001 |
| CA | 2482403 | 9/2003 |
| CA | 2548780 | 7/2005 |
| CN | 1697633 | 11/2005 |
| CN | 103445883 | 12/2013 |
| DE | 9000094 | 1/1991 |
| DE | 29612269 | 9/1996 |
| DE | 19818956 | 11/1998 |
| DE | 19738052 | 3/1999 |
| DE | 29911422 | 8/1999 |
| DE | 19816832 | 1/2000 |
| DE | 10130825 | 3/2002 |
| DE | 10309702 | 9/2004 |
| DE | 202005005405 | 6/2005 |
| DE | 102008024281 | 12/2009 |
| DE | 102008024288 | 12/2009 |
| EP | 0042271 | 12/1981 |
| EP | 0179695 | 4/1986 |
| EP | 0346129 | 12/1989 |
| EP | 0425542 | 5/1991 |
| EP | 0760687 | 3/1997 |
| EP | 0773008 | 5/1997 |
| EP | 0834295 | 4/1998 |
| EP | 0919209 | 6/1999 |
| EP | 1104665 | 6/2001 |
| EP | 1132061 | 9/2001 |
| EP | 1138285 | 10/2001 |
| EP | 1205160 | 5/2002 |
| EP | 1212992 | 6/2002 |
| EP | 1346695 | 9/2003 |
| EP | 1464307 | 10/2004 |
| EP | 1698305 | 9/2006 |

(56) References Cited

FOREIGN PATENT DOCUMENTS

| | | |
|---|---|---|
| EP | 1772108 | 4/2007 |
| EP | 1905391 | 4/2008 |
| EP | 2085056 | 8/2009 |
| EP | 2145913 | 1/2010 |
| EP | 2457538 | 5/2012 |
| EP | 2623069 | 8/2013 |
| EP | 3050540 | 8/2016 |
| EP | 2349107 | 12/2016 |
| EP | 2273952 | 2/2018 |
| FR | 2372622 | 6/1978 |
| FR | 2703580 | 10/1994 |
| FR | 2723841 | 3/1996 |
| FR | 2732841 | 10/1996 |
| FR | 2754170 | 4/1998 |
| FR | 2787014 | 6/2000 |
| FR | 2797179 | 2/2001 |
| FR | 2799116 | 4/2001 |
| FR | 2801782 | 6/2001 |
| FR | 2805985 | 9/2001 |
| FR | 2824261 | 11/2002 |
| FR | 2827157 | 1/2003 |
| FR | 2841124 | 12/2003 |
| JP | S63-300758 | 12/1988 |
| JP | H01-308557 | 12/1989 |
| JP | H02-111358 | 4/1990 |
| JP | H02-215461 | 8/1990 |
| JP | H02-224659 | 9/1990 |
| JP | H02-224660 | 9/1990 |
| JP | H03-275055 | 12/1991 |
| JP | H03-275056 | 12/1991 |
| JP | H04-303444 | 10/1992 |
| JP | H05-277141 | 10/1993 |
| JP | H06-285099 | 10/1994 |
| JP | H07-031673 | 2/1995 |
| JP | H08-098850 | 4/1996 |
| JP | H08-098851 | 4/1996 |
| JP | H11-009618 | 1/1999 |
| JP | H11-137585 | 5/1999 |
| JP | 2000-210316 | 8/2000 |
| JP | 2001-054564 | 2/2001 |
| JP | 2003-180814 | 7/2003 |
| JP | 2006-508714 | 3/2006 |
| JP | 2008-284348 | 11/2008 |
| JP | 2011-530387 | 12/2011 |
| JP | 2012-232124 | 11/2012 |
| JP | 2016-135243 | 7/2016 |
| WO | WO 90/00037 | 1/1990 |
| WO | WO 90/11740 | 10/1990 |
| WO | WO 91/00713 | 1/1991 |
| WO | WO 91/05521 | 5/1991 |
| WO | WO 91/16867 | 11/1991 |
| WO | WO 93/16664 | 9/1993 |
| WO | WO 94/05235 | 3/1994 |
| WO | WO 94/19174 | 9/1994 |
| WO | WO 94/28824 | 12/1994 |
| WO | WO 95/00082 | 1/1995 |
| WO | WO 95/10248 | 4/1995 |
| WO | WO 95/12369 | 5/1995 |
| WO | WO 95/32673 | 12/1995 |
| WO | WO 96/01598 | 1/1996 |
| WO | WO 96/08360 | 3/1996 |
| WO | WO 96/11642 | 4/1996 |
| WO | WO 96/27339 | 9/1996 |
| WO | WO 96/28117 | 9/1996 |
| WO | WO 96/40014 | 12/1996 |
| WO | WO 96/40015 | 12/1996 |
| WO | WO 96/40019 | 12/1996 |
| WO | WO 97/17285 | 5/1997 |
| WO | WO 97/34546 | 9/1997 |
| WO | WO 98/05274 | 2/1998 |
| WO | WO 98/19617 | 5/1998 |
| WO | WO 98/55053 | 12/1998 |
| WO | WO 99/11203 | 3/1999 |
| WO | WO 99/20208 | 4/1999 |
| WO | WO 99/22675 | 5/1999 |
| WO | WO 99/30651 | 6/1999 |
| WO | WO 00/13619 | 3/2000 |
| WO | WO 00/25707 | 5/2000 |
| WO | WO 00/38574 | 7/2000 |
| WO | WO 00/40177 | 7/2000 |
| WO | WO 00/42953 | 7/2000 |
| WO | WO 00/49977 | 8/2000 |
| WO | WO 00/59412 | 10/2000 |
| WO | WO 00/66011 | 11/2000 |
| WO | WO 00/66045 | 11/2000 |
| WO | WO 01/32100 | 5/2001 |
| WO | WO 01/37728 | 5/2001 |
| WO | WO 01/05638 | 8/2001 |
| WO | WO 01/58369 | 8/2001 |
| WO | WO 01/68003 | 9/2001 |
| WO | WO 01/95818 | 12/2001 |
| WO | WO 02/02151 | 1/2002 |
| WO | WO 02/09626 | 2/2002 |
| WO | WO 02/30337 | 4/2002 |
| WO | WO 02/38086 | 5/2002 |
| WO | WO 02/080820 | 10/2002 |
| WO | WO 02/87480 | 11/2002 |
| WO | WO 03/005887 | 1/2003 |
| WO | WO 03/011343 | 2/2003 |
| WO | WO 03/030956 | 4/2003 |
| WO | WO 03/035129 | 5/2003 |
| WO | WO 03/099171 | 12/2003 |
| WO | WO 03/099172 | 12/2003 |
| WO | WO 2004/000177 | 12/2003 |
| WO | WO 2005/009298 | 2/2005 |
| WO | WO 2005/041818 | 5/2005 |
| WO | WO 2005/051240 | 6/2005 |
| WO | WO 2005/055869 | 6/2005 |
| WO | WO 2005/071190 | 8/2005 |
| WO | WO 2005/077307 | 8/2005 |
| WO | WO 2005/086776 | 9/2005 |
| WO | WO 2005/092208 | 10/2005 |
| WO | WO 2005/102226 | 11/2005 |
| WO | WO 2005/115261 | 12/2005 |
| WO | WO 2006/016384 | 2/2006 |
| WO | WO 2006/022644 | 3/2006 |
| WO | WO 2006/064356 | 6/2006 |
| WO | WO 2006/101837 | 9/2006 |
| WO | WO 2006/102428 | 9/2006 |
| WO | WO 2007/015028 | 2/2007 |
| WO | WO 2007/016801 | 2/2007 |
| WO | WO 2007/087535 | 8/2007 |
| WO | WO 2007/121457 | 10/2007 |
| WO | WO 2008/034135 | 3/2008 |
| WO | WO 2008/034140 | 3/2008 |
| WO | WO 2008/098054 | 8/2008 |
| WO | WO 2008/140551 | 11/2008 |
| WO | WO 2009/029074 | 3/2009 |
| WO | WO 2009/040840 | 4/2009 |
| WO | WO 2009/068021 | 6/2009 |
| WO | WO 2009/154560 | 12/2009 |
| WO | WO 2010/065015 | 6/2010 |
| WO | WO 2011/014135 | 2/2011 |
| WO | WO 2011/030017 | 3/2011 |
| WO | WO 2011/056172 | 5/2011 |
| WO | WO 2011/097905 | 8/2011 |
| WO | WO 2012/008279 | 1/2012 |
| WO | WO 2012/010327 | 1/2012 |
| WO | WO 2013/008111 | 1/2013 |
| WO | WO 2013/017647 | 2/2013 |
| WO | WO 2013/155500 | 10/2013 |
| WO | WO 2013/156545 | 10/2013 |
| WO | WO 2013/181234 | 12/2013 |
| WO | WO 2014/096294 | 6/2014 |
| WO | WO 2015/187038 | 12/2015 |
| WO | WO 2017/087944 | 5/2017 |
| ZA | 201003898 | 6/2010 |
| ZA | 201103777 | 6/2012 |

OTHER PUBLICATIONS

Notice of Acceptance for Australia Patent Application No. 2018327353, dated Nov. 29, 2024, 3 pages.

(56) References Cited

OTHER PUBLICATIONS

Notice of Allowance for U.S. Appl. No. 17/504,239, dated Jan. 3, 2025, 7 pages.

Notice of Allowance for Canada Patent Application No. 3074834, dated Mar. 7, 2025, 1 page.

Official Action for Europe Patent Application No. 18853354.1, dated Apr. 2, 2025, 10 pages.

Bao, Qi-Bin and Yuan, Hansen A., "Artificial Disc Technology", Neurosurg. Focus, vol. 9, No. 4, Oct. 2000, 7 pp.

Depuy Spine, Inc., Charite Artificial Disc Centreline TDR Instrumentation, Surgical Technique, 1 Feb. 2004, 21 pp.

Depuy Spine, Inc.; Charite Artificial Disc Product Catalog, Dec. 2004, 16 pp.

Feder, Barnaby J., "When FD.A. Says Yes, but Insurers Say No", The New York Times, Jul. 6, 2005, 2 pp.

Medtronic Sofamor Danek, Union/Union L, Anterior & Lateral Impacted Fusion Devices, Clear Choice of Stabilization, 2001, (25 pages).

Millsaps, Bridget Butler, "3D Printed Spinal Implants: RTI Surgical Granted Exclusive License to OPM OsteoFab Technology Platform", 3Dprint.com, <https://3dprint.com/119715/rti-opm-spinal-implants/>, published Feb. 15, 2016, accessed Jul. 28, 2017, 11 pages.

Park et al., Kambin's Triangle Approach of Lumbar Transforaminal Epidural Injection with Spinal Stenosis, Dec. 30, 2011 (10 pages).

RTI Surgical, RTI Surgical Announces Agreement With Oxford performance Materials, dated Feb. 11, 2016, 2 pages, accessed on Dec. 27, 2017 at the following website: https://www.businesswire.com/news/home/20160211006300/en/RTI-Surgical%C2%AE-Announces-Agreement-Oxford-Performance-Materials.

Wang M, Bhardwaj B, Webster T; Antibacterial properties of PEKK for orthopedic applications. Int'l Journal of Nanomedicine. 2017: 12 6471-6476, published Sep. 5, 2017. (6 pages).

Zdeblick, T. et al., Cervical Interbody Fusion Cages, An Animal Model With and Without Bone Morphogenetic Protein, Spine, 1998, vol. 23, No. 7, 9 pp.

ProSpace Interbody System: Product Brochure, Aesculap Implant Systems, LLC, 2014, pp. 1-4 (4 pages).

Forza PTC Spacer System: Posterior & Transforaminal Lumbar Interbody Fusion, Orthofix Holdings, Inc., copyright Apr. 2020, describing implant publicly available before Sep. 8, 2017 (8 pages).

Tritanium® PL Posterior Lumbar Cage: Surgical Technique, Stryker, 2018, pp. 1-32 (32 pages).

Endoskeleton® TT/TO: Posterior Interbody Fusion Device for the Lumbar Spine, Titan Spine, 2011 (2 pages).

A Revolution in Interbody Fusion: Cervical Interbody Fusion Device, Valeo II® C, CTL Amedica Corporation, copyright 2019, describing implant publicly available before Sep. 8, 2017 (2 pages).

A Revolution in Interbody Fusion: Transforaminal Lumbar Interbody Fusion Device, Valeo II® TL, CTL Amedica Corporation, copyright 2019, describing implant publicly available before Sep. 8, 2017 (2 pages).

Funato et al., "Mineralized Matrix Generated by Cultured Osteoblasts on Micro-roughened Surface of Titanium Mesh is High in Hardness and Stiffness," Journal of Japanese Society of Oral Implantology, vol. 23, No. 2, Jun. 30, 2010, pp. 229-238 (with English abstract).

Invitation to Pay Additional Fees mailed Nov. 8, 2018, in corresponding PCT/US2018/050001, 2 pages.

PCT Search Report and Written Opinion from International Patent Application No. PCT/US2018/050001 dated Jan. 22, 2019; 22 pages.

Partial European Search Report and Written Opinion issued Apr. 22, 2021, in corresponding European Application No. 18853354.1 (20 pages).

Extended European Search Report and Written Opinion dated Sep. 6, 2021, in corresponding European Application No. 18853354.1 (20 pages).

Official Action for Australia Patent Application No. 2018327353, dated Jan. 16, 2024, 4 pages.

Official Action for Canada Patent Application No. 3074834, dated Sep. 5, 2023, 4 pages.

Official Action (with English translation) for Japan Patent Application No. 2020-513735, dated Nov. 1, 2023, 20 pages.

Notice of Allowance for Japan Patent Application No. 2020-513735, dated Mar. 26, 2024, 3 pages.

Official Action for U.S. Appl. No. 16/124,935, dated Feb. 26, 2020, 10 pages. Restriction Requirement.

Official Action for U.S. Appl. No. 16/124,935, dated May 28, 2020, 27 pages.

Official Action for U.S. Appl. No. 16/124,935, dated Sep. 25, 2020, 26 pages.

Notice of Allowance for U.S. Appl. No. 16/124,935, dated Dec. 4, 2020, 6 pages.

Notice of Allowance for U.S. Appl. No. 16/124,935, dated May 28, 2021, 6 pages.

Corrected Notice of Allowance for U.S. Appl. No. 16/124,935, dated Sep. 20, 2021, 3 pages.

Official Action for U.S. Appl. No. 17/504,239, dated Apr. 19, 2024, 5 pages. Restriction Requirement.

Official Action for U.S. Appl. No. 17/504,239, dated Aug. 20, 2024, 15 pages.

Official Action for U.S. Appl. No. 29/621,557, dated Mar. 31, 2020, 6 pages. Restriction Requirement.

Notice of Allowance for U.S. Appl. No. 29/621,557, dated Jun. 10, 2020, 7 pages.

Notice of Allowance for U.S. Appl. No. 29/621,557, dated Sep. 8, 2020, 7 pages.

Notice of Allowance for U.S. Appl. No. 29/621,557, dated Oct. 8, 2020, 2 pages.

Official Action for U.S. Appl. No. 29/761,831, dated Mar. 28, 2022, 6 pages. Restriction Requirement.

Notice of Allowance for U.S. Appl. No. 29/761,831, dated Jun. 27, 2022, 7 pages.

Official Action for Australia Patent Application No. 2018327353, dated Jun. 21, 2024, 4 pages.

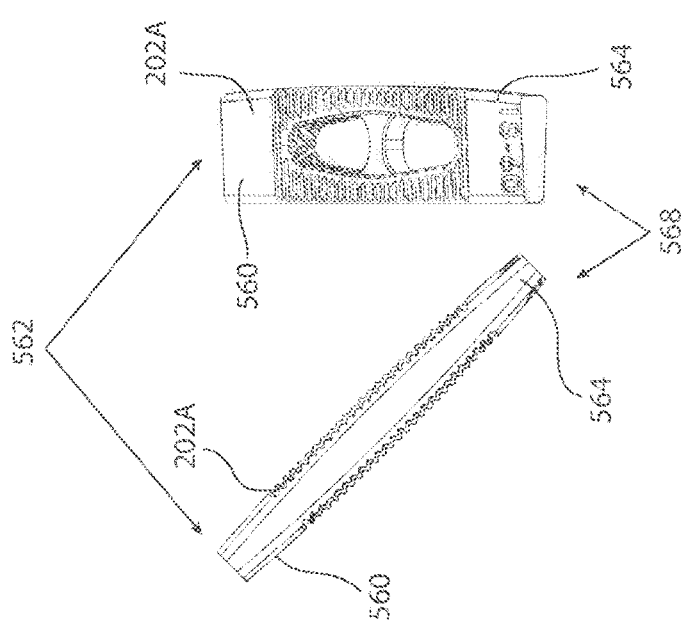
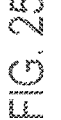
FIG. 25
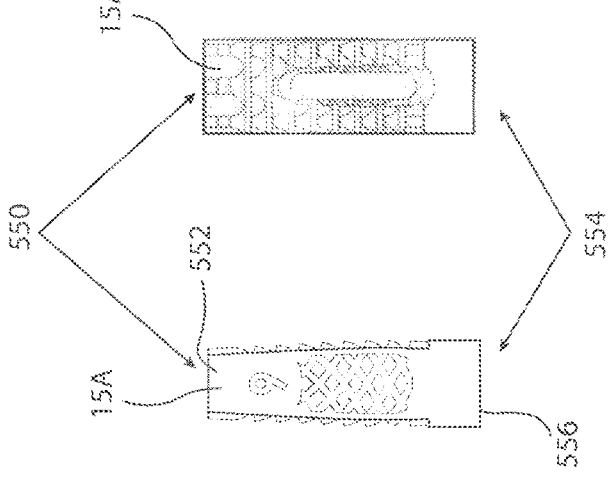
FIG. 24
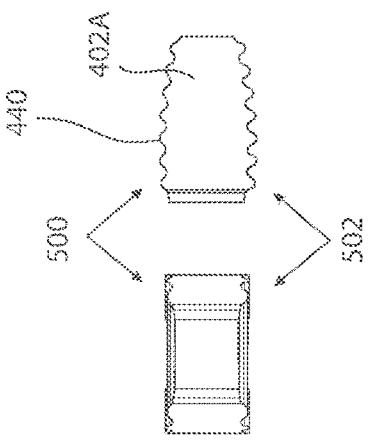
FIG. 23

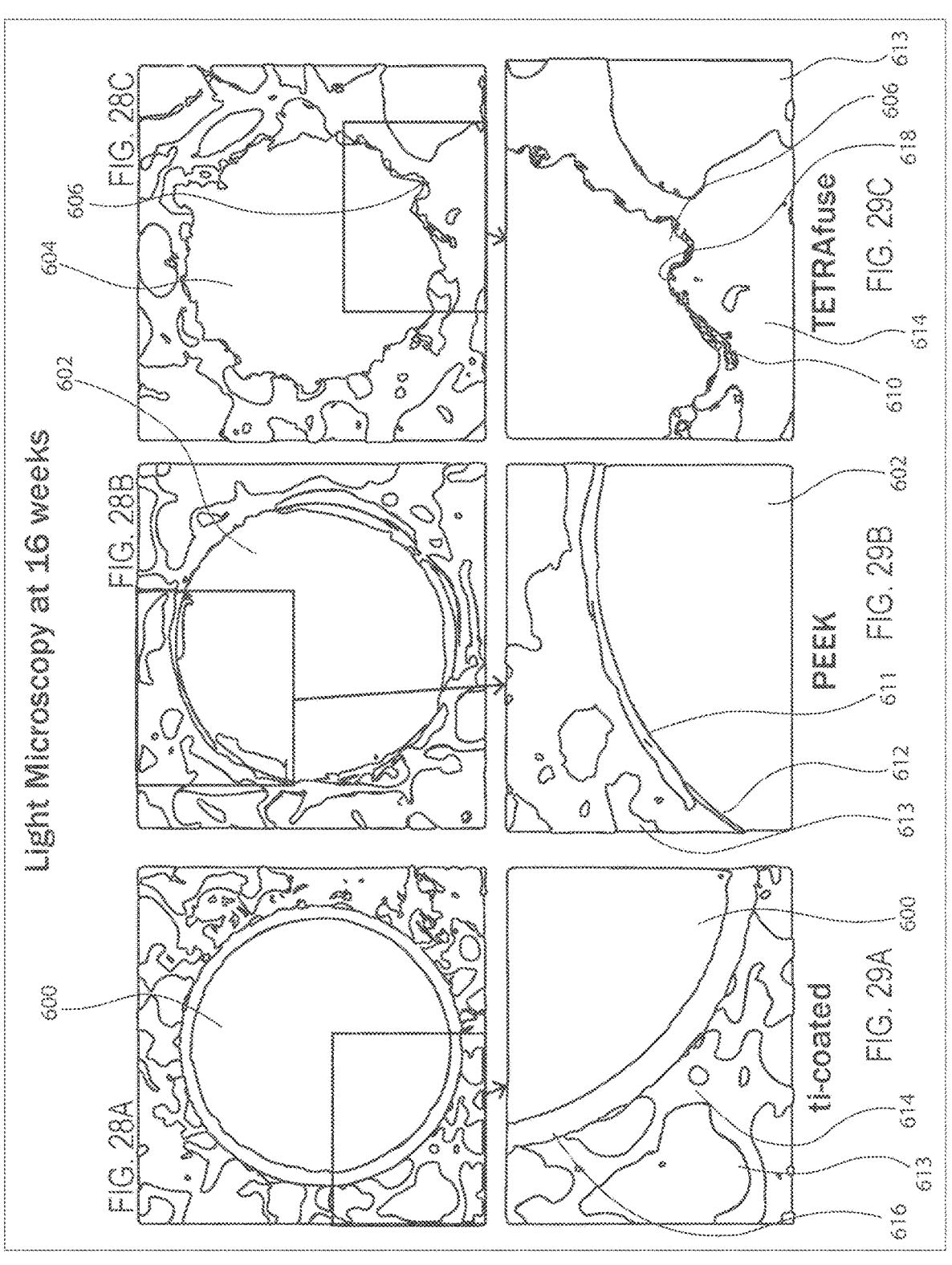

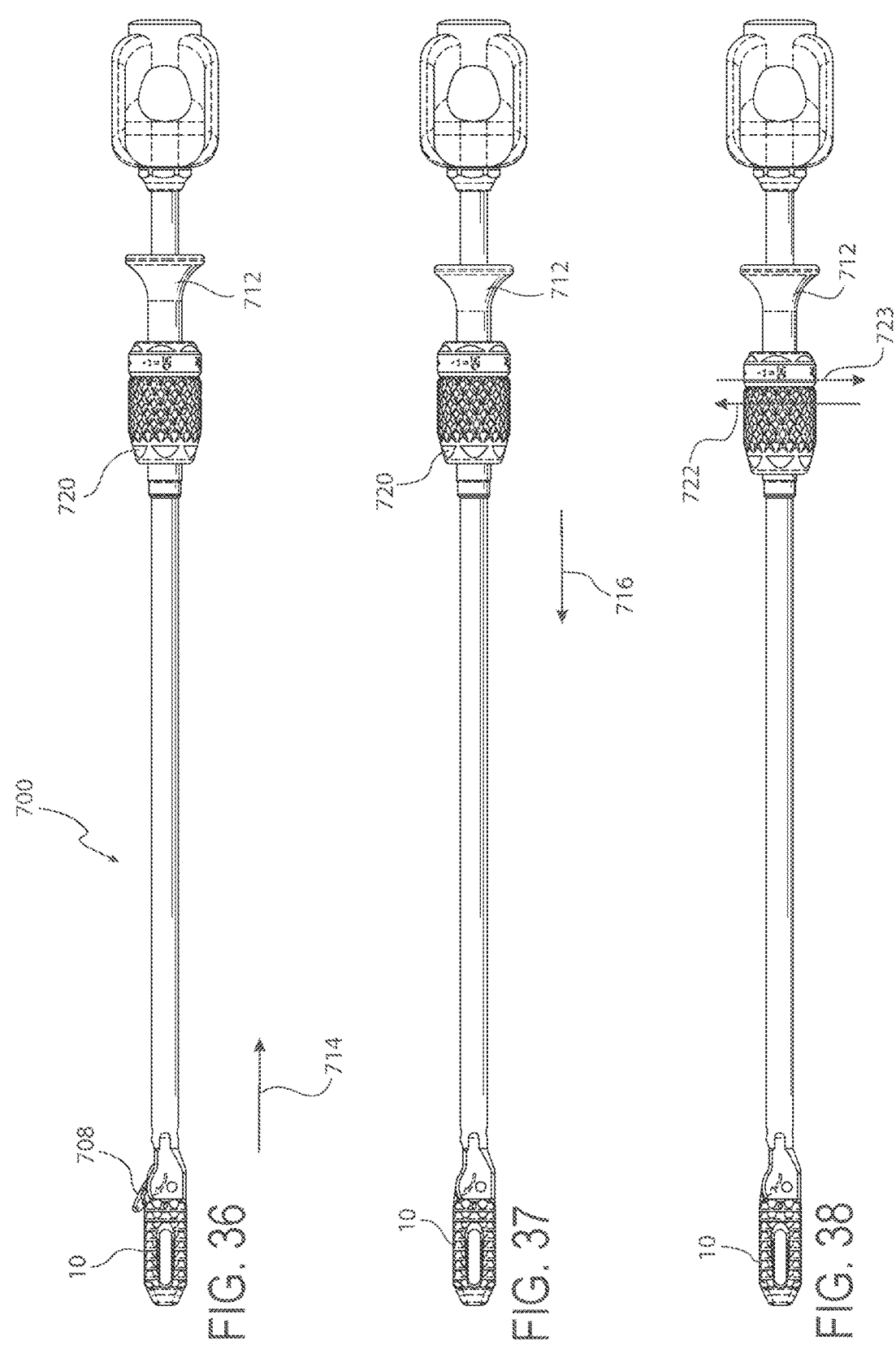

INTERVERTEBRAL IMPLANTS, INSTRUMENTS, AND METHODS

CROSS-REFERENCE TO RELATED APPLICATIONS

This application is a divisional of U.S. patent application Ser. No. 17/504,239, filed Oct. 18, 2021, which is a continuation of U.S. Non-provisional application Ser. No. 16/124,935, filed Sep. 7, 2018, now U.S. Pat. No. 11,147, 682, which claims the benefit of U.S. Provisional Patent App. No. 62/555,966, filed Sep. 8, 2017, which are all hereby incorporated by reference herein in their entireties.

FIELD

This disclosure relates generally to implantable medical devices and, more specifically, to implantable devices for intervertebral fusion and/or immobilization.

BACKGROUND

Many people develop back pain during their lifetimes due to injury, disease, or genetic defect. One source for back pain is if an intervertebral disc of a patient bulges outward from between the associated vertebrae. The bulging disc may impinge on the nerves of the spine and cause pain. To address this situation, a surgeon may trim the disc bulge or remove the disc entirely. The surgeon may then insert one or more implants to support and separate the vertebrae.

One type of implant used to support and separate vertebrae are interbody fusion devices ("IBDs"). IBDs often have a body with a large throughbore in which bone growth material can be packed to encourage bony ingrowth from the vertebrae and into the throughbore. One type of IBD is made of polyetheretherketone (PEEK). Although PEEK implants are radiolucent and do not obstruct x-ray viewing of the surgical site post-surgery, PEEK implants have been found to exhibit minimal amounts of bone growth onto the PEEK implant. PEEK IBDs may have a series of ridges in the throughbore that each extend continuously around the throughbore. These continuous ridges retain the bone growth material in the throughbore. The ridges extended continuously around the throughbore to maximize purchase with the bone growth material.

Another type of IBD is made of titanium-coated PEEK. The titanium coating has a roughened outer surface and encourages bone growth onto the implant. However, the titanium coating is radio-opaque and obstructs x-ray viewing of the surgical site post-surgery.

SUMMARY

In accordance with one aspect of the present disclosure, a spinal implant is provided for fusing vertebral bones. The spinal implant includes a monolithic body for being inserted between bones, a through opening of the body for receiving bone growth material, and a wall of the body extending about the through opening. The spinal implant further includes nubs of the wall extending into the through opening that increase the surface area of the wall available for bone on-growth. The increased surface area provides more area for bone to bond with the implant which increases the strength of the implant-vertebrae construct. The nubs of the wall also help retain the bone growth material within the through opening of the body which makes the implant easier to advance into the intervertebral space.

In one form, the monolithic body includes polyetherketoneketone (PEEK) and is fabricated using selective laser sintering. Fabricating the body by selective laser sintering PEEK produces rough surfaces of the body including surfaces of the nubs. For example, the rough surfaces of the body may have nanostructures that resemble peaks and valleys between the peaks, with an average peak-to-valley distance of approximately 125-129 nanometers and an average peak-to-peak distance of approximately 265-282 nanometers. It has been discovered that the combination of the increased surface area of the nubs and the roughness of the surfaces of the nubs encourages significant bone fusion interaction within the through opening of the body. Further, because the body is made from PEEK, the body is radiolucent to x-rays and permits a surgeon to view the surgical site post-surgery without obstruction by the implant body. This is an improvement over prior titanium-coated PEEK implants that are radio-opaque and obstruct viewing of the surgical site with x-rays. In this manner, the PEEK implant body provides both significant bone on-growth and a radiolucent implant for improving x-ray observation of the implant post-surgery.

In another aspect, an implant is provided for being inserted into an intervertebral space to stabilize vertebrae. The implant includes a monolithic body having a through opening for receiving bone growth material and an annular wall extending about the through opening. The annular wall is free of through apertures in communication with the through opening. In one embodiment, the monolithic body is made of PEEK and is fabricated using selective laser sintering. Although PEEK has a relatively high strength, PEEK becomes more brittle at narrow thicknesses. The absence of through apertures strengthens the annular wall of the body so that the annular wall can resist loading from the vertebrae after implantation, even at thin wall thickness such as 0.06 inches.

The body also includes an attachment member outward of the annular wall and recesses extending along opposite sides of the attachment member. The recesses are configured to receive clamping arms of an inserter tool. Because the inserter tool engages the implant by engaging the clamping arms with the attachment member, loading applied to the inserter tool such as by the surgeon moving the inserter tool in lateral directions is applied to the implant along opposite sides of the attachment member. Using opposite sides of the attachment member to receive loading from the inserter tool more evenly distributes loading from the inserter tool to the implant and minimizes stress concentrations on the implant due to the engagement with the clamping arms.

A spinal implant is also provided that includes a polymer body fabricated using additive manufacturing. The body has unmachined, irregular surfaces due to the body being fabricated by additive manufacturing. The irregular surfaces actively participate in bone on-growth which improves the strength of the engagement between the implant and bones. The body also includes a machined attachment portion for interfacing with an inserter tool. By machining the body, tight tolerances can be achieved for the attachment portion. The attachment portion has a surface roughness that is less rough than a surface roughness of the unmachined, irregular surfaces of the body. In this manner, the implant has both unmachined, irregular surfaces to encourage bone on-growth and a machined attachment portion with a reduced surface roughness that provides the high accuracy machined structures necessary to properly engage the inserter tool. In one embodiment, the plastic body is made of PEEK and is fabricated using selective laser sintering.

In accordance with another aspect of the present disclosure, a spinal implant system is provided that includes a spinal implant and an inserter tool. The spinal implant has a leading end portion, a trailing end portion, and a longitudinal axis extending therebetween. The tailing end portion includes an attachment member, and the attachment member has a boss extending axially outward from a trailing end surface of the attachment member. The inserter tool includes arms having a release configuration that permits the arms to be positioned on opposite sides of the attachment member and a gripping configuration wherein the arms clamp the attachment member therebetween. The inserter tool also includes a socket configured to engage the boss of the attachment member and increase the axial length of the engagement between the inserter tool and the implant. By increasing this axial length, the forces applied by the surgeon to the inserter tool as the surgeon manipulates the inserter tool (e.g., in the cephalad/caudal directions) is applied to the implant over a longer axial extent which more evenly distributes the forces and strengthens the connection between the implant and the inserter tool.

The present disclosure also provides a method of producing a spinal implant. The method includes fabricating a body of the spinal implant made of a polymer material using an additive manufacturing process. The body includes irregular outer surfaces having a first surface roughness produced by the additive manufacturing process. The method further includes machining the fabricated body to form an attachment portion of the body for interfacing with an inserter tool. The attachment portion has a second surface roughness that is less rough than the first surface roughness of the irregular outer surfaces of the body. The irregular outer surfaces of the fabricated body actively participate in bone on-growth which improves the strength of the engagement between the implant and bones. Further, by machining the fabricated body, tight tolerances can be achieved for the attachment portion. The method thereby provides a spinal implant having rougher irregular outer surfaces to encourage bone on-growth and a smoother attachment portion for precise engagement with an inserter tool.

In accordance with another aspect, a marker pin is provided for a spinal implant. The marker pin includes a body of a radiopaque material and a leading end portion of the body sized to fit into an opening of a body of a spinal implant. The body further includes an interference portion radially enlarged relative to the leading end portion and configured to engage the spinal implant body at a plurality of circumferentially spaced locations about the opening and retain the marker pin in the opening of the spinal implant body. Because the interference portion engages the spinal implant body at circumferentially spaced locations, there are undeformed portions of the spinal implant body separating localized deformations caused by the interference portion. This permits the marker pin to deform less of the material of the spinal implant body around the opening and makes the implant stronger.

BRIEF DESCRIPTION OF THE DRAWINGS

FIGS. 23, 24, and 25 are views showing the orientation of the implant bodies of FIGS. 20, 21, 22 during the selective laser sintering procedure;

FIG. 28A is a cross-sectional picture of a pin similar to the pins of FIG. 26 in bone showing the most pronounced bone attachment to the pin implant formed by selective laser sintering PEEK;

FIG. 28B is a cross-sectional picture of another pin similar to the pins of FIG. 26 in bone showing the most pronounced bone attachment to the pin implant formed by selective laser sintering PEEK;

FIG. 28C is a cross-sectional picture of yet another pin similar to the pins of FIG. 26 in bone showing the most pronounced bone attachment to the pin implant formed by selective laser sintering PEEK;

FIG. 29A is an amplified cross-sectional picture of the pin shown in FIG. 28A;

FIG. 29B is an amplified cross-sectional picture of the pin shown in FIG. 28B;

FIG. 29C is an amplified cross-sectional picture of the pin shown in FIG. 28C;

FIG. 36 is a top plan view of the inserter tool of FIG. 31 and the implant of FIG. 2 showing the adjustment knob in a release position and the lock knob in an unlocked position;

FIG. 37 is a top plan view similar to FIG. 36 showing the adjustment knob in a gripping position and the lock knob in an unlocked position;

FIG. 38 is a view similar to FIG. 37 showing the lock knob turned to a locked position;

DETAILED DESCRIPTION

Figure 1:
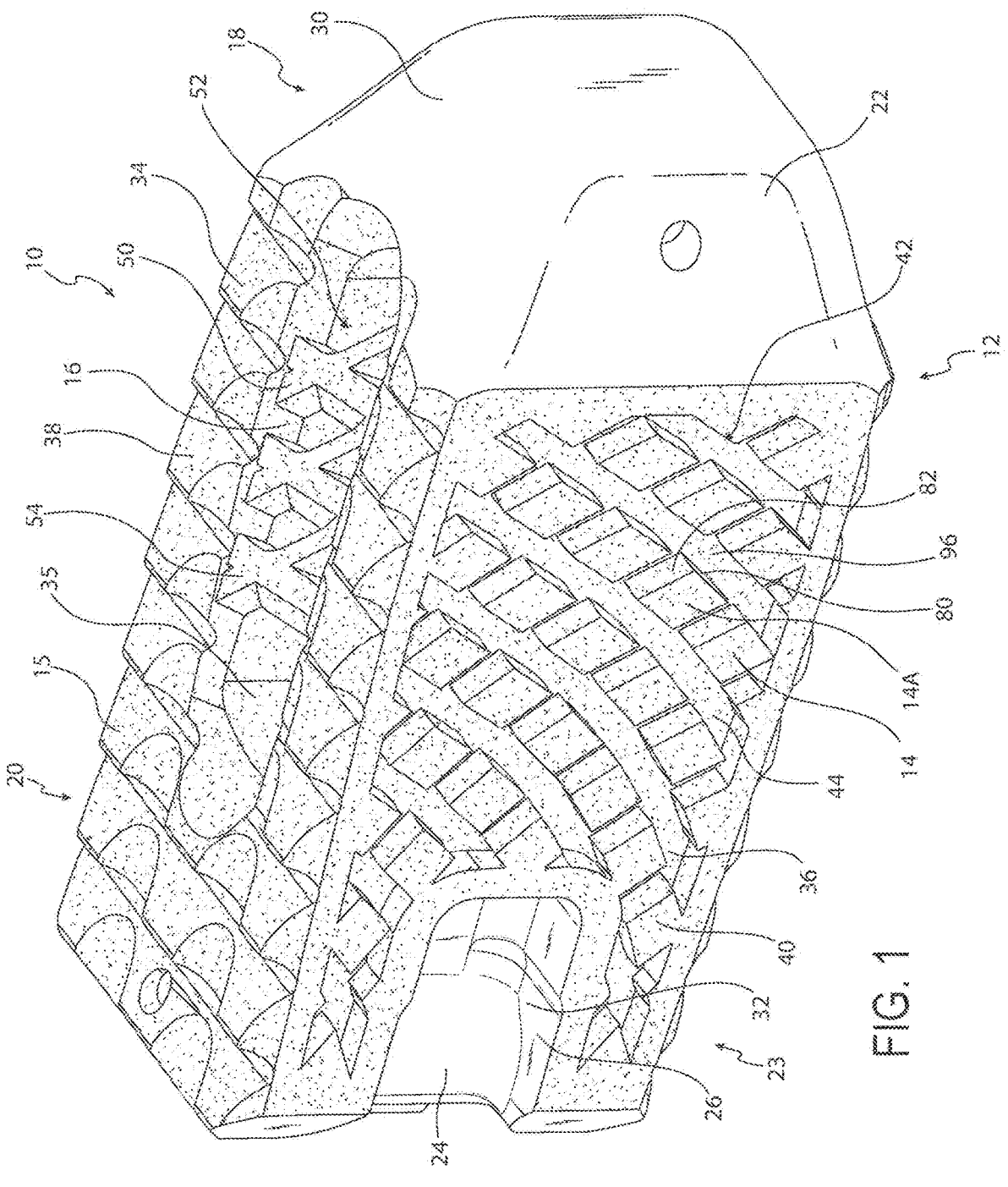
FIG. 1 is a perspective view of an implant showing rough, irregular surfaces of the implant formed by fabricating the implant by selective laser sintering PEEK and smoother surfaces of the implant formed by machining portions of the body.

With reference to FIG. 1, an implant 10 is provided for stabilizing vertebrae. The implant 10 has a body 15 that may be made of a plastic, such as polyetherketoneketone (PEEK), and may be fabricated using a 3D printing or additive manufacturing process, such as selective laser sintering. The fabrication of the implant 10 by selective laser sintering PEEK creates rough surfaces 12 of the body 15 due to the granule powder size and resolution of the selective laser sintering process. The rough surface texture of the rough surfaces 12 is indicated by stippling in the drawings. The rough surfaces 12 have nanostructures that resemble peaks and valleys between the peaks, with an average peak-to-valley distance of approximately 125-129 nanometers and an average peak-to-peak distance of approximately 265-282 nanometers. These parameters were measured using an XE7 atomic force microscope having a non-contact cantilever probe (from Park Systems of South Korea) with a force constant of 42 Nim, a scan size of 1×1 micrometer, and a scan frequency of 0.5 Hz.

The rough surface also includes micro-size pores having an average pore diameter in the range of approximately 500 micrometers to approximately 600 micrometers, such as approximately 530 micrometers. Further, the implant 10 has nubs 14 and 16 that are macro-size structures which increase the surface area of the surfaces 12 of the implant 10. The combination of the rough exterior surfaces 12 and the nubs 14, 16 results in deeper implant osseointegration than if the implant were made of PEEK or titanium plasma coated PEEK, as discussed in greater detail below. In other words, the rough exterior surfaces 12 and nubs 14, 16 allow more bone cells to attach to more of the implant 10.

The implant body 15 has a leading end portion 18 and a trailing end portion 20. The leading end portion 18 includes a tapered nose 22 and the trailing end portion 20 includes an attachment portion 23 including an attachment member 24 and recesses 26, 28. The body 15 may be machined after being fabricated to create the features of the nose 22, attachment member 24, and recesses 26, 28 in the body 15. The term machined is intended to mean that the implant is secured and a moving cutting member is brought into contact with the implant to remove material from the body of the implant. Machining can include, but is not limited to, CNC machining including mills and turning centers. Machining the body 15 to form the nose 22 forms smooth surfaces 30 of the nose 22 and machining the body 15 to form the attachment member 24 and recesses 26, 28 creates smooth surfaces 32. The smooth surfaces 30 of the nose 22 make it easier to advance the implant 10 into an intervertebral space. The smooth surfaces 30, 32 have a surface roughness approximately 30-60 roughness average or 30-65 root mean squared, compared to the unmachined surfaces 12 having a surface roughness in the range of 900 to 1100 roughness average, such as approximately 1000 roughness average (approximately 1100 root mean squared). The machining thereby smooths out the irregularities that create the rough surfaces 12 produced by selective laser sintering PEEK.

Machining the attachment member 24 and recesses 26, 28 into the body 15 provides high accuracy for the geometry of the attachment member 24 and recesses 26, 28 that may not be possible by selective laser sintering PEEK. High accuracy of the attachment member 24 and recesses 26, 28 provides desired tolerances so that the attachment member 24 may be properly secured to an inserter tool. In this manner, the implant 10 combines the rough surfaces 12 from fabricating of the body 15 that improve bone on-growth to the implant 10, the high-accuracy geometry of the attachment member 24 and recesses 26, 28 which allow the implant 10 to be securely grasped by an inserter tool, and the smooth profile of the nose 22 to improve insertion of the implant 10.

Figure 2:
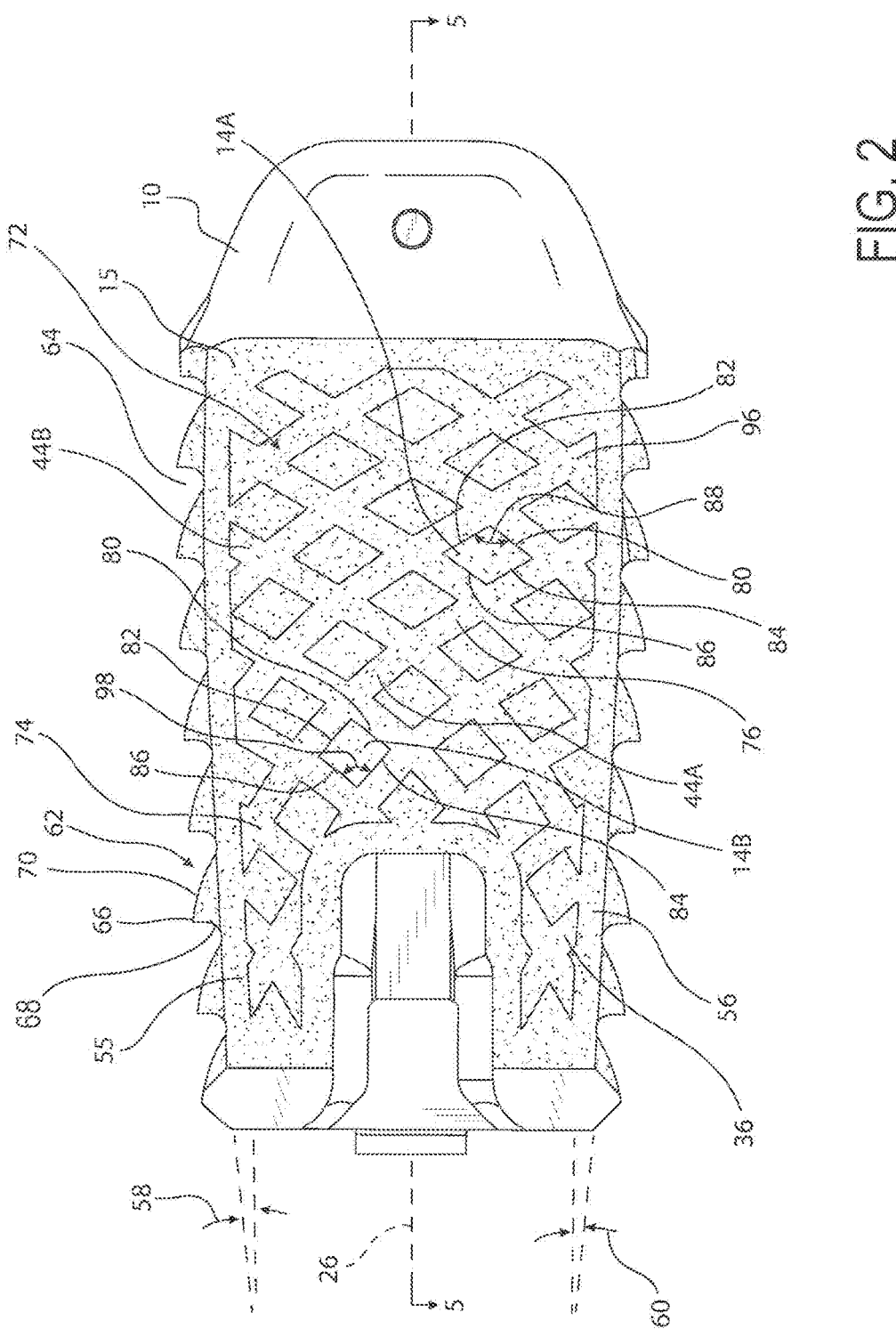
FIG. 2 is a side elevational view of the implant of FIG. 1 showing a pattern of nubs and pathways on a side of the implant.
Figure 3:
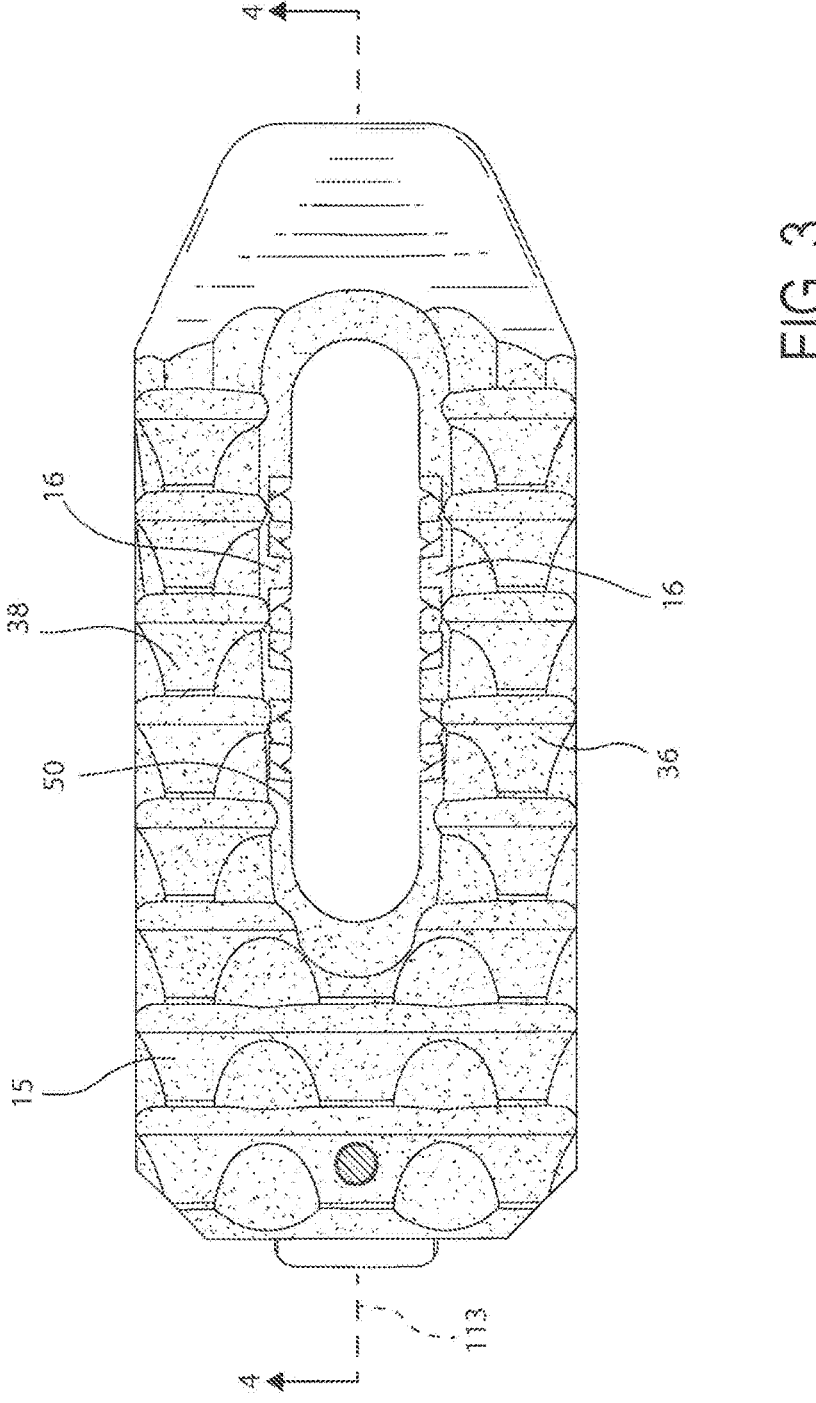
FIG. 3 is a top plan view of the implant of FIG. 2 showing an annular wall of the implant extending around a through opening of the implant for receiving bone growth material.

With reference to FIGS. 1 and 2, the body 15 includes an annular wall 34 encircling a compartment, such as formed by a through opening 35, for receiving bone growth material. The bone growth material may include autograph, allograph, allogenic bone graft, demineralized bone matrix, hydroxyapatite. The annular wall 34 includes lateral wall portions 36, 38 spaced apart from each other on opposite sides of the through opening 35. The lateral wall portions 36, 38 have an outer surface 40 with a pattern 42. The pattern 42 includes the nubs 14 and pathways 44 between the nubs 14. The nubs 14 increase the surface area of the outer surface 40 for bone to grow onto. The pathways 44 provide spaces for bone to grow along the outer surfaces 40 of the lateral walls portions 36, 38.

The lateral wall portions 36, 38 each have an inner surface 50 with a pattern 52 that includes the nubs 16 and pathways 54 as shown in FIG. 1. The nubs 16 increase the surface area of the inner surface 50 for on-growth of bone and assist in the retention of the bone growth material within the though opening 35 during installation of the implant 10 between adjacent vertebrae. The pathways 54 provide spaces between the nubs 16 through which bone growth material is packed and retained as the surgeon packs the through opening 35 with bone growth material.

Further, after the body 15 has been fabricated by selective laser sintering PEEK, the body 14 can be low pressure blasted to remove excess PEEK leftover from the selective laser sintering process. The leftover PEEK on the body 15 resembles hardened clumps of sand that is broken off from the body 15. The low pressure blasting may involve pressures less than 20-100 pounds per square inch, such as 50 pounds per square inch, and may utilize glass, bead, sand, and/or dry ice particles as the blasting medium. The pathways 54 permit particles from the low pressure blast process process to travel along the inner surface 50 and remove leftover PEEK from the inner surface 50. For example, with reference to FIG. 4, the low pressure blasting particles can travel in direction 104 through the pathway 54A. This allows the low pressure blasting particles to remove debris from difficult-to-reach portions of the inner surface 50, such as the undersides of the nubs 16. In this manner, the pathways 54 make it easier to clean the body 15 after fabricating the body 15.

With reference to FIG. 2, the annular wall 34 includes an upper bone engaging portion 55 and a lower bone engaging portion 56. The upper and lower bone engaging portions 55, 56 may be oriented to have angles 58, 60 of zero to eighteen degrees so that the upper and lower bone engaging portions 55, 56 match the patient's anatomy. The upper and lower bone engaging portions 55, 56 may thereby taper toward each other as the body 15 extends from the nose 22 to the attachment member 24. The upper and lower bone engaging portions 55, 56 include gripping members 62 separated by recesses 64. The gripping members 62 each have a peak 66 at which a trailing surface 68 and a leading surface 70 meet. The peak 66 may be sharp to engage the end plates of the vertebrae. The gripping members 62 may have various shapes, such as saw teeth, sine wave, pyramids, curved teeth, etc.

The pattern 42 extends from the upper bone engaging portion 55 to the lower bone engaging portion 56 along the outer surfaces 40 of each of the lateral wall portions 36, 38. The pathways 44 form a lattice pattern 72 as shown in FIG. 2. The lattice pattern 72 includes crisscrossing pathways 44 such as pathway 44A and pathway 44B that each extend from the upper bone engaging portion 55 to the lower bone engaging portion 56. The pathways 44A, 44B may have a variety of shapes including linear and non-linear. For example, the pathway 44A may have a first pathway portion 74 and a second pathway portion 76 that extend transversely to each other. One or more of the pathways 44 may be curved or have a portion that is curved.

The crisscrossing pathways 44 can define the general shape of the nubs 14. In one form, the nubs 14 have a diamond-like shape. With respect to nub 14A, the nub 14A has a continuous peripheral outer surface extending thereabout including sides 80, 82, 84, 86. The pairs of sides 80, 82 and 84, 86 are each oriented at angles 88 relative to each other. The shape of the nubs 14 may change throughout the pattern 42. For example, the nub 14B has sides 80, 82, 84, 86 and each pair of sides 80, 82, and 84, 86 are oriented at angles 98 that are smaller than the angles 88. The nub 14A therefore appears elongated while the nub 14B more resembles a square. With reference to FIGS. 1 and 2, the sides 80, 82, 84, 86 of the nubs 14 extend outward from base surfaces 96 of the pathways 44 generally perpendicular to the base surfaces 96.

Figure 4:
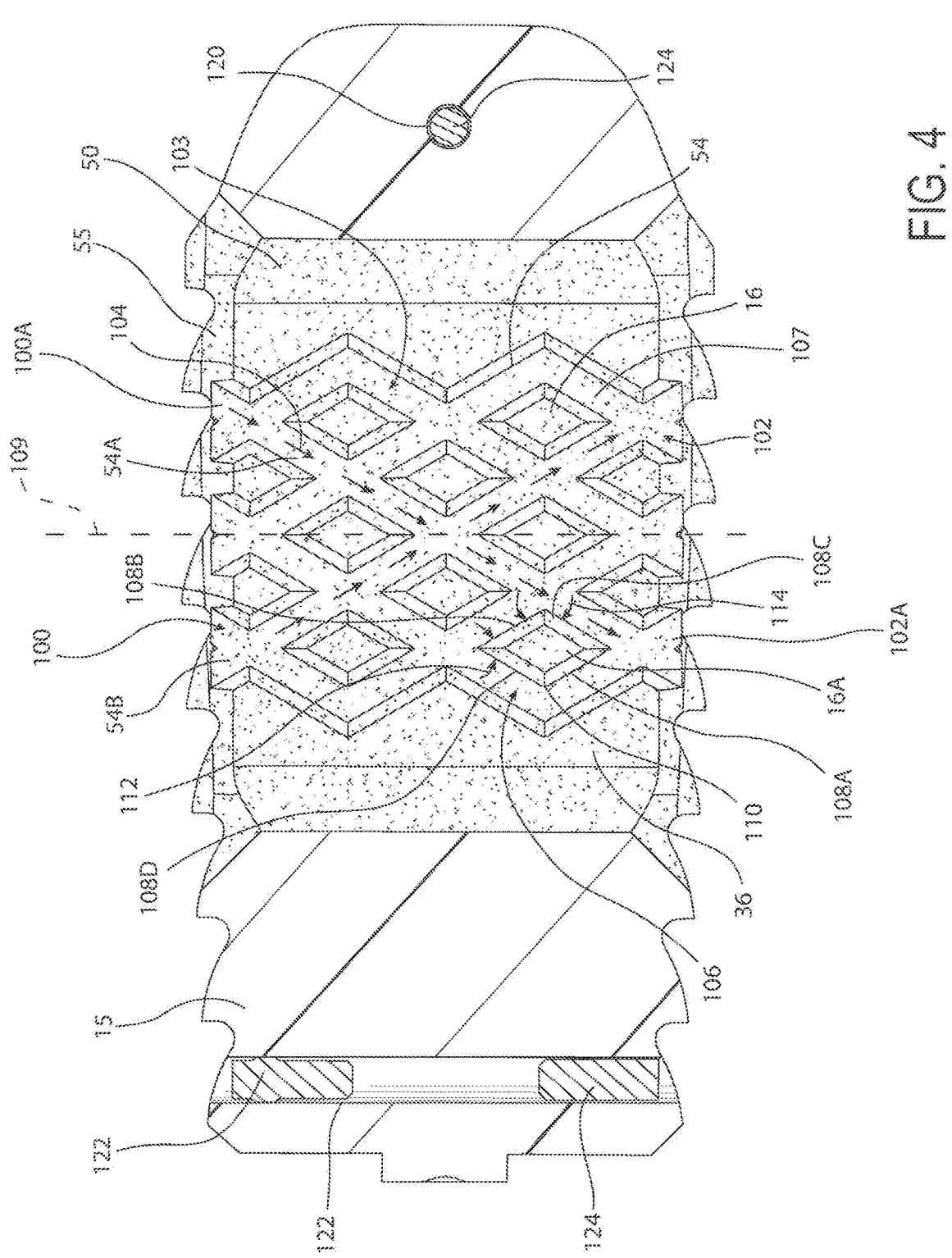
FIG. 4 is a cross-sectional view taken across line 4-4 in FIG. 3 showing a pattern of nubs and pathways on an inner surface of a wall of the implant.

With reference to FIG. 4, the pattern 52 on the inner surface 50 of each of the lateral wall portions 36, 38 includes the nubs 16 and pathways 54. The pathways 54 include openings 100 at the upper bone engaging portion 55 and openings 102 at the lower bone engaging portion 56. The pattern 52 includes recessed base surfaces 107 separating the nubs 16. Due to the openings 100, 102, the recessed base surfaces 107 extend all the way between the top and bottom of the body 15. The base surfaces 107 and nubs 16 define the pathways 54. For example, the pathway 54A extends from the opening 100A to the opening 102A. The pathway 54A permits bone growth material to move in the through opening 35 in direction 104 between the nubs 16. The pathways 54 intersect each other and form a lattice 103 of crisscrossing or intersecting pathways 54. For example, the pathway 54B extends from the upper bone engaging portion 55 to the lower bone engaging portion 56 and intersects the pathway 54A. The intersecting pathways 54 define the general shape of the nubs 16. The nubs 16 each have a continuous peripheral surface 106 that extends from the base surface 107 of the pathways 54. The peripheral surface 106 of each nub 16 is completely spaced from the peripheral surface 106 of the surrounding nubs 16. The nubs 16 are localized protrusions that extend into the through opening 35 from the base surfaces 107 of the pathways 54.

With reference to nub 16A, the peripheral surface 106 of the nub 16A includes side surfaces 108A, 108B, 108C, 108D that are interconnected by corner edges 110. The side surfaces 108B, 108D are oriented to extend to an angle 112 relative to one another, and the side surfaces 108A, 108C are oriented to extend at an angle similar to angle 112. The side surfaces 108B, 108C are oriented to extend at an angle 114 relative to one another and the side surfaces 108A, 108D are oriented to extend at an angle similar to angle 114. The angle 114 is larger than the angle 112 such that the nub 16A is elongated along a vertical axis 109 of the body 15. The angle 112 may be approximately 60 degrees and the angle 114 may be approximately 120 degrees. The side surfaces 108A-108D may each extend obliquely into the through opening 35 relative to the base surfaces 107 of the pathways 54. This provides a more tapered profile of the nubs 16 as the nubs 16 extend at an incline into the throughbore 35 than the nubs 14. The obliquely inclined side surfaces 108A-108D may function as ramps to direct debris off of the nubs 16 during low pressure blasting of the body 15 after the body 15 has been fabricated using selective laser sintering. This makes the body 15 easier to clean after fabrication.

Figure 5:
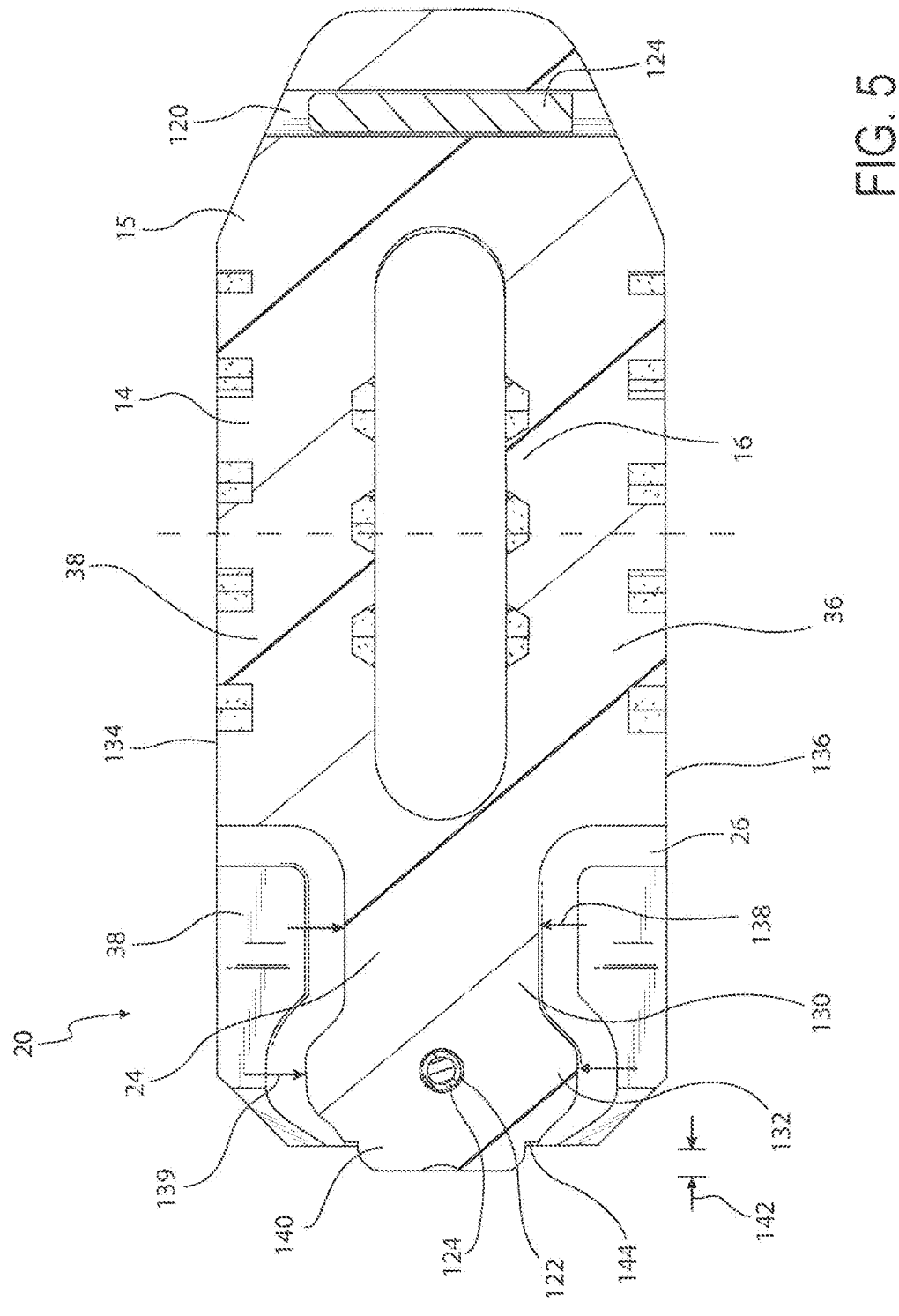
FIG. 5 is a cross-sectional view taken across line 5-5 in FIG. 2 showing an attachment member for being clamped between arms of an inserter tool.
Figure 6:
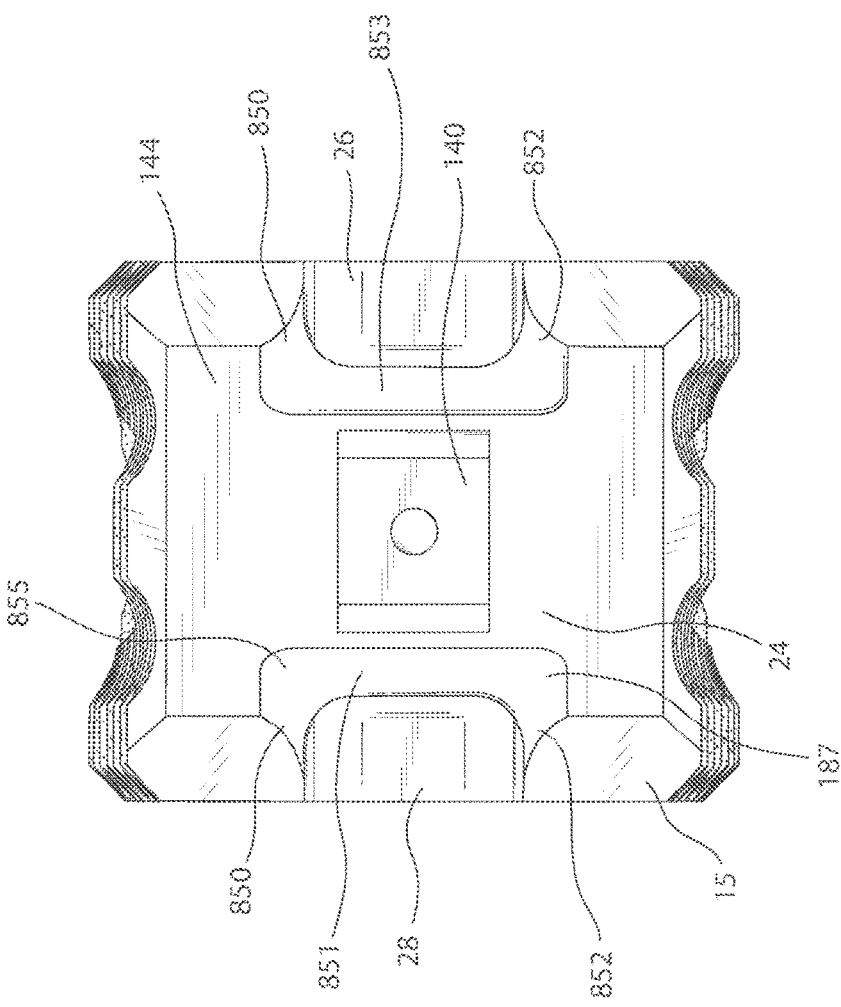
FIG. 6 is a rear elevational view of the implant of FIG. 2 showing recesses on opposite sides of the attachment member that receive the inserter tool arms.

With reference to FIGS. 5 and 6, the trailing end portion 20 includes the attachment member 24 and recesses 26, 28 on opposite sides of the attachment member 24. The recesses 26, 28 receive arms of an inserter tool. The attachment member 24 has a neck portion 130 and a head portion 132. The neck portion 130 is recessed from lateral sides 134, 136 of the lateral wall portions 36, 38. The head portion 132 and neck portion 130 permit the inserter tool arms to be received so that their outer surfaces are laterally inward from or flush with the lateral sides 134, 136. Because the inserter tool arms are inward from or flush with the lateral sides 134, 136, the inserter tool arms avoid becoming caught on tissue or bone as the implant 10 is advanced into the intervertebral space.

The neck portion 130 can have a width 138 of approximately 0.170 inches and the head portion 132 can have a width 139 of approximately 0.240 inches such that the head portion 132 is enlarged relative to the neck portion 130. The width 138 may be in the range of approximately 0.118 inches to approximately 0.197 inches and the width 139 may be in the range of approximately 0.197 inches to approximately 0.276 inches. The ratio of the width 139 to the width 138 may be in the range of 1.1 to 2.4, such as 1.3 to 2.0, and may be approximately 1.4. The head portion 132 and neck portion 130 provide a thick, block-like structure for the inserter tool arms to engage and grab. The overall width of the implant 10 between the sides 134, 136 may be approximately 0.394 inches.

The attachment member 24 also includes a boss 140 extending longitudinally for a distance 142 from a trailing end surface 144 of the attachment member 24. The trailing end surface 144 may be flat, and the boss 140 may have a generally cuboid shape that extends rearward from the trailing end surface 144. The boss 140 operates as a plug that fits within a socket of the inserter tool (see FIG. 35) to increase the length of the engagement between the implant 10 and the inserter tool. This improves the strength of the connection between the implant 10 and the inserter tool by providing better torque resistance as discussed in greater detail below.

With reference to FIG. 6, the implant body 15 includes ceilings 850, floors 852, and lateral sides 851, 853 of the attachment member 24 defining the recesses 26, 28. The body 15 includes corners 855, 857 connecting the ceilings 850 and floors 825 to the lateral sides 851, 853. The corners 855, 857 are relatively sharp, such as 90 degrees. By machining the PEEK material, the corners 855, 857 of the implant attachment portion 23 can be formed with tight tolerances. Further, the somewhat U-shaped recesses 26, 28 extending laterally inward into the body 15 as shown in FIG. 6 provide pockets to receive the arms of an inserter tool with the outer surfaces of the arms laterally inward from or flush with the lateral sides of the implant 10.

Figure 7:
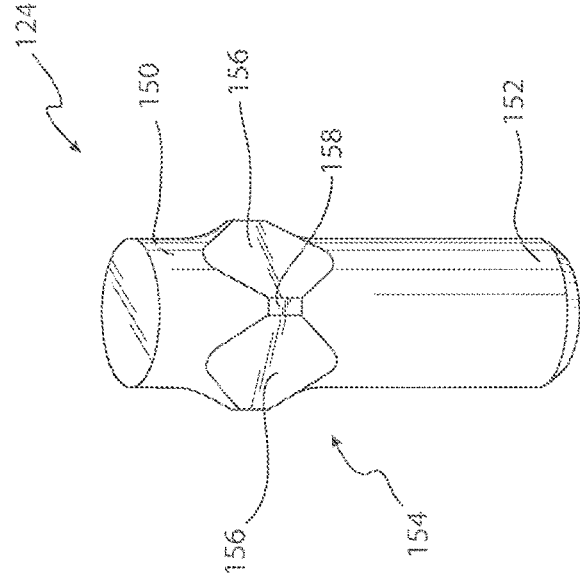
FIG. 7 is a perspective view of a marker pin of the implant of FIG. 2 showing flats and edges of the marker pin.

With reference to FIGS. 4 and 5, the body 15 includes through apertures 120, 122 for receiving marker pins 124. The marker pins 124 may be radiolucent to indicate the orientation of the implant 10 during x-ray imaging of the surgical site. Turning to FIG. 7, each marker pin 124 may have a trailing end portion such as an upper end portion 150, a leading end portion such as a lower end portion 152, and an interference portion such as an enlarged portion 154 intermediate the upper and lower end portions 150, 152. The enlarged portion 154 has a larger radius than the apertures 120, 122 to be in interference therewith.

The upper and lower portions 150, 152 have a circular cross-section and the enlarged portion 154 has a non-circular cross-section, such as a polygonal cross-section such as the illustrated generally rectangular cross section. As illustrated, the enlarged portion 154 includes flats 156 and corner junctures or edges 158 which connect the flats 156. When the marker pins 124 are received in the body apertures 120, 122, the edges 158 engage the surfaces about the apertures 120, 122 to deform the material of the body 15 and fix the marker pin 124 within the apertures 120, 122. By deforming the material of the body 15 with the edges 158, the marker pin 124 deforms a smaller portion of the body around the apertures 120, 122 which reduces the likelihood of the body 15 fracturing around the apertures 120, 122. Using the edges 158 to locally deform the material of the body 15 provides reduced stress in the body 15 in comparison to a cylindrical marker pin having a diameter larger than the apertures 120, 122 that is press fit into the apertures 120, 122 and engages the body 10 around the entire circumference of the marker pin.

Figure 8:
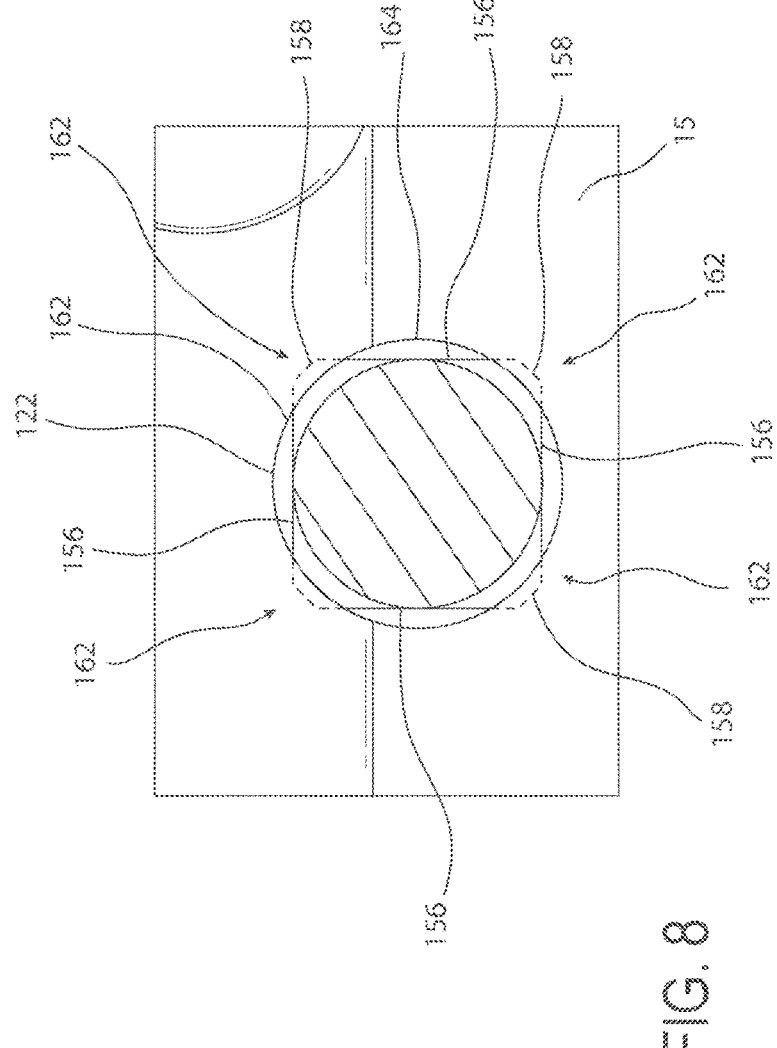
FIG. 8 is a top plan view of the marker of FIG. 7 in an opening of the implant of FIG. 2 and the edges of the marker pin engaging a body of the implant at spaced locations around the opening.

For example and with reference to FIG. 8, the through bore 122 has an opening surface 160 extending around the opening 122. As the marker pin 124 is advanced into the opening 122, the edges 158 bite into the surface 160 and create localized deformations 162 of the body 15 at each of the edges 158. Because the marker pin 154 has flats 156 separating the edges 158, the implant body 15 has undeformed portions 164 separating the localized deformations 162. By deforming less of the area of the opening surface 160, the implant 15 is stronger due to the reduced stress in the material of the body 15 surrounding the apertures 120, 122.

As noted above, PEEK is more brittle than PEEK at smaller features such as relatively thin wall portions 36, 38. To increase the strength of the annular wall 34, the annular wall 34 is free of through apertures in communication with the through opening 35 that extend between the inner and outer surfaces 40, 50 and would otherwise cause stress concentrations in the annular wall 34. The annular wall 34 is therefore stronger in compression which makes the implant 10 more durable. Through apertures are often used in the walls of PEEK implants to permit bone growth through the aperture. Although the annular wall 34 lacks through apertures that permit bone growth therethrough, the rough exterior surfaces 12 and the nubs 14, 16 provide significant implant osseointegration without through apertures.

Figure 9:
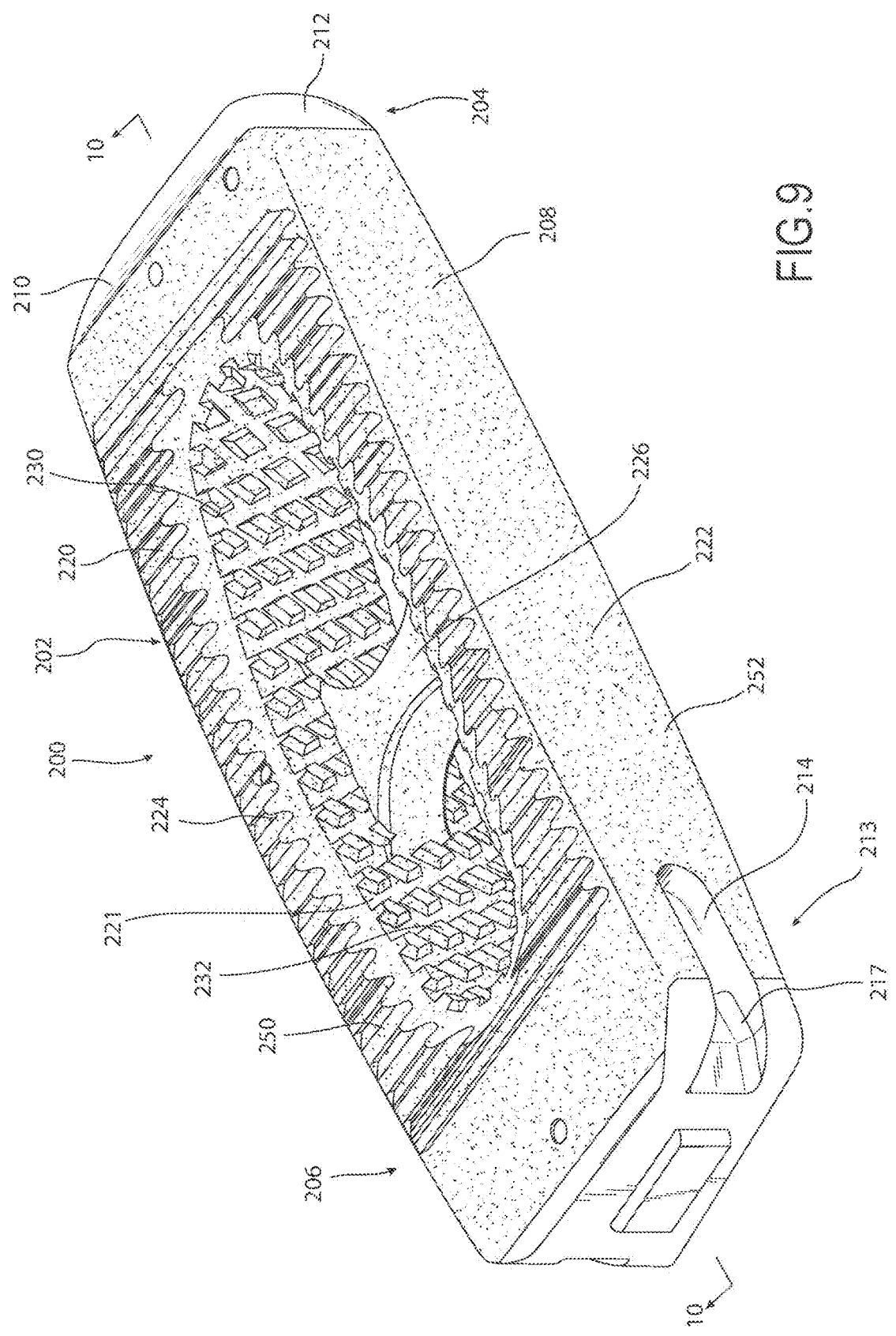
FIG. 9 is a perspective view of another implant showing rough, irregular surfaces of the implant formed by fabricating the implant by selective laser sintering PEEK and smoother, machined surfaces of the implant.

With reference to FIG. 9, an implant 200 is provided that a similar in many respects to the implant 10 discussed above such that differences between the implants 10, 200 will be highlighted. The implant 200 includes a body 202 having a leading end portion 204 and a trailing end portion 206. The body 202 may be formed by selective laser sintering PEEK and has rough, unmachined surfaces 208. The trailing end portion 206 includes an attachment portion 213 including an attachment member 215 and recesses 214, 216 on opposite sides of the attachment member 215. The nose 210 and attachment portion 213 are machined into the body 202 after the body 202 has been fabricated such that the nose 210 and attachment portion 213 have smooth, machined surfaces 212, 217.

With reference to FIG. 9, the body 202 includes an annular wall 220 extending around a compartment, such as a through opening 221. The through opening 221 receives bone growth material. The annular wall 220 includes lateral side walls 222, 224 and the body 202 includes a web 226 extending between the lateral side walls 222, 224. The annular wall 222 has an inner surface 230 defining at least a portion of the through opening 221. The inner surface 230 includes nubs 232.

Figure 10:
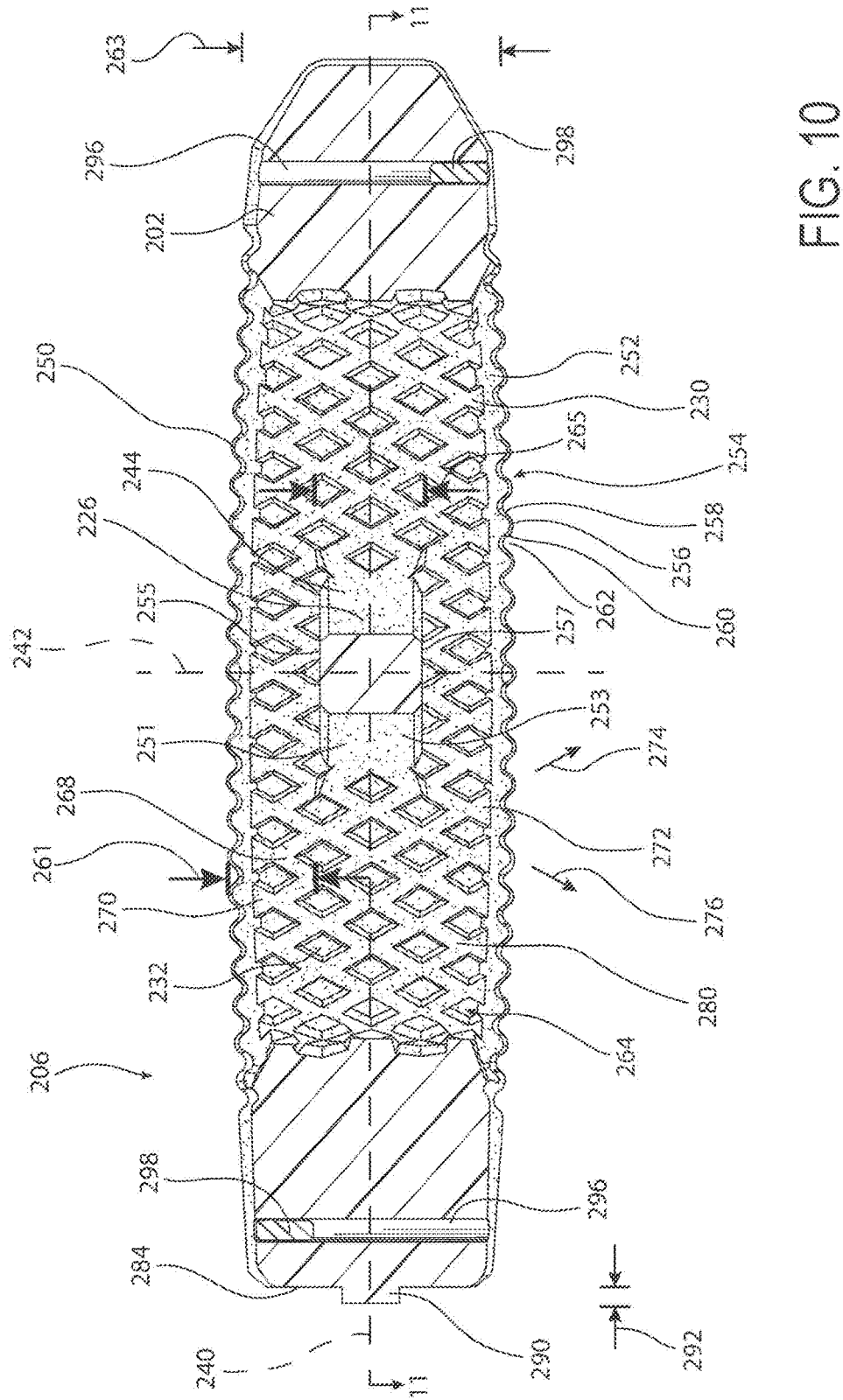
FIG. 10 is a cross-sectional view of the implant taken across line 10-10 in FIG. 9 showing a pattern of pathways and nubs on an inner surface of the implant.
Figure 11:
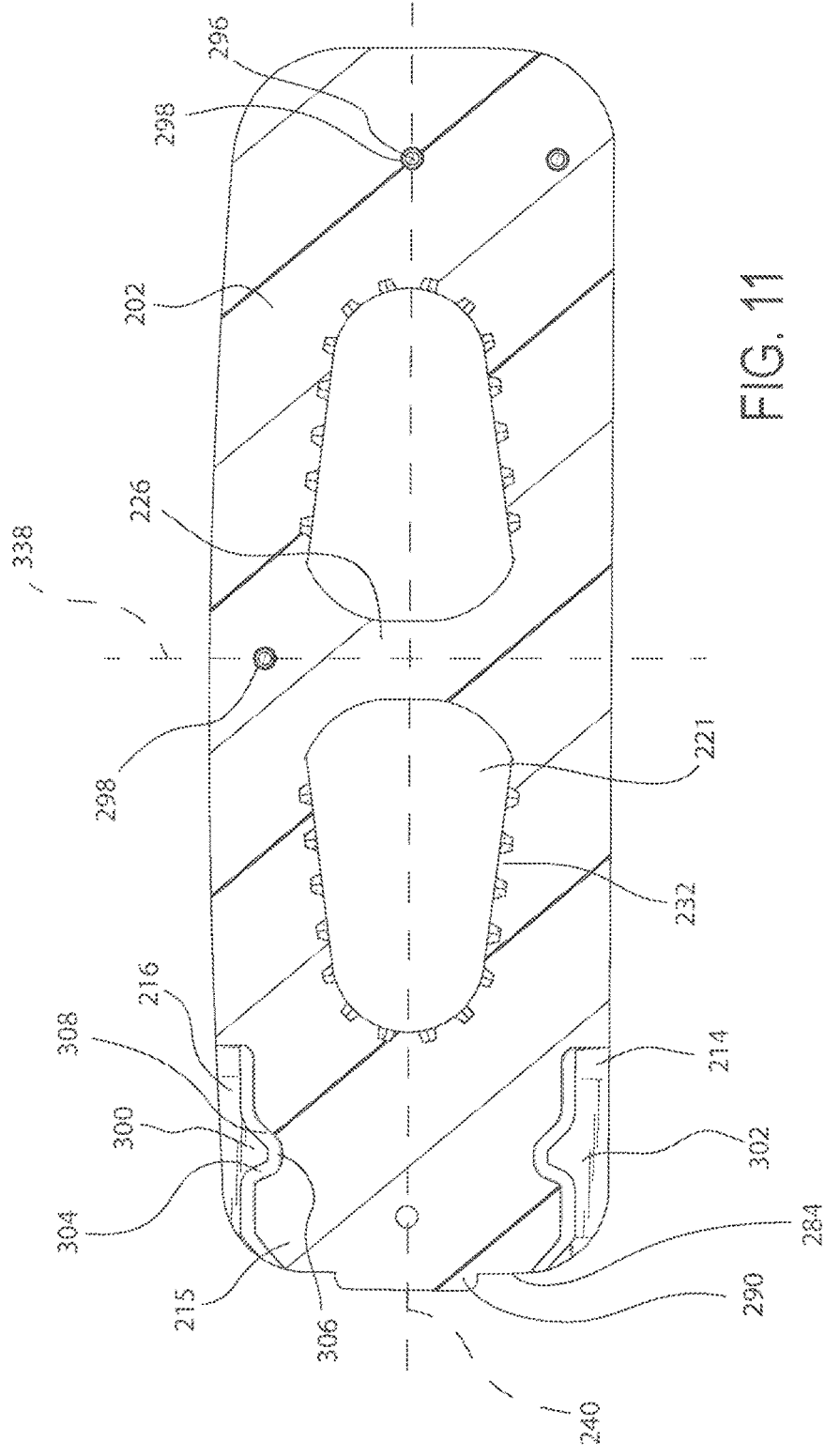
FIG. 11 is a cross-sectional view taken across line 11-11 in FIG. 10 showing a web of the implant extending across a through opening of the implant.

With reference to FIGS. 10 and 11, the implant 200 includes a longitudinal axis 240, a vertical axis 242, and a lateral axis 338. The web 226 extends across the through opening 221 transverse, such as perpendicular, to axes 240, 242 and along the lateral axis 338. The web 226 has a base 244 that tapers outwardly as the web 226 reaches the inner surface 230 at each of the lateral side walls 222, 224. The annular wall 220 includes an upper bone engaging portion 250 and a lower bone engaging portion 260. The upper and lower bone engagement portions 250, 252 include gripping members 254 that each have a peak 256, a leading surface 258, and a trailing surface 260. The upper and lower bone engaging portions 250, 252 include recesses 262 between the gripping members 254. The peaks 256 may be rounded and the leading and trailing surfaces 258, 260 may also be rounded to form an undulating surface of the upper and lower bone engaging portions 250, 252.

The web 226 has an uppermost portion 251 and a lowermost portion 253 that include, respectively, a top surface 255 and a bottom surface 257. The uppermost and lowermost portions 251, 253 are recessed relative to the upper and lower bone engaging portions 250, 252. Because the uppermost and lowermost portions 251, 253 of the web 226 are recessed, the web 226 avoids contacting bones during insertion of the implant 200 into an intervertebral space between the bones. This reduces the surface area of the implant 200 that can contact the bones and resist advancing of the implant 200 into the intervertebral space. If the body 202 is fabricated by selective laser sintering PEEK, the body 202 may be more brittle than an implant milled from a block of PEEK. The recessed web 226 may reduce the resistance to advancing the implant 200 such that the surgeon may apply less force to the implant 200 via an inserter tool.

The web 226 may have a rectangular cross-section taken normal to the lateral axis 338 and the web 226 has top and bottom surfaces 255, 257 that may be flat or rounded. The top and bottom surfaces 255, 257 extend from one lateral side wall 222, 224 to the other. The top and bottom surfaces 255, 257 of the web 226 may each be spaced from the peaks 256 of the gripping members 254 of the respective upper and lower bone engaging portions 250, 252 by a distance 261. The implant 200 may be provided in various heights 263 and the web 226 has a height 265 that may be the same for different heights 263 of the implant 200. Thus, the distance 261 may be greater for taller implants 200 than for implants 200 with shorter heights 263.

With reference to FIG. 10, the annular wall 220 includes a pattern 264 and includes the nubs 232 and intersecting or crisscrossing pathways 268 that form a lattice. The pathways 268 include openings 270 at the upper bone engaging portion 250 and openings 272 at the lower bone engaging portion 252. The pathways 268 permit low pressure blasting particles to travel therethrough and remove debris left on the nubs 232 from fabrication of the body 202. The pathways 268 also permit bone growth material to travel between the nubs 232 as the bone growth material is packed into the through opening 221. The nubs 232 have a shape similar to the nubs 16 discussed above and extend inwardly from base surfaces 280 of the pathways 268. The nubs 232 therefore increase the surface area of the inner surface 230 of the annular wall 220 to improve bone on-growth. The nubs 232 also operate to retain bone growth material in the through opening 221.

With reference to FIGS. 10 and 11, the trailing end portion 206 includes a substantially flat trailing end surface 284 and the attachment member 215 includes a rectangular boss 290 that extends longitudinally outward from the trailing end surface 284 a distance 292. The boss 290 forms a plug-fit engagement with a socket of an inserter tool as discussed in greater detail below with reference to FIG. 42. The boss 290 increases the longitudinal length of engagement between the inserter and the implant 200 to distribute loading from the inserter to the implant 200 over a larger portion of the implant 200 which limits stress concentrations in the body 202. The leading and trailing end portions 204, 206 also include bores 296 for receiving marker pins 298.

With reference to FIG. 11, the attachment member 215 includes secondary recesses, such as cavities 300, 302, for receiving projections of arms of an inserter tool. The attachment member 215 includes walls 304, 306, 308 that define the cavities 300, 302. The wall 304 on each side of the attachment member 215 is oriented to extend transverse to the longitudinal axis 240 such that the engagement between the inserter tool arms and the walls 304 cams the attachment member 215 toward the inserter tool as the arms clamp the attachment member 215 therebetween. In this manner, the more tightly the arms of the inserter clamp the attachment member 215, the more the implant 200 is urged proximally into the inserter tool.

Figure 12:
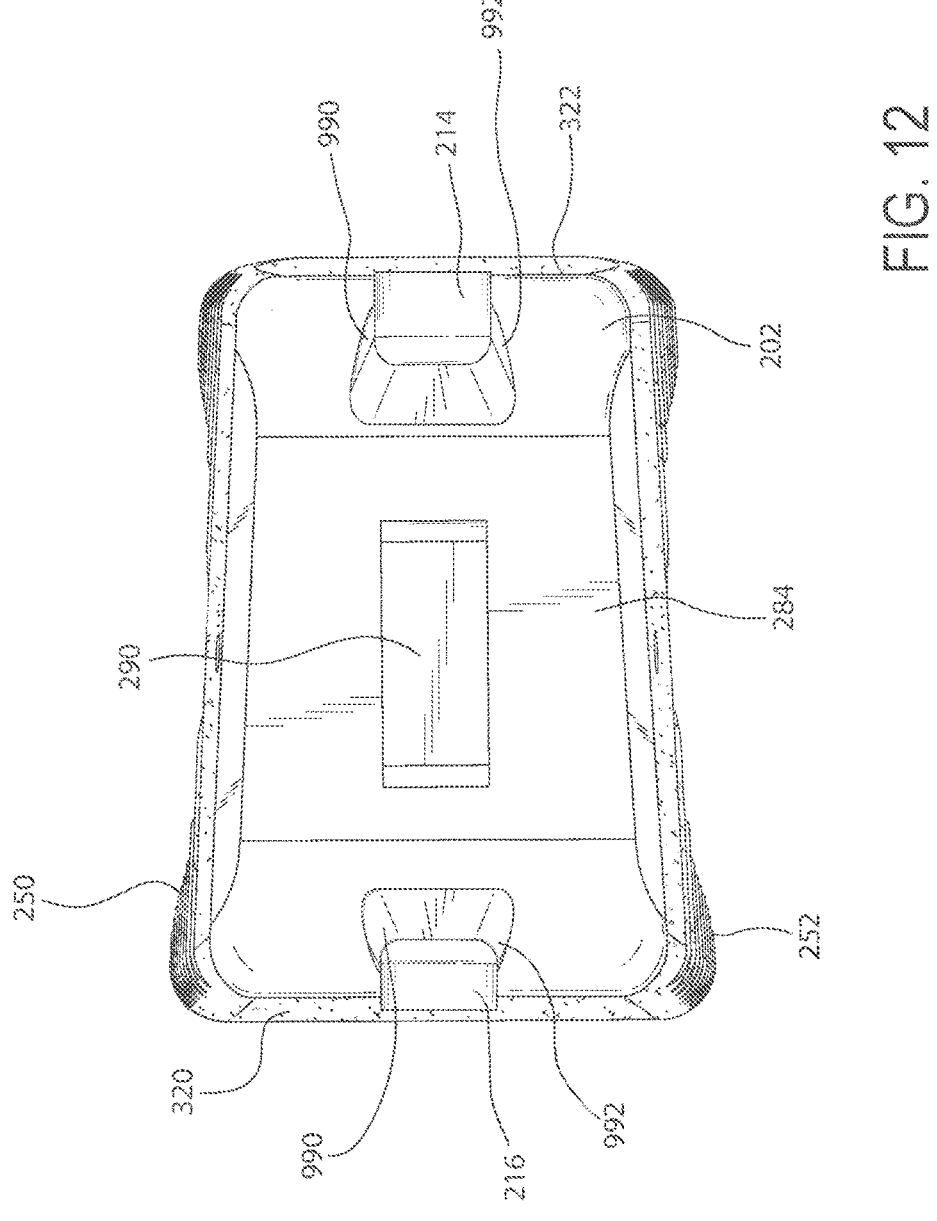
FIG. 12 is a rear elevational view of the implant of FIG. 9 showing recesses on opposite sides of an attachment member of the implant for receiving arms of an inserter tool.

With reference to FIG. 12, the body 202 includes outer lateral surfaces 320, 322 extending from the upper bone engaging portion 250 to the lower bone engaging portion 252. In one form, the lateral surface 320 is taller than the lateral surface 322 such that one lateral side of the implant 200 is taller than the other side. This allows the implant body 202 to match the patient anatomy.

In some forms, the body 15 of the implant 10 is fabricated using additive manufacturing and materials other than PEEK. For example, the body 15 may be made of various types of polymers and metallic materials. Further examples include ceramic, hydroxylapatite, titanium, and PEEK.

Figure 13:
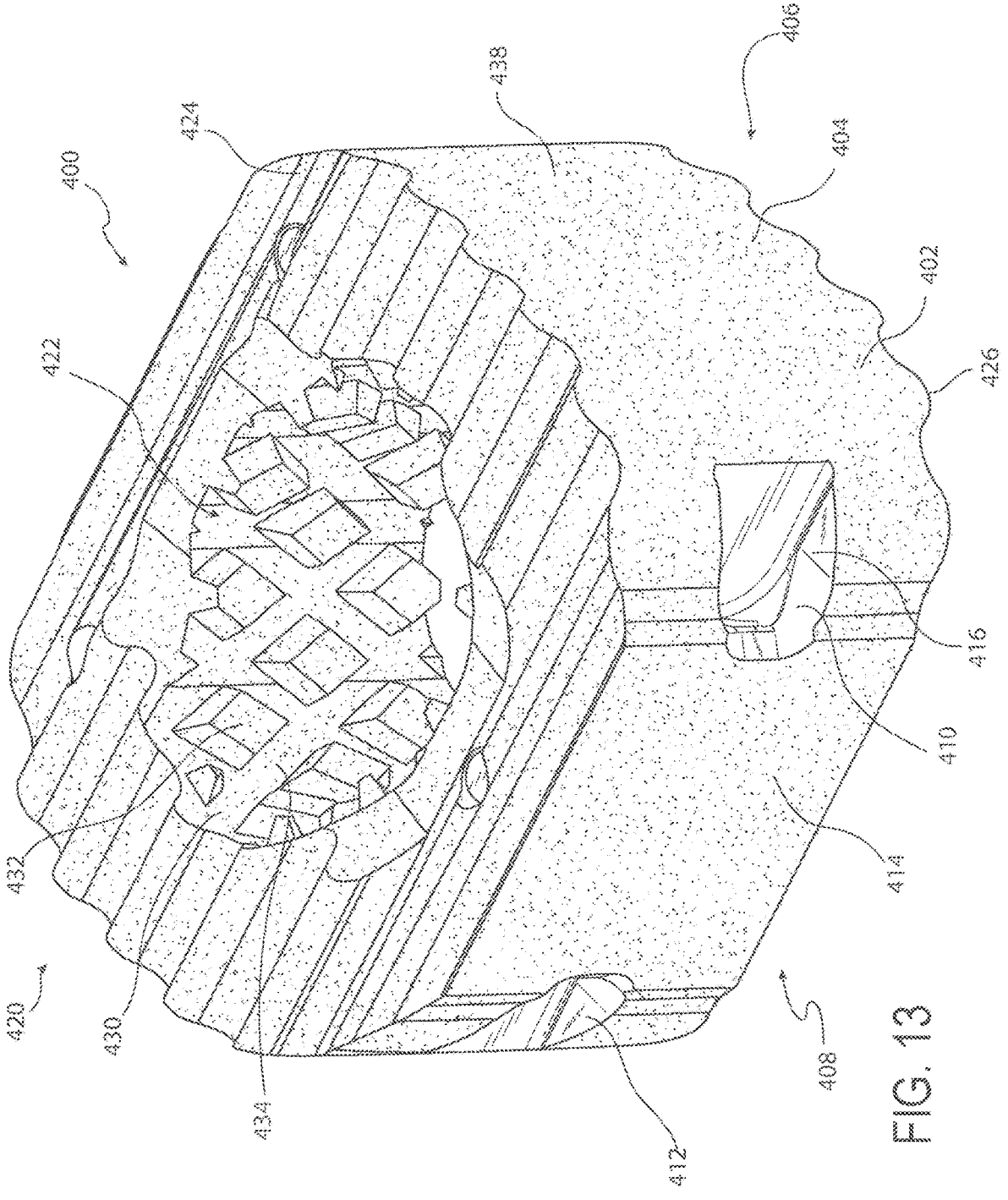
FIG. 13 is a perspective view of an implant showing rough, irregular surfaces of the implant formed by fabricating the implant by selective laser sintering PEEK and smoother, machined surfaces of the implant.
Figure 14:
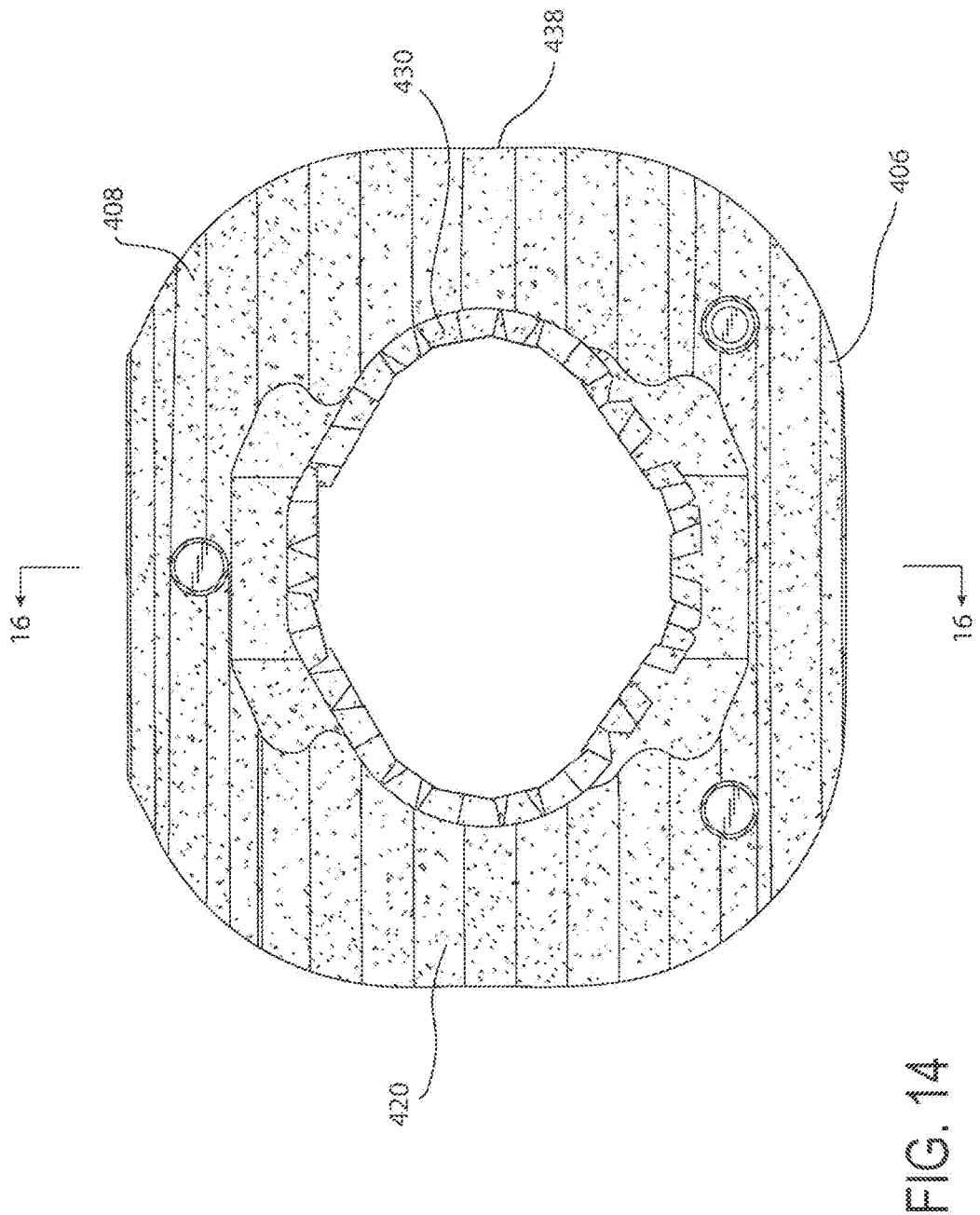
FIG. 14 is a top plan view of the implant of FIG. 13 showing a through opening of the implant and an annular wall extending around the through opening.

With reference to FIG. 13, an implant 400 is provided for being positioned between vertebrae, such as cervical vertebrae, and is similar in many respects to the implants 10, 200 discussed above. The implant 400 has a body 402 that may be fabricated by selective laser sintering PEEK, which results in rough outer surfaces 404 of the body 402. The body 402 includes a leading end portion 406 and a trailing end portion 408. The trailing end portion 408 includes recesses 410, 412 and an attachment member such as a dovetail projection 414 intermediate the recesses 410, 412. The recesses 410, 412 and the dovetail projection 414 are machined into the body 402. This causes the trailing end portion 408 to have smooth machined surfaces 416.

The body 402 includes an annular wall 420 surrounding a compartment, such as a through opening 422, for receiving bone growth material. The annular wall 420 includes an upper bone engaging portion 424 and a lower bone engaging portion 426. The annular wall 420 extends from the upper to the lower bone engaging portion 424, 426 and around the through opening 422 without interruption. By extending without interruption, it is intended to mean that there are no through apertures in communication with the through opening 422 that extend from the inner surface 430 to the outer surface 438. This increases the strength of the annular wall 420 by limiting stress concentrating features.

Figure 15:
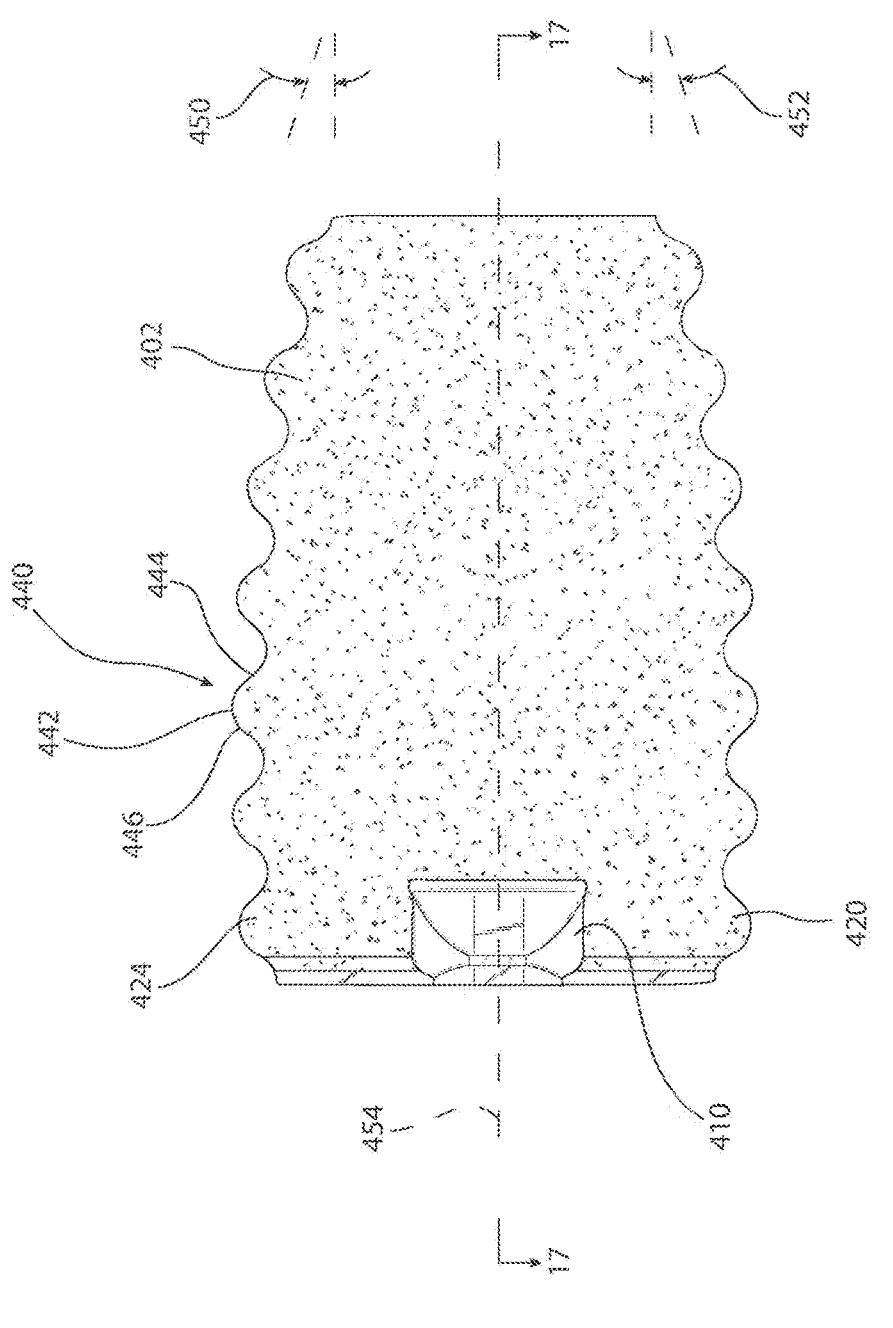
FIG. 15 is a side elevational view of the implant of FIG. 14 showing a wedge-like profile of the implant.

With reference to FIG. 15, the upper and lower bone engaging portions 424, 426 include a plurality of gripping members 440 each having a rounded peak 442 and rounded leading and trailing surfaces 444, 446. The gripping members 440 thereby have an undulating shape along the upper and lower bone engagement portions 424, 426. The upper and lower bone engaging portions 424, 426 are tapered to have angles 450, 452 relative to a longitudinal axis 454 of the body 202. This tapered profile of the implant 200 aids in insertion of the implant 200 between vertebrae.

Figure 16:
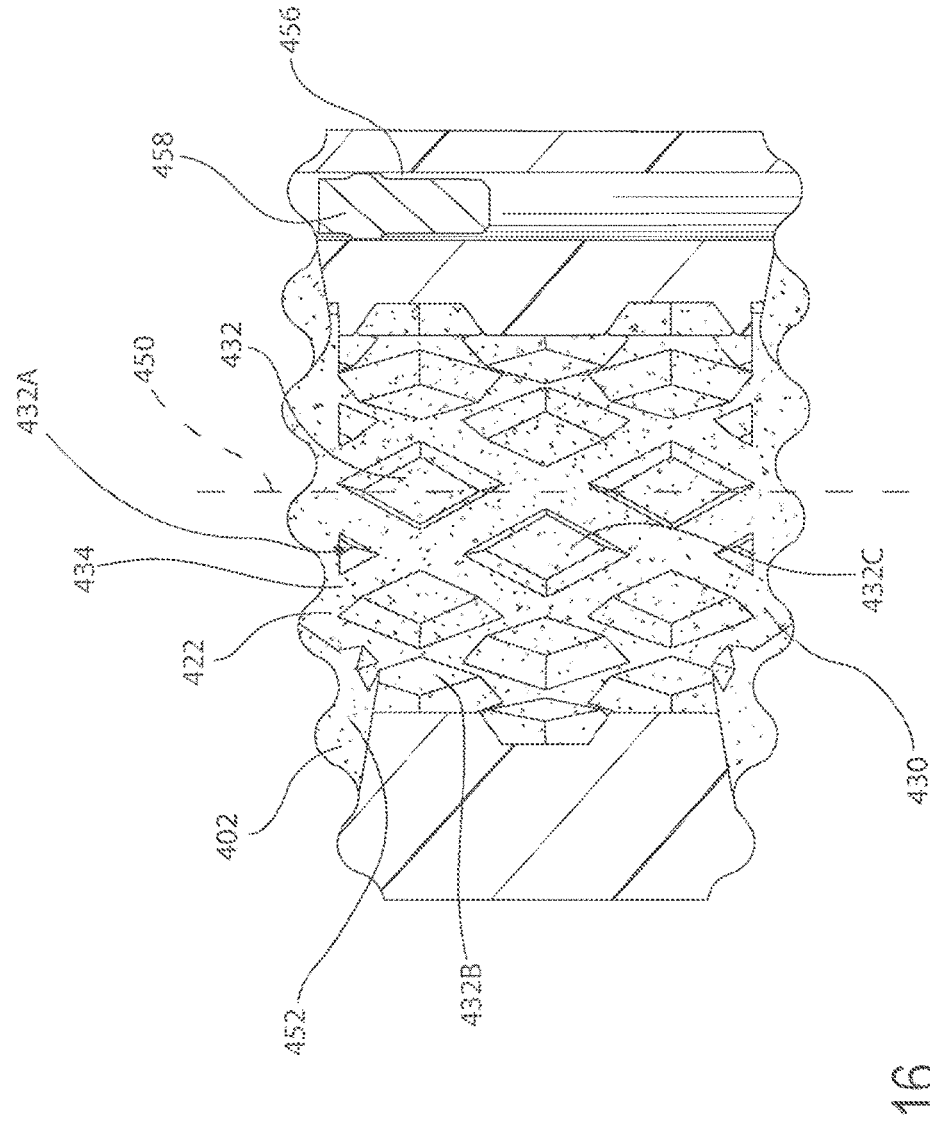
FIG. 16 is a cross-sectional view taken across line 16-16 in FIG. 14 showing a pattern of nubs and pathways of an inner surface of the annular wall.

With reference to FIG. 16, the inner surface 430 of the annular wall 420 extends around a central, vertical axis 450 of the body 402. The annular wall 420 includes nubs 432 and crisscrossing or intersecting pathways 434. The nubs 432 and pathways 434 are similar to the nubs 16, 232 and pathways 54, 268 discussed above. The nubs 432 have varying sizes along the inner surface 430. For example, the nubs 432 include nubs 432A that are truncated or reduced in size near an upper surface 452 of the annular wall 420. The nubs 432 include nubs 432B that are larger than nubs 432A but are partially truncated or reduced in size relative to nubs 432C. The nubs 432C are more toward the middle of the annular wall 420 and not truncated and have a full diamond shape. The body 402 may also include one or more bores 456 that receive marker pins 458.

Figure 17:
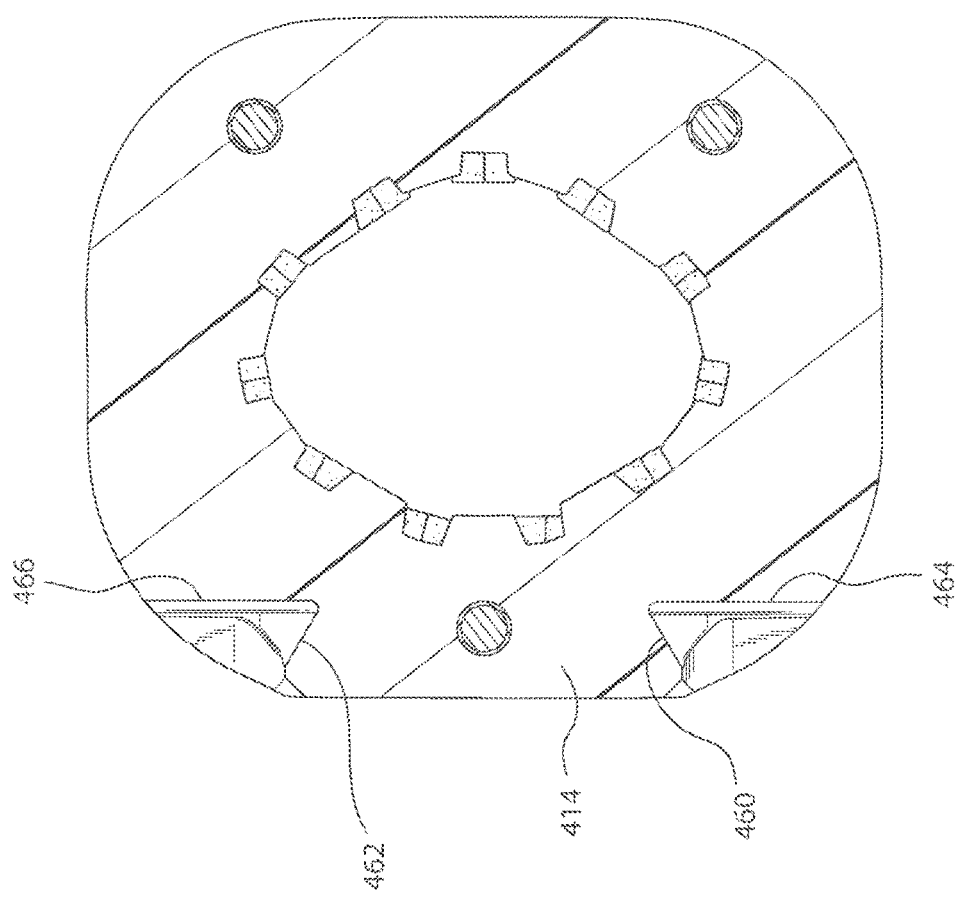
FIG. 17 is a cross-sectional view taken across line 17-17 in FIG. 15 showing an attachment member of the implant for being clamped by arms of an inserter tool.
Figure 18:
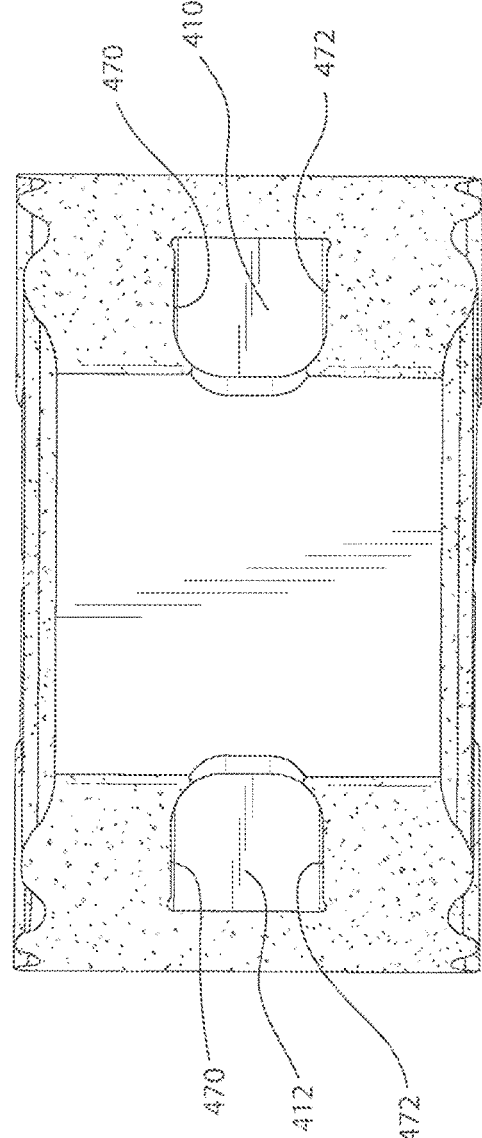
FIG. 18 is a rear elevational view of the implant of FIG. 13 showing recesses on opposite sides of the attachment member for receiving the inserter tool arms.

With reference FIG. 17, the dovetail projection 414 includes inclined walls 460, 462 and walls 464, 466 that extend transversely to the inclined walls 460, 462. The dovetail projection 414 provides a thick structure to receive the compressive forces from the arms of an inserter tool. Further, the walls 464, 464 may abut surfaces of the inserter tool to absorb impacts from the inserter tool such as impacts due to a surgeon striking the inserter tool with a mallet to urge the implant 400 into an intervertebral space. As shown in FIG. 18, the body 402 includes ceilings 470 and floors 472 that form upper and lower boundaries of the recesses 410, 412.

Figure 19:
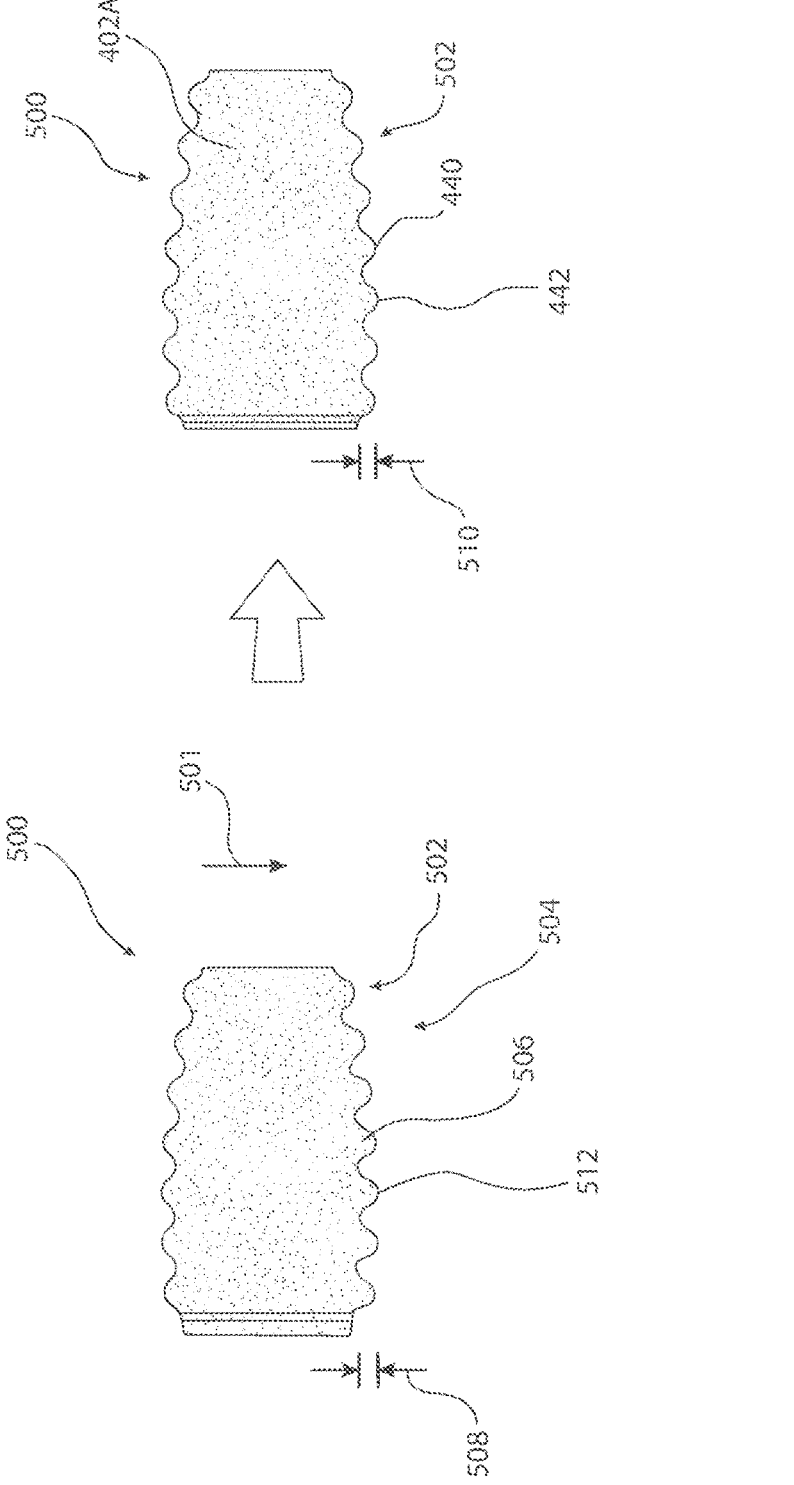
FIG. 19 shows an engineering model of an implant body and the implant body that results from selective laser sintering PEEK based on the model.

With reference to FIG. 19, the process of fabricating the body 402 of the implant 400 involves providing a model 504 to a computer that controls operation of a selective laser sintering machine. The computer uses the model 504 to direct a laser of the machine to fuse particles of a bed of PEEK into layers and forms a printed body 402A by progressively printing one layer after another. The machine starts building the layers of the body 402 by first fusing particles of PEEK to form a skin down surface 500. The machine progressively forms layers one below another in direction 501 until the machine reaches a skin up surface 502 of the printed body 402A. Due to the sintering method used to melt the particles in the PEEK bed, the process may have a lower resolution at the skin down surface 500 then the skin up surface 502. More specifically, the laser hits the particles of the PEEK bed with the most energy when the laser begins to form a first layer, i.e., the skin down surface 500 of the printed body 402A. More particles are added to bed above the first layer, and the laser is directed to form a second layer above the first layer. This process is repeated until the final layer including the skin up surface 502 has been formed. The laser has less energy when it is forming the second and higher layers such that those layers have more accuracy than the first layer.

To compensate for this, the model 504 provided to computer associated with the selective laser sintering machine may have exaggerated geometry so that printed body 402A that results from the selective laser sintering has the desired geometry. For example, the model 504 may have lower gripping members 506 that have a peak-to-valley height 508 that is greater than a peak-to-valley height 510 of the gripping members 440 of the body 402A that result from the selective laser sintering process. In other words, the gripping members 506 of the model 504 provided to the selective laser sintering machine are more exaggerated than the gripping members 440 that result from the 3D printing process. The difference in a height 508, 510 is due to the lower resolution at the skin down surface 502 causing the gripping members 440 to be smaller than the gripping members 506. Other features of an implant may be emphasized or reduced in the model 504 provided to the selective laser sintering machine. For example, the curvature of peaks 512 of the gripping members 506 may be different than the curvatures of the peaks 442 of the printed body 402A.

Figures 20, 21, 22:
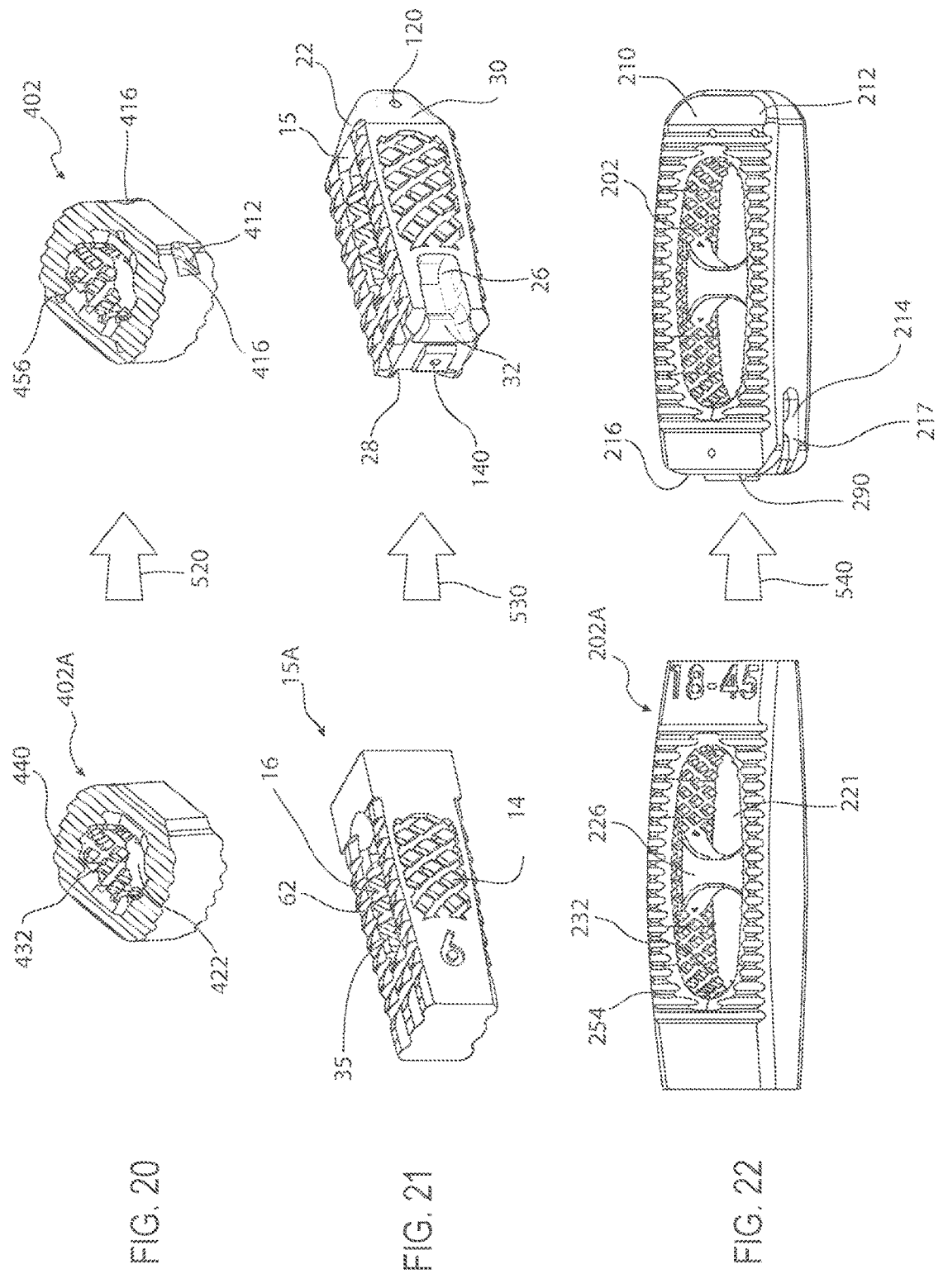
FIGS. 20, 21, and 22 are perspective views of bodies of implants fabricated by selective laser sintering PEEK and the bodies after the bodies have been machined.

With reference to FIG. 20, the selective laser sintering machine produces the printed body 402A. The printed body 402A includes the gripping members 440, the nubs 432, and the through opening 422. The printed body 402A is then machined 520 to impart structural details to the printed body 402A that require higher precision than provided by the selective laser sintering process. For example, the recesses 412, 416 and marker pin bores 456 are machined into the printed body 402A to produce the body 402. The process of machining the recesses 412, 416 into the 3D body 402 produces the smooth machined surfaces 416 of the body 402.

With reference to FIG. 21, fabricating the body 15 includes producing a printed body ISA by selective laser sintering PEEK. The printed body ISA includes the gripping members 62, nubs 14, 16, and through opening 35. The printed body ISA is machined 530 to form the nose 22, recesses 26, 28, boss 140, trailing end surface 144, and marker pin apertures 120, 122 into the printed body ISA This produces the body 15 discussed above. The machining 530 imparts the smooth machined surfaces 30, 32 of the body 15.

With reference to FIG. 22, fabricating the body 202 includes producing a printed body 202A by selective laser sintering PEEK. The printed body 202A includes the through opening 221, the web 226, the gripping members 254, and the nubs 232. The printed body 202 is then machined 540 to form the nose 210, recesses 214, 216, trailing end surface 284, and boss 290 into the body 202A The machining 540 imparts the smooth machined surfaces 212, 217.

With reference to FIGS. 23, 24, and 25, the implant bodies are shown in their respective orientations during fabricating of the implant bodies by selective laser sintering the particles of the PEEK bed. As shown in FIG. 23, the printed body 402A is positioned so that the skin up surface 500 and the skin down surface 502 contain the gripping members 440.

With reference to FIG. 24, the orientation of the implant body during the selective laser sintering process may be selected to position lower accuracy portions of the implant body at regions of the implant body that are machined off For example, the printed body ISA may be positioned to have the skin up surface 550 be at the trailing end portion 20 of the printed body ISA and a skin down surface 554 be at the leading end portion 18 of the body ISA As discussed above, the printed body ISA is machined 530 to form the nose 22, recesses 26, 28, boss 140, and trailing end surface 144. Because the printed body ISA is being machined to form these features at the leading and trailing end portions 18, 20, inaccuracies at the skin up and skin down surfaces 550, 554 are removed by the machining process.

With reference to FIG. 25, the printed body 202A may be positioned so that the trailing end portion 206 of the printed body 202A is at a skin up surface 562 and the leading end portion 208 is at a skin down surface 568. In this manner, any imperfections that occur at the skin up and skin down surfaces 562, 568 are machined off when the recesses 214, 216, boss 290, and nose 210 are machined into the printed body 202A. Additionally, orienting the body 202A so that it prints along a diagonal path, rather than vertical or horizontal, reduces unintended curvature of the body 202A that may result from the selective laser sintering process.

Figure 26:
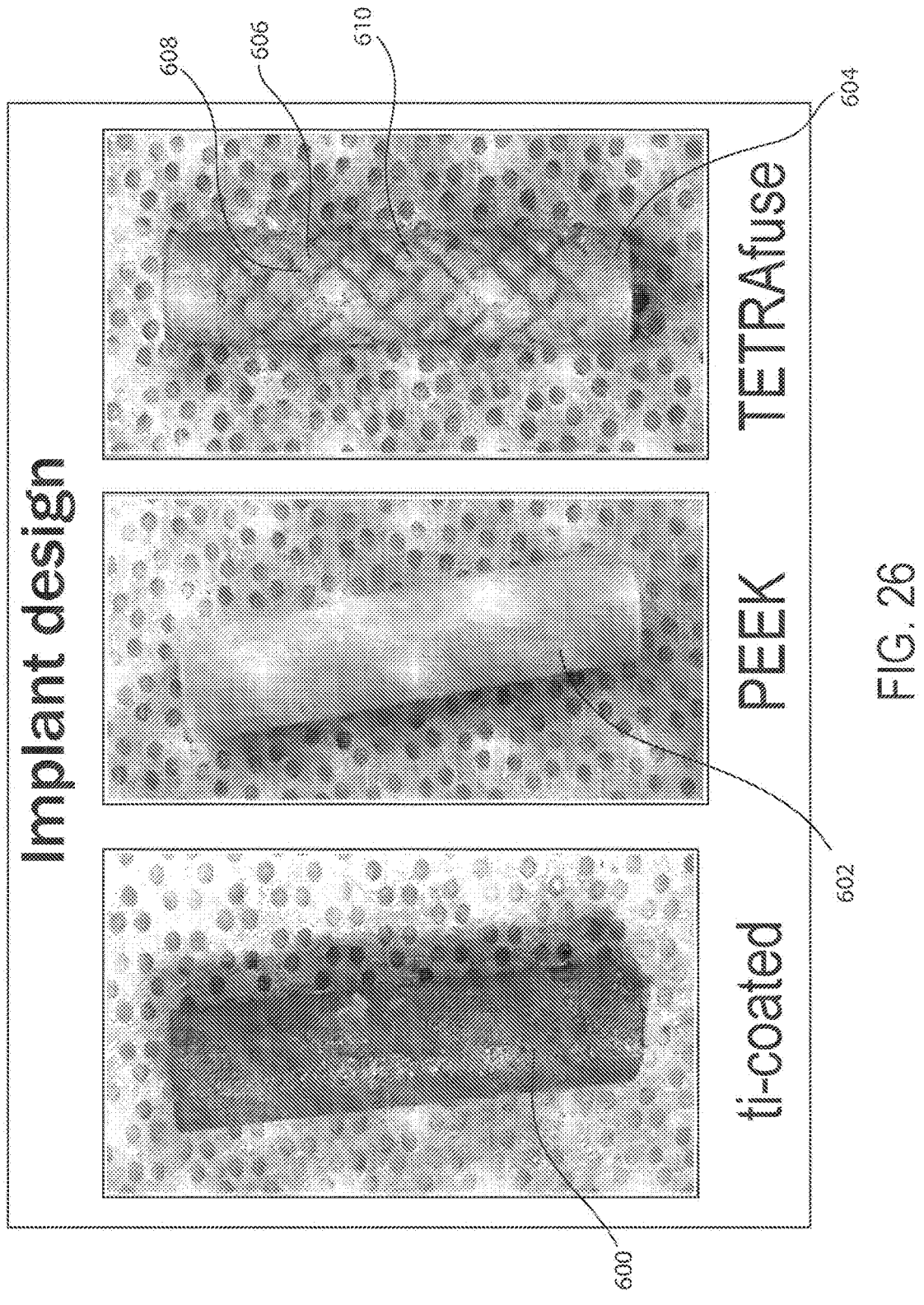
FIG. 26 is an image of different types of pins implanted during a surgical trial including a pin that was formed by selective laser sintering PEEK and includes nubs.

With reference to FIG. 26, testing was performed to provide an understanding of the bone fusion properties provided by the implants 10, 200, 400 discussed above. The testing included an in vivo ovine bone defect study. The study was designed to evaluate biomechanical push-out strength, bone apposition, and bone area of implants including titanium coated PEEK implants 600, uncoated PEEK implants 602, and implants 604 manufactured by selective laser sintering PEEK material. The implants 600 had a roughened outer surface of the titanium material. The implants 604 included diamond-shaped nubs 606 and pathways 608 separating the nubs 606. Because the implants 604 were produced by selective laser sintering PEEK, the implants 604 had a rough exterior surface 610 similar to the rough exterior surfaces of the implants 10, 200, and 400 discussed above.

The implants 600, 602, 604 were cylinder shaped with an outer diameter of 6 mm and a total length of 30 mm. The implants 600, 602, 604 were randomly placed into distal femurs of sheep and allowed to heal for an eight-week time period or a sixteen-week time period. Six implants of each type of implant 600, 602, 604 were implanted for each time period, with three samples per implant type per time period analyzed for push-out testing and three for histological analysis. Histological analysis included fibrosis and immune response assessment using scanning electron microscopy and light microscopy methods. Biomechanical push-out testing was also performed to assess a peak push-out force.

The imaging and histological analyses demonstrated new viable bone surrounding the implants 600, 602, 604. Osteoblast activity suggested the bone to be viable and actively remodeling in the periprosthetic bone region with all three implant types. Bone area in periprosthetic region increased from 26.7 to 40.1% with implant 604, from 14.9 to 35.4% with implant 600, and 40.1 to 47.6% with implant 602. Bone organization and maturation progressed between 8 and 16 week time points.

Periprosthetic regions had similar distribution of trabecular bone and marrow space in all groups but the groups using implant 602 showed higher degree of fibrotic membrane formation around the implants. Bone apposition increased from 3.6% to 34.1% of implant area with implants 604, from 10.5 to 52.3% with implants 600, and decreased from 40% to 16% with implants 602 by 16 weeks. Excellent osseointegration was achieved when implants 604 and 600 were implanted in close approximation to the bone. The implants 602 showed more "spot welding" osseointegration with limited mechanical interlock. No adverse reaction was observed to any implant type.

The histological analysis showed that the topography of the implants 604, which included the nubs 606 and rough exterior surface 610 resulting from selective laser sintering PEEK to fabricate the implants 604, provided larger area for progressive bone growth beyond the eight week time point differently from the implants 600, 602. Bony ingrowth on the implants 604 followed surface topography and filled the micro pores of the implants 604 demonstrating excellent osteoconductive characteristics of the implants 604.

Figure 30:
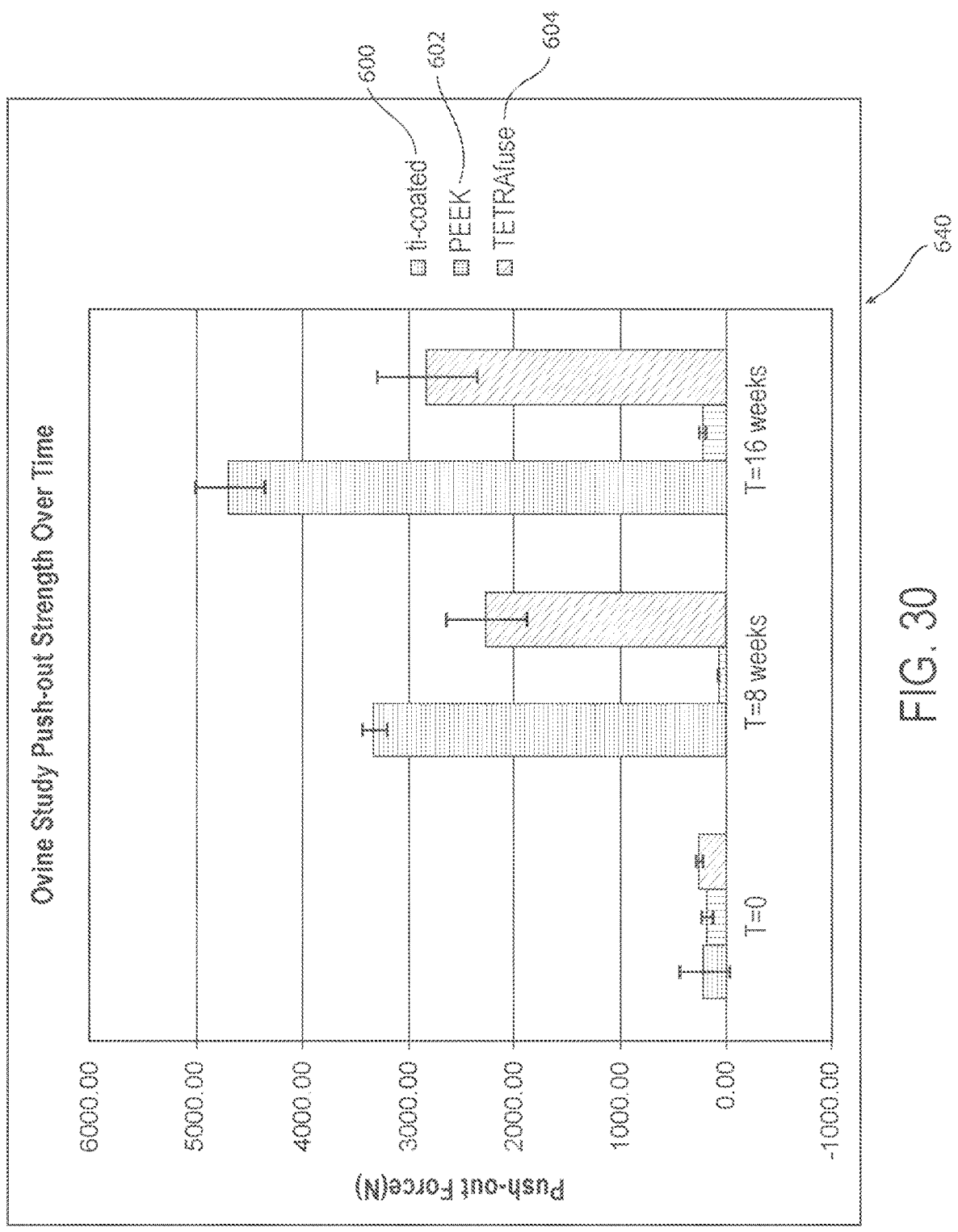
FIG. 30 is a graph showing the push-out resistance of different materials.

Push-out strength significantly increased with the implants 604 and 600 by eight weeks, which is indicative of early and rapid osseointegration. The overall peak force in the group of implants 604 (2819.9 N) was over ten fold higher than the group of implants 602 (230.0N) and about 40% lower than group of implants 600 (4682.9N) by the sixteen-week end point. The results of the pushout testing are provided in a graph 640 of FIG. 30.

Figure 27:
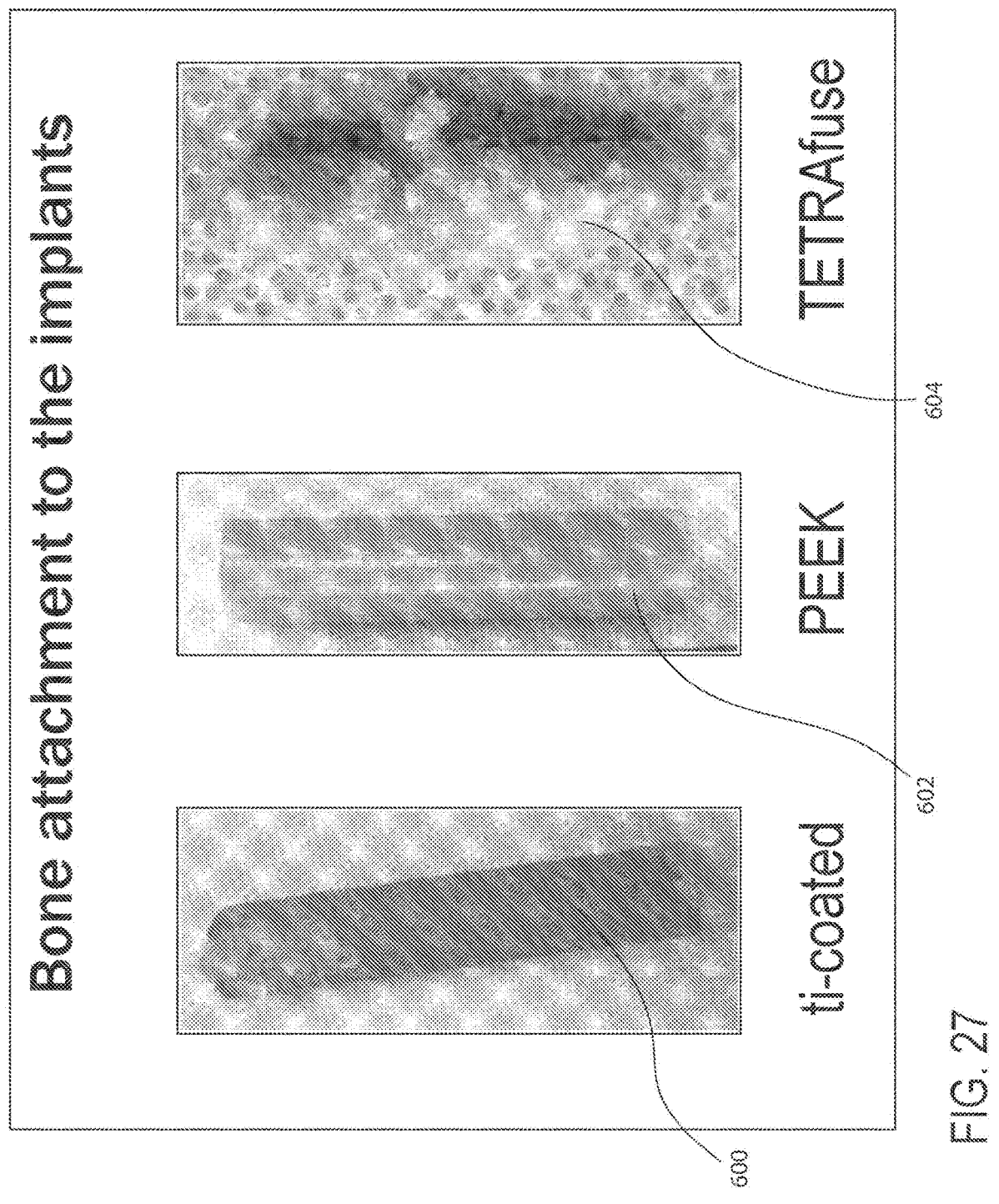
FIG. 27 is an image of the pin implants of FIG. 26 after being removed from the test subjects.

FIG. 27 contains pictures of implants 600, 602, 604 removed during push-out testing at the sixteen week end point. The abundance of cancellous bone attached to the pushed-out implants 604 supported histological observations of significant osseointegration of implants 604 and suggested that the bond between implant and host bone was stronger than the breaking point of native cancellous bone.

On the other hand, the implants 600 had minimal amount of attached bone. The implants 602 had no bone attached.

With reference to FIGS. 28A, 28B, 28C, 29A, 29B and 29C, the study included performing light microscopy after the sixteen week end point for the implants 600, 602, 604. The images of FIGS. 28A, 28B, 28C, 29A, 29B and 29C are cross-sectional views of implants 600, 602, 604 showing bone apposition and ingrowth. The images of FIGS. 29A, 29B and 29C show marrow spaces 613 and bone 614 around the implants 600, 602, 604. The implant 600 had apposition of bone with minimal fibro-connective tissue ingrowth. The implant 602 had large areas of fibro-connective membrane 611 between the bone and the implant 602 and only regional areas 612 of the bone 614 stitching to the implant 602. The implant 604 had bone ingrowth into the surface structure of the implant 604 that filled the topography of the implant 604 with good bone apposition. The bone ingrowth into the topography of the implant 604 included bone 614 surrounding and engaging with the nubs 606 as well as the bone 614 filling in and engaging pores 618 of the rough exterior surface 610 of the implant 604.

In sum, the implants 604 demonstrated superior osteoconductive properties over the implants 602 with excellent osseointegration into cancellous bone of distal femur similar to implants 600. There was no or minimal fibrosis next to implants 604 and 600 when compared to implants 604. The typography of the implants 604, including the nubs 602 and the rough exterior surface 610, endorsed superior bone ingrowth and integration into cancellous bone which occurred by new bone ingrowth instead of apposition as with the implants 600, 602. The peak push out force significantly increased overtime with implants 604, 600 but not with implants 602. The implants 604 did not show interference with routine imaging methods (such as x-rays) used in clinic, unlike the implant 600 which would be radiopaque due to the titanium coating.

It has also been discovered that an implant fabricated by selective laser sintering PEEK has better antibacterial properties in comparison to a conventional PEEK implant. In particular, bacteria and biofilm formation were studied for these two types of implants. Bacteria cell lines used in this study were S. epidermidis and P. aeruginosa. Fluorescence confocal microscopy was used to visualize the colonization of bacteria on the samples of interest. The results of this study revealed that both of these two bacteria adhered and grew less on the nano-featured PEEK material substrates as compared to the PEEK material. In particular, the Gram-negative bacteria (P. aeruginosa) attached and grew less on the PEEK implant when compared to the Gram-positive bacteria (S. epidermidis) on the PEEK implant. More specifically, the PEEK implant had more than a 55% anti-bacterial effect for P. aeruginosa and a 40% anti-bacterial effect for S. epidermidis as compared to the PEEK implant. It is believed that the nano-rough surface of the PEEK implant changes surface energy which in turn can enhance select protein absorption important for inhibiting bacteria attachment and growth.

Figure 31:
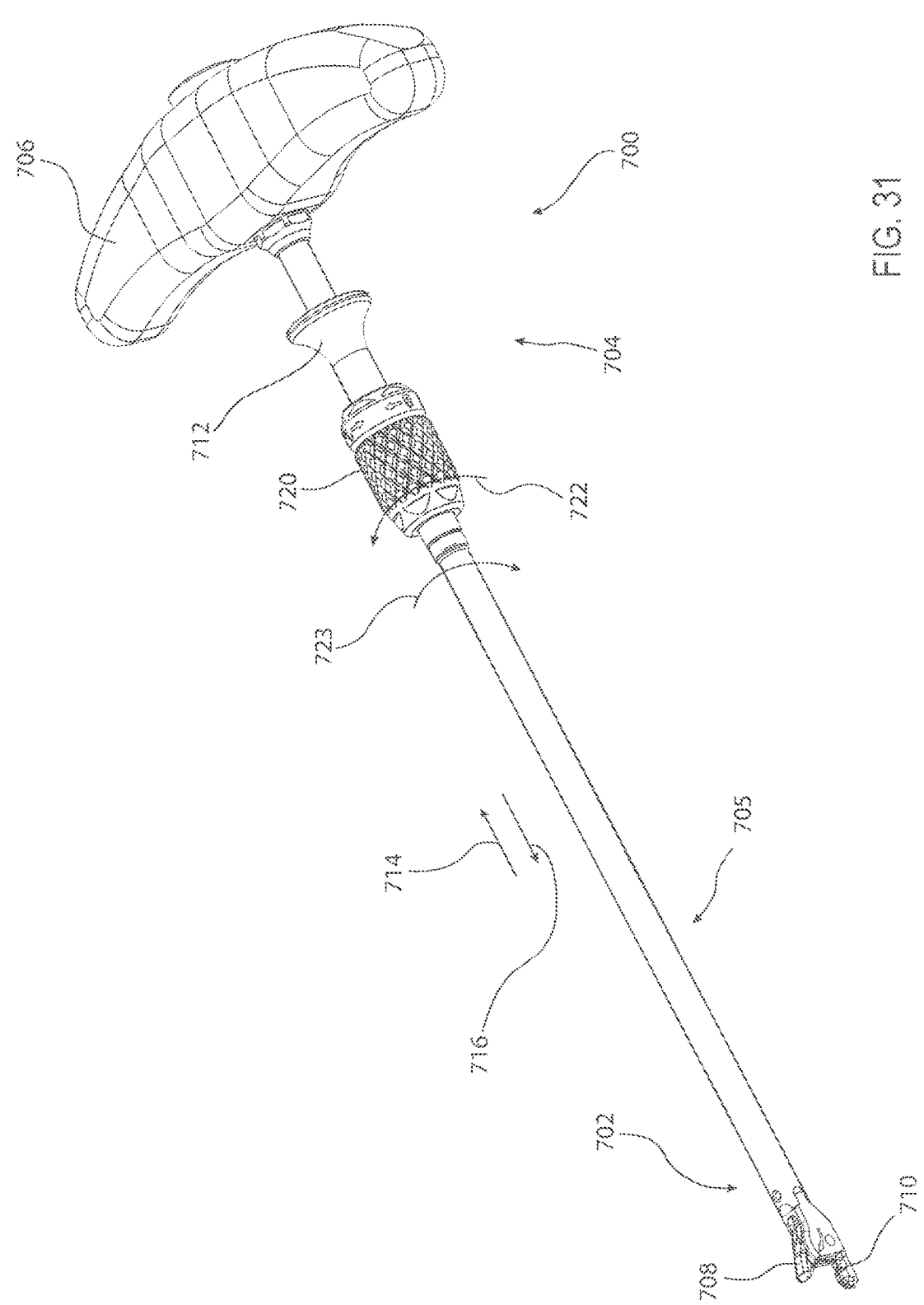
FIG. 31 is a perspective view of an inserter tool for inserting the implant of FIG. 1.

With reference to FIG. 31, an inserter tool 700 is provided for advancing the implant 10 through a surgical passageway and into position between vertebrae. The inserter tool 700 includes a distal end portion 702 for selectively engaging the implant 10 and a proximal end portion 704 having a handle 706. The inserter tool 700 includes a shaft assembly 705 that supports a pivotal clamping arm 708 and a fixed arm 710. The inserter 710 includes an actuator, such as an adjustment knob 712, which may be shifted in direction 714 toward the handle 706 to an open position to pivot the clamping arm 708 to a release position. This allows a user to position the attachment member 24 of the implant 10 between the arms 708, 710. The user then shifts the adjustment knob 712 in direction 716 away from the handle 706 to a closed position to pivot the clamping arm 708 to a clamping position and clamp the attachment member 24 between the arms 708, 710. The inserter tool 700 includes a lock knob 720 having a body 739 that a user may turn in direction 722 to lock the adjustment knob 712 in the closed position. This provides a positive mechanical lock to resist movement of the arm 708 away from the arm 710 and maintain the connection between the distal end portion 702 and the implant 10.

Figure 32:
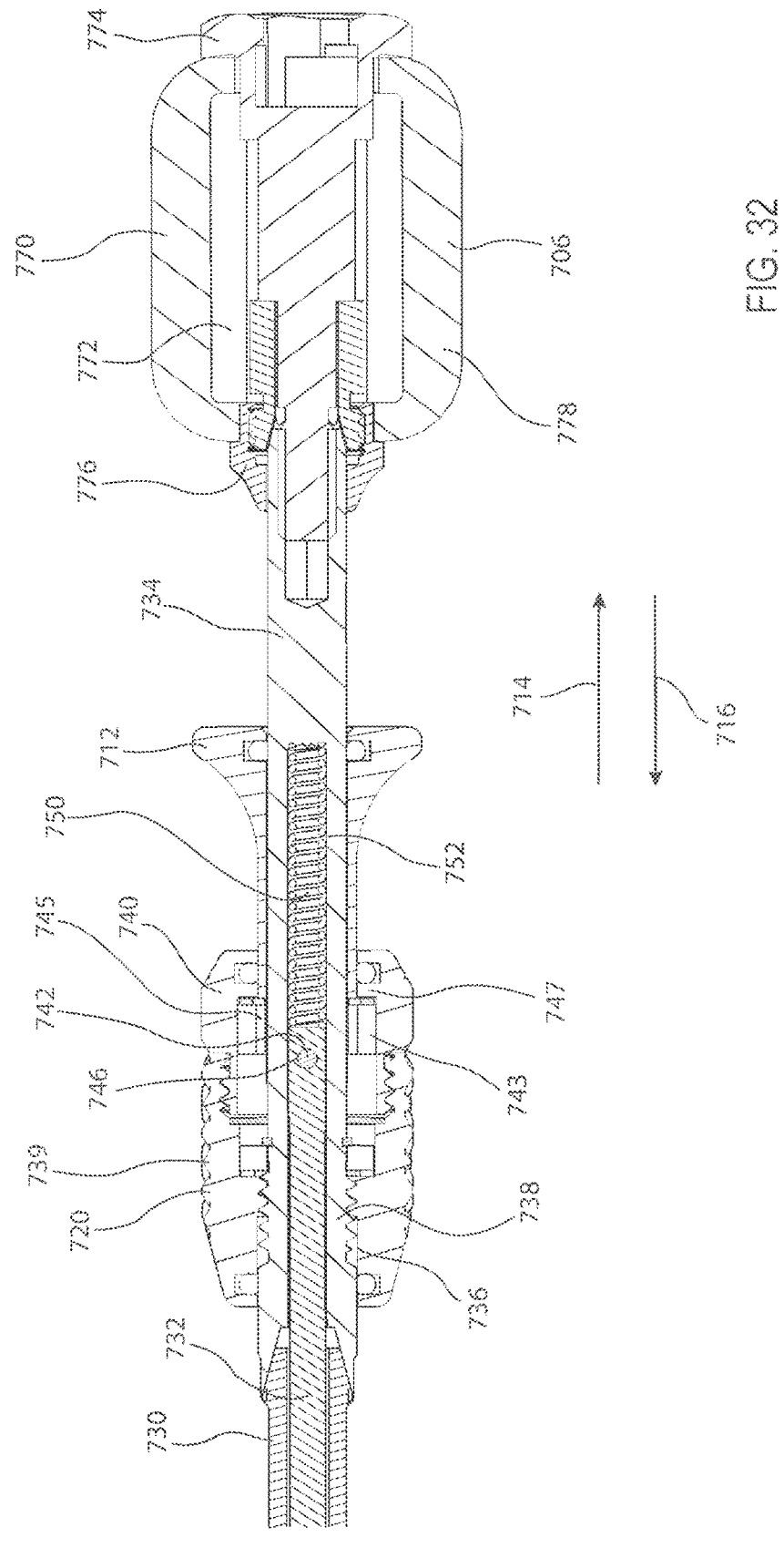
FIG. 32 is a cross-sectional view of a proximal portion the inserter tool of FIG. 31 showing a plunger-shaped adjustment knob that controls connecting of the implant to the inserter tool and a rotatable lock knob for securing the adjustment knob in a locked position.

With reference to FIG. 32, the shaft assembly 705 includes an outer sleeve 730 and an inner shaft 732 within the sleeve 730 that is moveable in directions 714, 716 to pivot the clamping arm 708. The inserter tool 700 includes a rear shaft 734 releasably secured to the outer sleeve 730. The lock knob body 739 has internal threads 736 that engage external threads 738 of the rear shaft 734. The lock knob 720 includes a knob cap 740 connected to the body 739.

The adjustment knob 712 includes a pin 742 that extends through an axially elongated opening of the rear shaft 734 and through a non-axially elongated opening 746 of the inner shaft 732. Thus, when the adjustment knob 712 is shifted in direction 714, the pin 742 transfers the movement of the adjustment knob 712 into movement of the inner shaft 732 in direction 714. The elongated opening of the rear shaft 734 permits the pin 742 to travel within a predetermined range of motion within the rear shaft 734.

The lock nob 720 houses a ring 743 extending around a distal end portion 745 of the adjustment knob 712. The pin 742 has ends that are received in non-axially elongated openings of the ring 743. The pin 742 thereby joins the ring 743, adjustment knob 712, and inner shaft 732 so that the ring 743, adjustment knob 712, and inner shaft 732 shift together in directions 714, 716.

Shifting the knob 712 and inner shaft 732 in direction 714 further compresses a spring 750 received in a cavity 752 of the rear shaft 734. The spring 750 may be partially compressed when the adjustment knob 712 and inner shaft 732 are in the closed position such that the surgeon must further compress the spring 750 in order to shift the adjustment knob 712 and inner shaft 732 to the open positions thereof. The surgeon holds the adjustment knob 712 in the open position to keep the arm 708 pivoted to its release position.

Figure 33:
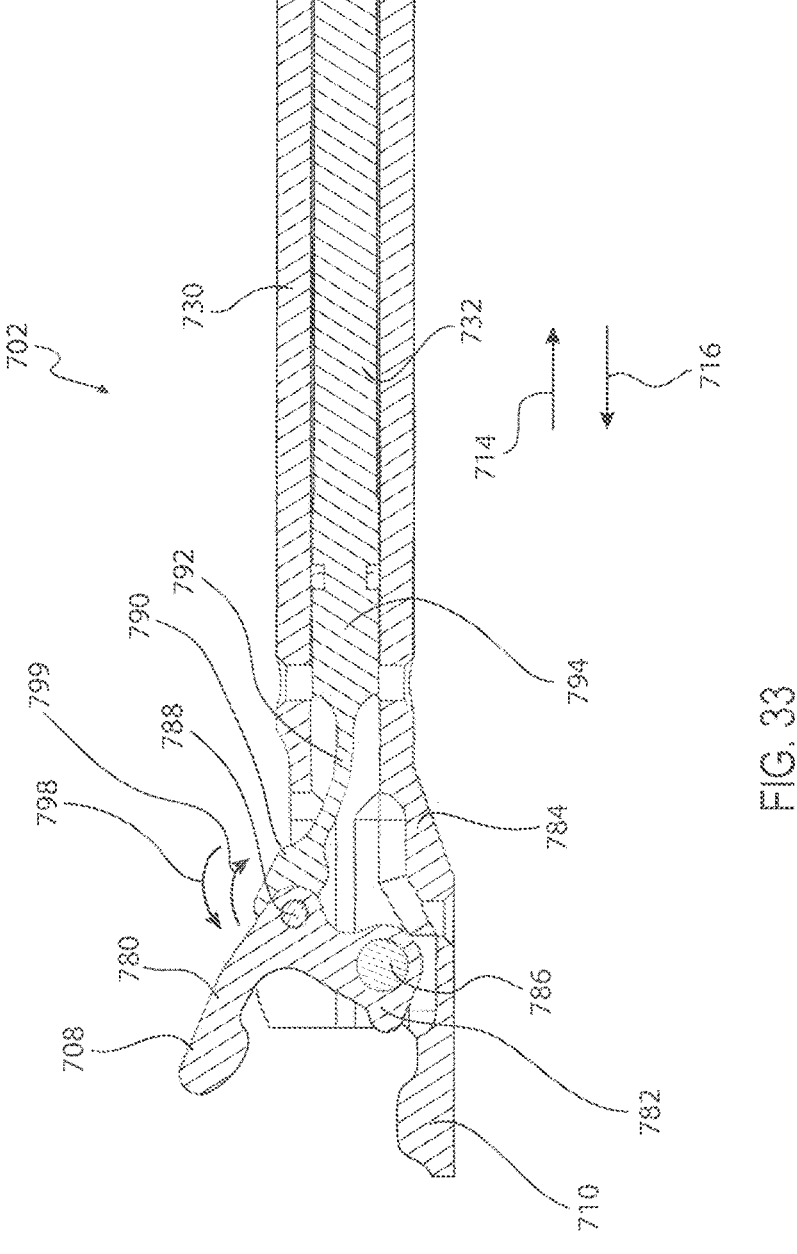
FIG. 33 is a cross-sectional view of a distal portion of the inserter tool of FIG. 31 showing a clamping arm of the inserter tool in an open position.

In one form, the clamping arm 708 is part of an ejecting clamp 780 (see FIG. 33). Once the surgeon positions the implant attachment member 24 between the arms 708, 710, the surgeon releases the adjustment knob 712. The spring 750 urges the inner shaft 732 and adjustment 712 distally in direction 716 which pivots the ejecting clamp 780 in direction 798 and causes the arms 708, 710 to clamp the implant attachment member 24 therebetween.

To lock the ejecting clamp 780 and arm 708 thereof in the clamping position, the surgeon turns the lock knob 720 in direction 722 which causes the lock knob 720 to shift distally in direction 716. The locking knob cap 740 has a flange 747 that abuts the ring 743 and urges the ring 743/pin 742 assembly in direction 716. The surgeon tightens the locking knob 720 in direction 722 so that the engagement between the threads 736, 738 of the lock knob 720 and outer shaft 734 keeps the flange 747 urging the pin 742 in direction 716. In this manner, tightening the lock knob 720 in direction 722 causes the lock knob flange 740 to inhibit the pin 742, inner shaft 732, and adjustment knob 712 from shifting in direction 714 and permitting the arm 708 to pivot to its release position. This locks the arm 708 in the clamping position thereof until the surgeon turns the lock knob 720 in direction 723 to shift the lock knob flange 740 in direction 714, which spaces the flange 747 axially up the rear shaft 734 from the pin 742 and provides space for the pin 742 to shift in direction 714.

With reference to FIG. 32, the handle 706 includes a handle outer portion 770, a handle inner portion 772, and a handle adaptor bolt 774 that connects the handle outer and inner portions 770, 772 to the rear shaft 734. The handle 706 includes a handle lock nut 776 and a spacer 778 for securing the handle inner portion 772 to the rear shaft 734.

With reference to FIG. 33, in one form, the ejecting clamp 780 has a protrusion 782. When the ejecting clamp 780 is pivoted in direction 799, the protrusion 782 contacts the head portion 132 of the implant attachment member 24 and pushes the implant attachment member 24 out from between the arms 708, 710 which assists the surgeon in disconnecting the inserter tool 700 from the implant 10.

The outer sleeve 730 includes a clamp housing 784 and the fixed arm 710 is integrally formed with the clamp housing 784 as shown in FIG. 33. The inserter distal end portion 702 includes a pin 786 that pivotally connects the ejecting clamp 780 to the clamp housing 784. The inserter distal end portion 702 further includes a pin 788 connecting the ejecting clamp 780 to an end portion 790 of the inner shaft 732. The inner shaft 732 includes a flexible portion 792 that may have a reduced cross-sectional thickness as compared to a proximal portion 794 of the inner shaft 732. The flexible portion 792 may bend to compensate for pivoting of the ejecting clamp 780 in direction 799 when the inner shaft 732 is shifted proximally in direction 714. Conversely, the inner shaft 732 shifting in distally direction 716 causes the ejecting clamp 780 to pivot in direction 798. The components of the inserter tool 700 including the shaft 732, sleeve 730, arm 710, clamp 780 may be made of stainless steel such as 17-4 or 465 stainless steel.

Figure 34:
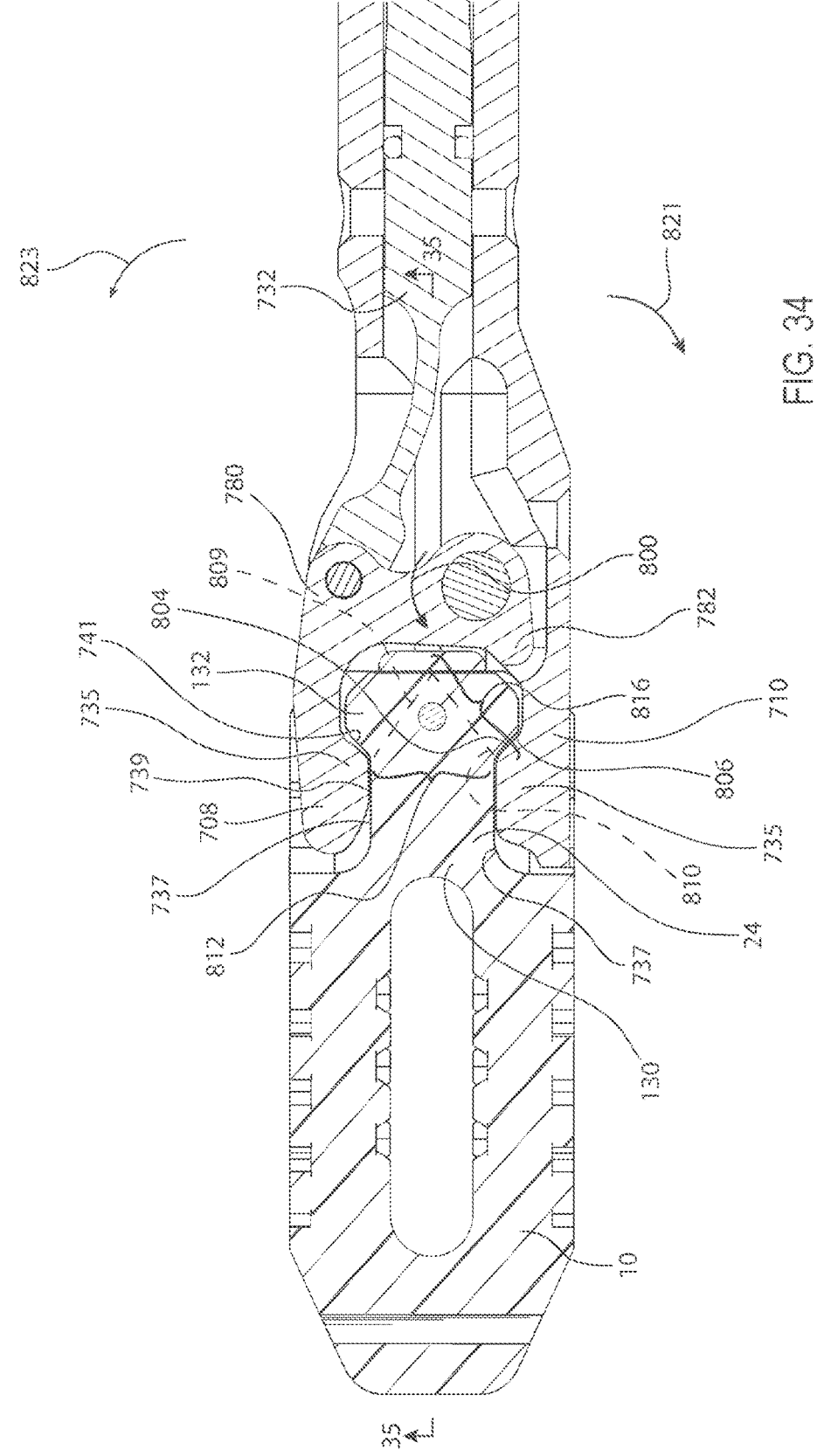
FIG. 34 is a view similar to FIG. 33 showing the clamping arm pivoted to a closed position to clamp an attachment member of the implant between the clamping arm and a fixed arm of the inserter.

With reference to FIG. 34, the arms 708, 710 and implant 10 have mating portions configured to fix the implant 10 to the arms 708, 710 with the arms 710 clamping the attachment member 24 therebetween. The mating portions provide a positive mechanical interlock between the inserter tool 700 and the implant 10 that ensures the implant 10 is correctly and firmly grasped by the inserter tool 700. For example, the arms 708, 710 may have protrusions 735 configured to fit into recesses 737 formed by the neck 130 and head 132 of the attachment member 24. The arms 708, 710 have surfaces 739 that conform to surfaces 741 of the neck 130 and head 132 of the attachment member 24. In this manner, the implant 10 is locked to the inserter distal end portion 702 and generally cannot twist or slide relative to the distal end portion 702.

The attachment member 24 includes tapered surfaces 804 on opposite sides of the head portion 132 of the attachment member 24 and the protrusions 735 of the arms 708, 710 include tapered surfaces 806 that engage the surfaces 804. The surfaces 804, 806 are inclined relative to the longitudinal axis 113 of the implant 10.

In FIG. 34, the inner shaft 732 has been shifted distally in direction 716 to pivot the ejecting clamp 780 to the clamping position thereof. The clamping arm 708 of the ejecting clamp 780 compresses the implant attachment member 24 against the arm 710. This compression urges the surface 804 of the head portion 132 of the attachment member 24 against the surfaces 806 of the arms 708, 710. The surfaces 804, 806 extend transversely to the longitudinal axis 113 of the implant 10. The engagement of the surfaces 804, 806 urges the attachment member 24 in proximal direction 714 and presses the implant trailing end surface 144 against upper and lower portions 820, 822 (see FIG. 35) of the clamp housing 784. In this manner, the material of the attachment member 24 is compressed generally between the protrusions 735 of the arms 708, 710 and the clamp housing upper and lower portions 820, 822.

The engaged surfaces 804, 806 of the implant attachment member 24 and the arms 708, 710 also direct compression of the attachment member 24 due to manipulation of the inserter tool 700 along diagonal paths oblique to the longitudinal axis 26 of the body 15. More specifically, manipulating the inserter tool 700 in lateral direction 821 when the implant 10 has been advanced partially between vertebrae causes compression of the attachment member 24 generally along a transverse path 809. The compression is due at least in part on the arm 710 pushing distally on the attachment member 24 and the arm 708 pulling proximally on the attachment member 24. The transverse path 809 extends from the protrusion 735 of the arm 708 to the trailing end surface 144 of the attachment member.

Similarly, manipulating the inserter tool 700 in lateral direction 823 causes compression of the attachment member 24 to act generally along a transverse path 810 between the protrusion 735 of the arm 710 and the trailing end surface 144. If the clamping arms 708, 710 only applied compression in a lateral path across the attachment member 24 when the inserter tool 700 was manipulated in directions 821, 823, such compression would act through a distance 812 of the attachment member 24. As shown in FIG. 34, the distance 816 along transverse path 810 is greater than the distance 812. This means that a greater thickness of material of the attachment member 24 is subjected to the compressive forces due to the engagement between surfaces 804, 806 when the inserter tool is manipulated in directions 821, 823. By increasing the material of the attachment member 24 subject to the compression forces, the attachment member 24 may be strengthened to resist loading during manipulation of the inserter tool 700.

Figure 35:
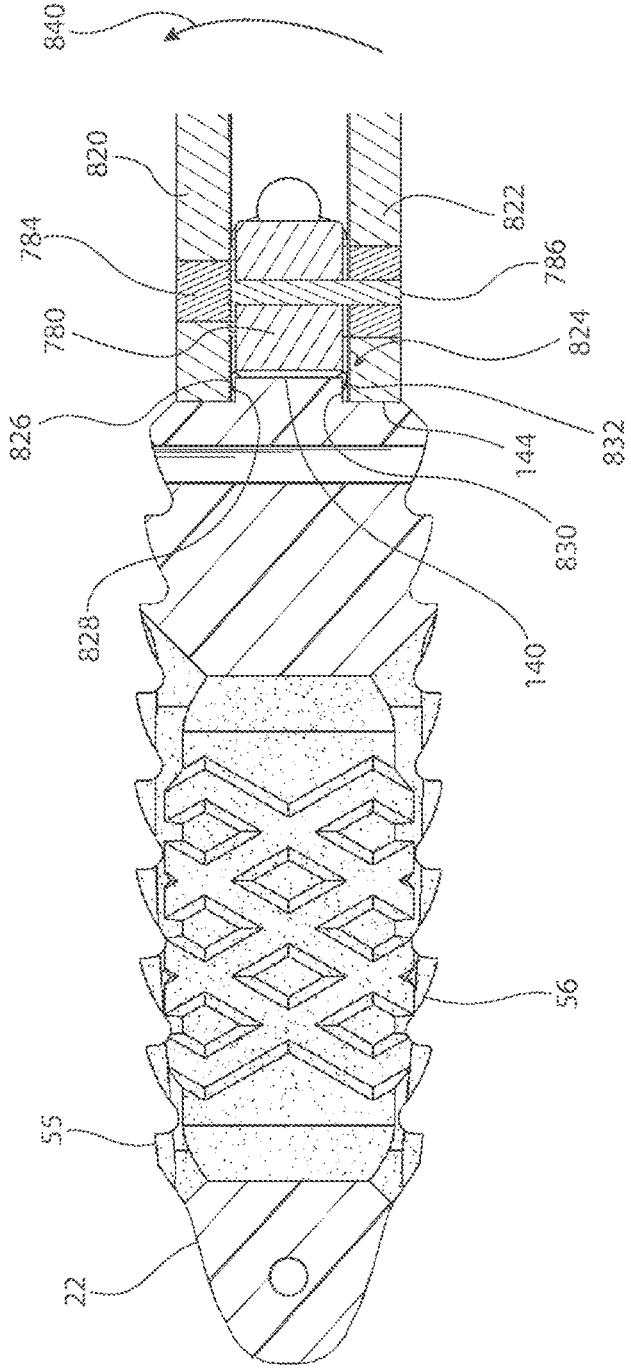
FIG. 35 is a cross-sectional view taken across line 35-35 in FIG. 34 showing the boss of the implant received as a plug in a socket of a distal end of the inserter tool.

With reference to FIG. 35, the upper and lower portions 820, 822 of the clamp housing 784 define a socket 824 for receiving the boss 140 of the implant 10. This creates confronting surfaces 826, 828 and 830, 832 that can transfer loading from the inserter tool 700 to the implant 10. More specifically, if the upper and lower bone engaging portions 55, 56 are positioned partway into a space between vertebrae, and the surgeon lifts up the handle 706 in direction 840, the surfaces 826, 828 and 830, 832 can abut and transfer the loading from the inserter tool shaft 705 to the implant 10. The boss 140 thereby increases the axial length of engagement between the implant 10 and the inserter tool 700 along the longitudinal axis 113 of the implant 10. The loading from the lifting of the shaft 705 in direction 840 is also transferred to the implant 10 by way of the arms 708, 710 pressing against the ceilings 850 and floors 852 (see FIG. 6) of the body 15.

With reference to FIGS. 36, 37, and 38, a method of connecting the implant 10 to the inserter tool 700 is provided. Initially, the lock knob 720 is in an unlocked position and the adjustment knob 712 has been shifted in direction 714 to the proximal, open position as shown in FIG. 36. This causes the clamp arm 708 to pivot to the release position. The implant 10 may be then be advanced in direction 714 to position the attachment member 24 between the arms 708, 710. Next, the adjustment knob 712 is released and the spring 750 urges the inner shaft 732 and adjustment knob 712 distally in direction 716 as shown in FIG. 37. The shifting of the inner shaft 732 in direction 716 causes the arm 708 to pivot in direction 798 and clamp the attachment member 24 between the arms 708, 710. As shown in FIG. 37, the arms 708, 710 are within the envelope of the implant 10 and do not extend laterally outward from the implant 10 which makes the implant 10 easier to advance into the patient.

Next, the lock knob 720 is turned in locking direction 722 as shown in FIG. 38. This shifts the locking knob 720 in direction 716, brings the locking knob flange 720 into contact with the ring 747, and inhibits the pin 742 and inner shaft 732 connected to the ring 747 from shifting in direction 714. This locks the clamping arm 708 in the clamping position and keeps the arms 708, 710 clamping the implant attachment member 24 therebetween.

Figure 39:
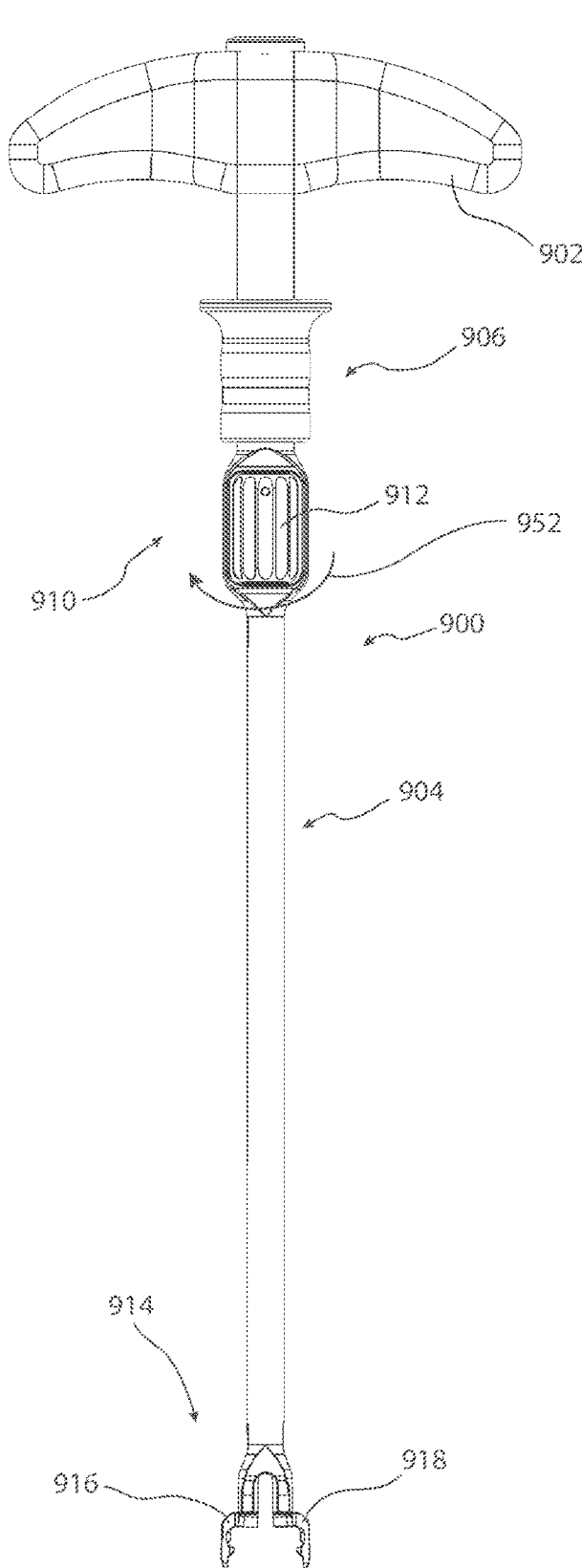
FIG. 39 is an elevational view of an inserter tool for inserting the implant of FIG. 9.

With reference to FIG. 39, an inserter 900 is provided for positioning the implant 200 between vertebrae. The inserter 900 includes a handle assembly 902 and a shaft assembly 904 that is releasably connected to the handle assembly 902 by a quick release mechanism 906 of the handle assembly 902. The shaft assembly 904 includes a proximal end portion 910 having a control knob 912 and a distal end portion 914 having arms 916, 918.

Figure 40:
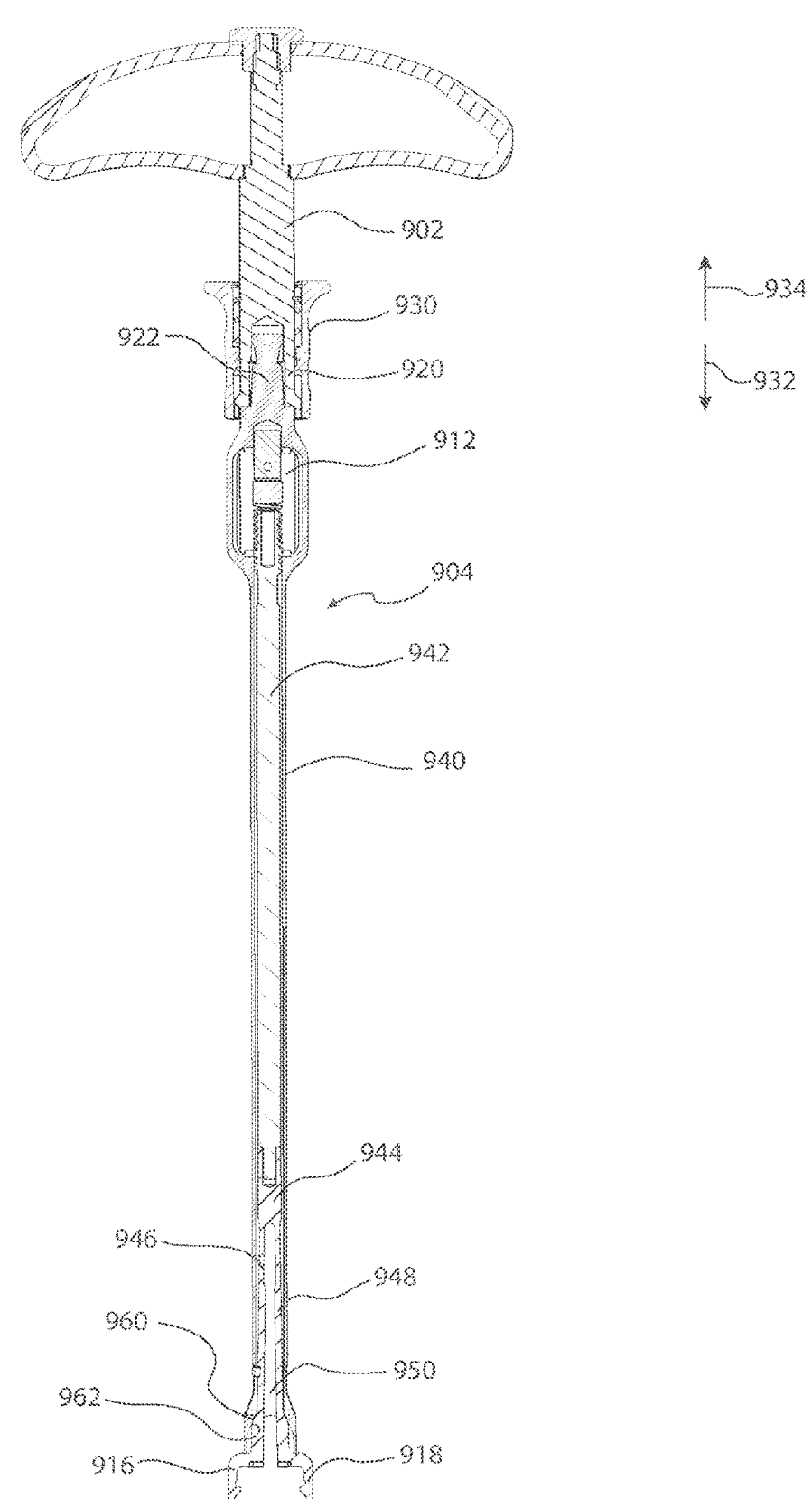
FIG. 40 is a cross-sectional view of the inserter tool of FIG. 39 showing a handle assembly and a shaft assembly of the inserter tool.

With reference to FIG. 40, the handle assembly 902 has a socket 920 that receives a drive member 922 of the shaft assembly 904. The quick release mechanism 906 includes a spring and a sleeve 930 that is urged by the spring in direction 932 to a retention position. When the sleeve 930 is in the retention position, the sleeve 930 shifts detent balls of the quick release mechanism 906 radially inward such that the detent balls resist removal of the drive member 922. To release the shaft assembly 904 from the handle assembly 902, the sleeve 930 is shifted in direction 934 against the bias of the spring which permits the detent balls to shift radially outward and allows the drive member 922 to be withdrawn from the socket 920.

The shaft assembly 904 includes an outer sleeve 940 and an inner shaft 942. The inner shaft 942 is threadedly engaged with the knob 912. The inner shaft 942 is connected to an inserter fork 944 having resilient fork members 946, 948 that are separated from each other by a gap 950. The fork members 946, 948 include the arms 916, 918. To shift the arms 916, 918 toward one another, the knob 912 is turned in direction 952 which draws the inserter shaft 952 proximally in direction 934. The proximal shifting of the inserter shaft 942 in direction 934 causes camming engagement between surfaces 960, 962 of the outer sleeve 940 and fork members 946, 948. This camming engagement shifts the arms 916, 918 toward each other. To release the inserter arms 916, 918 from the implant 200, the knob 912 is turned in a direction opposite direction 952 to shift the inner shaft 942 and inserter fork 944 distally and the resilient properties of the fork members 946, 948 urge the arms 916, 918 apart.

Figure 41:
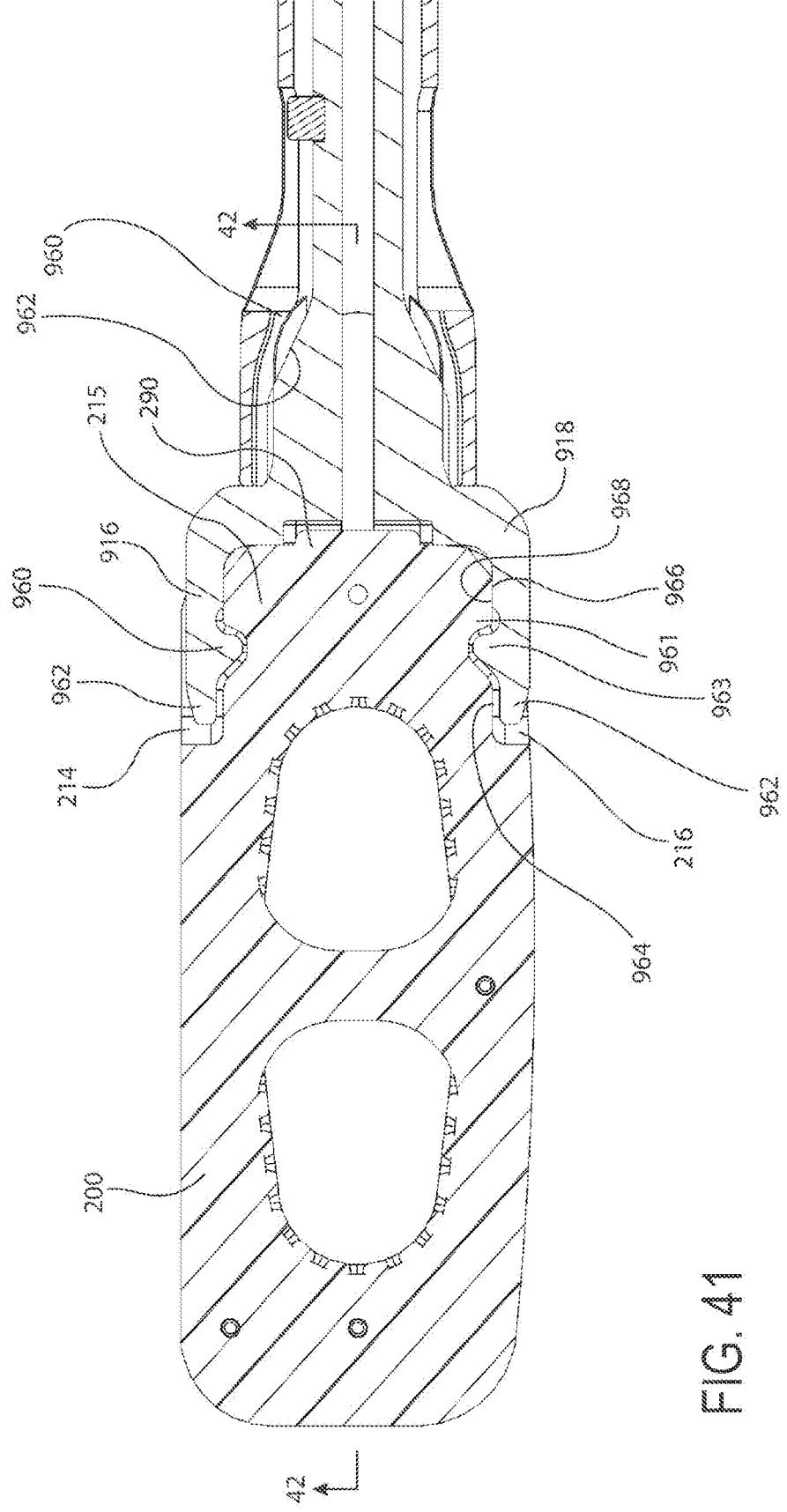
FIG. 41 is a cross-sectional view of a distal end of the shaft assembly of FIG. 40 connected to the implant of FIG. 9.

With reference to FIG. 41, the inserter tool 900 engages the implant 200 in a manner similar to engagement between the inserter tool 700 and the implant 10. The arms 916, 918 have projections 963 that extend into the cavities 300, 302 and mate with walls 961 of the attachment member 215. The arms 916, 918 also include tips 962 that extend along walls 964 of the implant 200. The arms 916, 918 also include inner surfaces 966 that press against and engage surfaces 968 of the attachment member 215.

Figure 42:
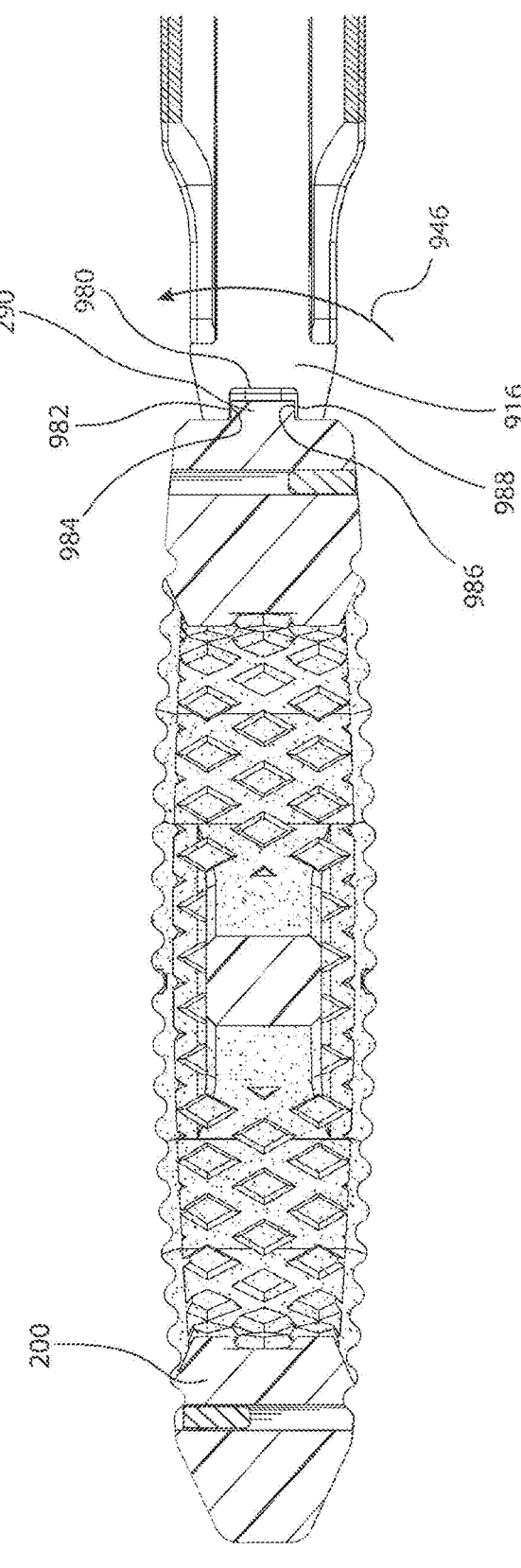
FIG. 42 is a cross-sectional view taken across line 42-42 in FIG. 41 showing a boss of the implant received as a plug in a socket of arms of the shaft assembly of FIG. 40.

With reference to FIG. 42, one difference between the inserter tools 700, 900 is that the inserter 900 has a socket 980 defined by the arms 916, 918 rather than the outer sleeve 940. The socket 980 engages the boss 290 of the implant 200 to improve the strength of the connection between the implant 200 and the inserter 900. The socket 980 includes surfaces 982, 988 that contact surfaces 984, 986 of the boss 290 and increase the longitudinal extent of the engagement between the implant 200 and the inserter 900. The arms 916, 918 also engage the ceilings 990 and floors 992 (see FIG. 12) of the body 202 to transfer loading such as by lifting of the shaft assembly 904 in direction 996 to the implant 200.

Figure 43:
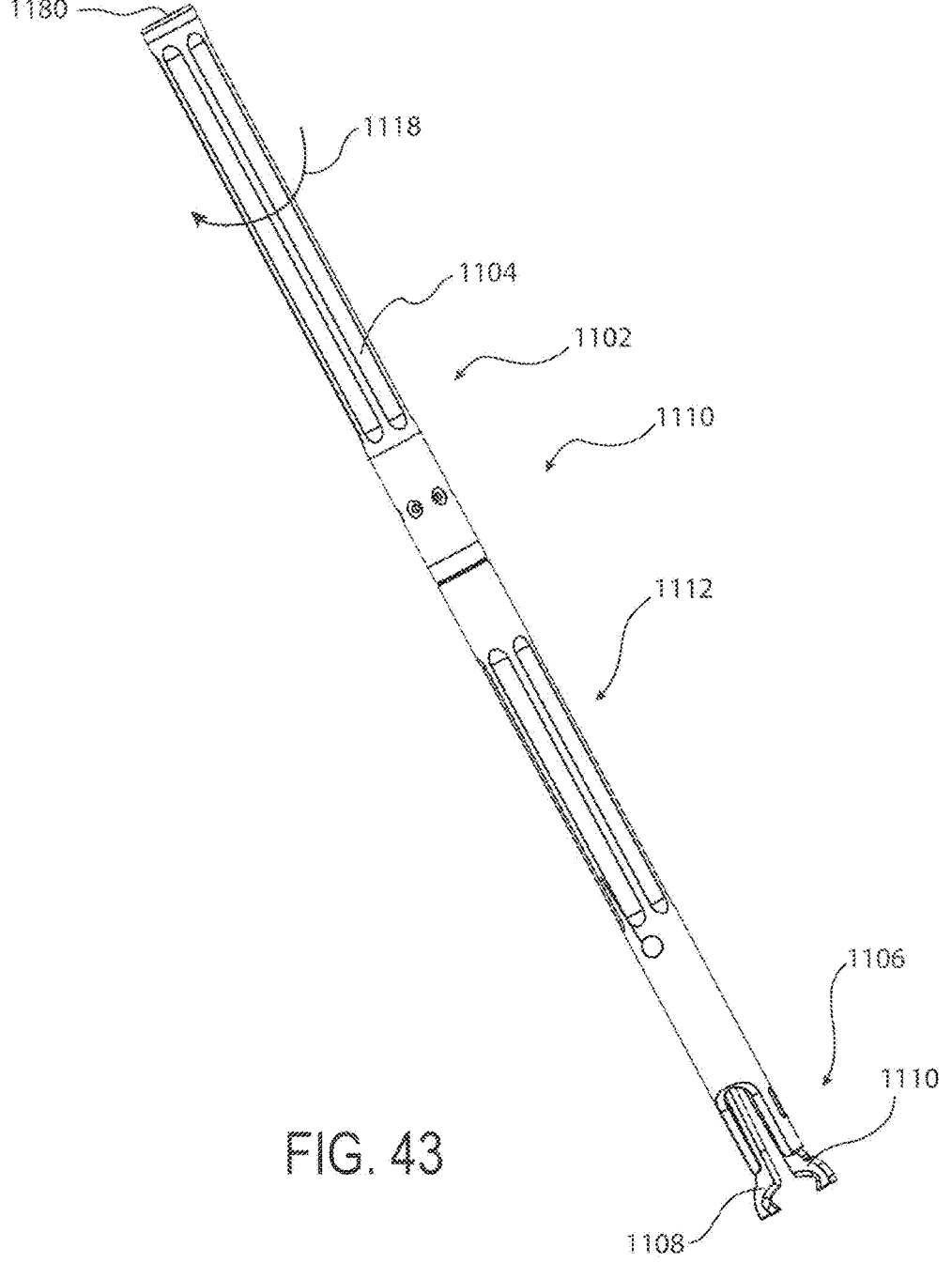
FIG. 43 is a perspective view of an inserter tool for inserting the implant of FIG. 13.
Figure 44:
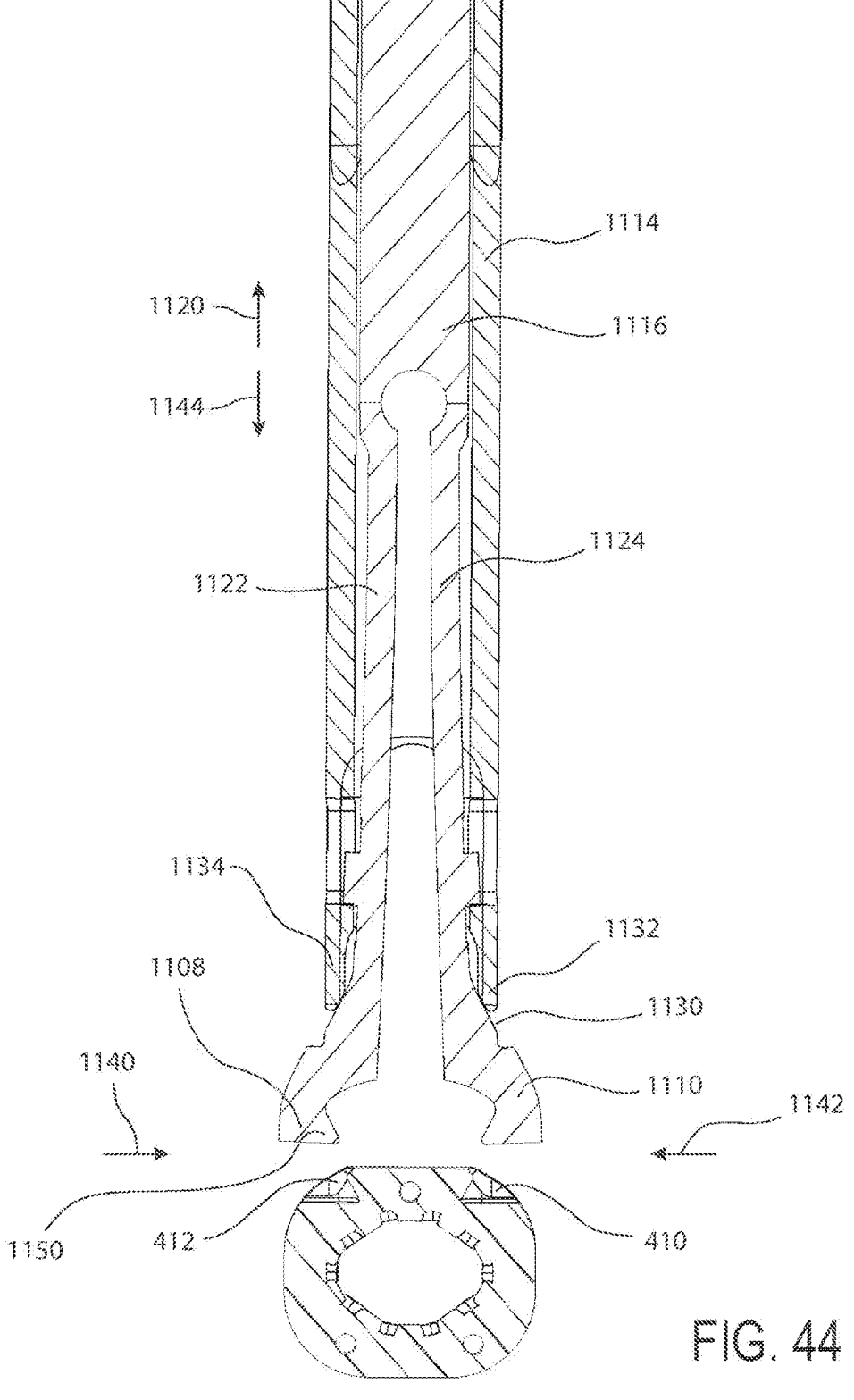
FIG. 44 is a cross-sectional view of a distal end of the inserter of the FIG. 43 and the implant of FIG. 13 showing arms of the inserter in a release position ready to receive the attachment member of the implant.

With reference to FIG. 43, an inserter tool 1100 is provided for positioning the implant 400. The inserter tool 1100 is similar in many respects to the inserter tools 700, 900 discussed above such that differences between the inserters will be discussed. The inserter tool 1100 has a proximal end portion 1102 with a rotatable handle 1104 and a distal end portion 1106 with arms 1108, 1110 for releasably clamping the implant 400. The inserter tool 1100 includes a shaft assembly 1112 having an outer shaft 1114 and an inner shaft 1116. Turning the handle 1104 in direction 1118 draws the inner shaft 1116 proximally in direction 1120. The inner shaft 1116 includes resilient fork members 1122, 1124 that include the arms 1108, 1110. The shifting of the inner shaft 1116 proximally in direction 1120 causes camming engagement between surfaces 1130 of the arms 1108, 110 and a surface 1132 of a distal end portion 1134 of the outer shaft 1114. This urges the arms 1108, 1110 together in directions 1140, 1142 to clamp the dovetail projection 414 of the implant 400 therebetween. Conversely, turning the handle 1104 in a direction opposite to direction 1118 shifts the inner shaft 1116 distally in direction 1144 and the resiliency of the fork members 1122, 1124 causes the arms 1108, 1110 to shift apart.

Figure 45:
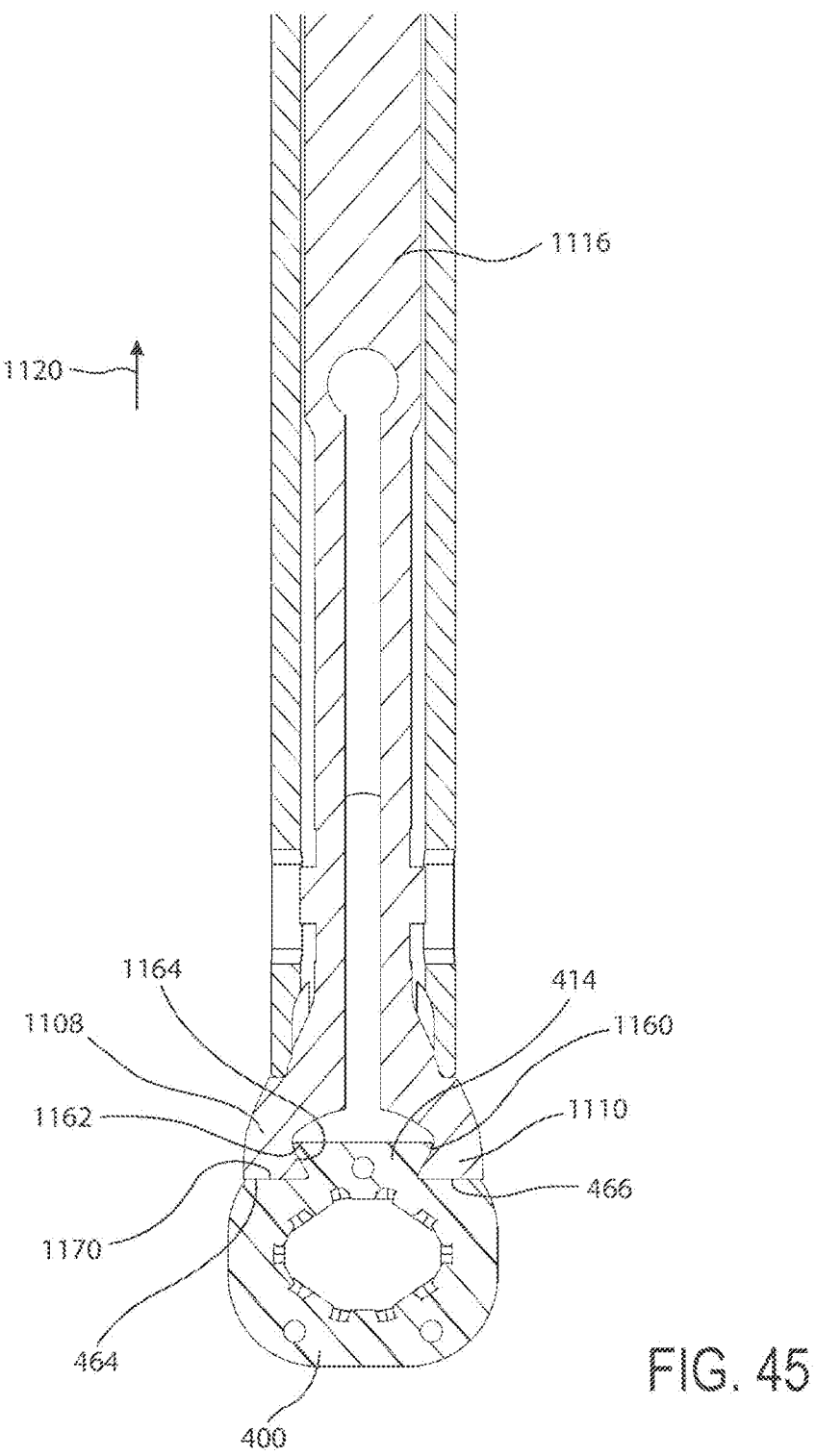
FIG. 45 is a cross-sectional view similar to FIG. 44 showing the arms of the inserter in clamping positions to secure the arms to the implant.

The arms 1110, 1112 include projections 1150 that are positioned in the recesses 410, 412 on opposite sides of the dovetail projection 414. With reference to FIG. 45, turning of the handle 1104 in direction 1118 has urged the inner shaft 1116 proximally in direction 1120 and has engaged the arms 1108, 1110 against the dovetail projection 414. The arms 1108, 1110 are shaped to form a dovetail recess 1160 between the arms 1108, 1110 that has a mating fit with the dovetail projection 414. Further, the projections 1150 have inclined surfaces 1162 that engage inclined surfaces 1164 of the dovetail projection 414 and urge the implant 400 tightly into engagement with the arms 1108, 1110 as the arms 1108, 1110 clamp the dovetail projection 414 therebetween.

The arms 1108, 1110 include flats 1170 that abut the walls 464, 466 of the implant 400. During insertion of the implant 400, the surgeon may tap a hammer on a proximal end 1180 of the handle 1104 and the inserter 1100 transmits these impacts against the implant 400 by way of the engagement between the flats 1170 and the walls 464, 466.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A spinal implant for fusing vertebral bones, the spinal implant comprising:
   a polymer body fabricated using additive manufacturing;
   a through opening of the polymer body to receive bone growth material; an annular wall of the polymer body extending about the through opening;
   an attachment member of the polymer body extending outward of the annular wall;
   opposite lateral sides of the attachment member configured to be clamped between clamping arms of an inserter tool;
   a narrower portion of the attachment member including a first pair of opposite side surface portions having a first width therebetween across the attachment member;
   a wider portion of the attachment member spaced from the annular wall with the narrower portion intermediate the wider portion and the annular wall along the attachment member, the wider portion of the attachment member including a second pair of opposite side surface portions with a second width therebetween across the attachment member that is larger than the first width, the wider portion of the attachment member configured to be in interference with the clamping arms to inhibit separation of the spinal implant from the inserter tool while the clamping arms clamp the attachment member therebetween.

2. The spinal implant of claim 1 wherein the attachment member includes tapered opposite side surface portions connecting the first opposite side surface portions and the second opposite side surface portions.

3. The spinal implant of claim 1 wherein the annular wall includes opposite lateral sides having outer side surface portions adjacent the attachment member, the outer side surface portions of the annular wall having a third width across the polymer body that is larger than the first width.

4. The spinal implant of claim 1 wherein the attachment member includes notches in the opposite lateral sides thereof extending toward one another; and
   wherein the first pair of side surface portions of the narrower portion of the attachment member define at least a portion of the notches.

5. The spinal implant of claim 1 wherein the polymer body includes recesses extending along the opposite lateral sides of the attachment member to receive distal end portions of the clamping arms of the inserter tool.

6. The spinal implant of claim 1 wherein the attachment member comprises a dovetail projection including the narrower portion and the wider portion.

7. The spinal implant of claim 1 wherein the polymer body is monolithic and includes an upper surface having upper gripping members to engage an upper vertebra and a lower surface having lower gripping members to engage a lower vertebra.

8. The spinal implant of claim 1 wherein the annular wall includes upper and lower bone engaging portions; and
   wherein the polymer body includes floor and ceiling portions above and below the lateral sides of the attachment member, the floor and ceiling portions having surfaces to contact distal end portions of the inserter tool clamping arms and resist relative movement of the spinal implant and the inserter tool clamping arms with the attachment member clamped between the inserter tool clamping arms.

9. The spinal implant of claim 1 wherein the annular wall includes nubs extending into the through opening to increase surface area of the annular wall available for bone on-growth.

10. The spinal implant of claim 9 wherein the nubs include nanostructures comprising peaks and valleys to encourage bone fusion interaction in the through opening of the polymer body.

11. The spinal implant of claim 1 wherein the polymer body includes macrostructures having surfaces comprising micropores and nanostructures.

12. The spinal implant of claim 1 wherein the polymer body includes a surface comprising: micropores having an average pore diameter in the range of approximately 500 micrometers to approximately 600 micrometers; and peak-and-valley nanostructures having an average peak-to-peak distance of approximately 265-282 nanometers.

13. The spinal implant of claim 1 wherein the polymer body comprises unmachined, irregular surfaces; and wherein the attachment member comprises machined surfaces having a surface roughness that is less rough than a surface roughness of the unmachined, irregular surfaces of the polymer body.

14. The spinal implant of claim 1 wherein the polymer body has a leading end portion and a trailing end portion and a longitudinal length extending therebetween;

wherein the attachment member includes a trailing surface and a boss protruding from the trailing surface that increases the axial length of the attachment member for being engaged by the inserter tool.

15. The spinal implant of claim 1 wherein the polymer body is free of threads.

16. The spinal implant of claim 1 wherein the annular wall is free of through apertures in communication with the through opening.

\* \* \* \* \*